(12) United States Patent
Tsai et al.

(10) Patent No.: US 12,714,711 B2
(45) Date of Patent: Aug. 25, 2026

(54) SALTS OF NEUROCEUTICALS AND USES THEREOF

(71) Applicant: SyneuRx International (Taiwan) Corp., New Taipei City (TW)

(72) Inventors: Guochuan Emil Tsai, Pasadena, CA (US); Ching-Cheng Wang, New Taipei City (TW); Tien-Lan Hsieh, New Taipei City (TW); Yi-Feng Huang, New Taipei City (TW); Hsin-Hsin Yang, New Taipei City (TW); Ming-Hong Chien, New Taipei City (TW); Han-Yi Hsieh, New Taipei City (TW); Wei-Hua Chang, New Taipei City (TW)

(73) Assignee: SYNEURX INTERNATIONAL (TAIWAN) CORP.

( * ) Notice: Subject to any disclaimer, the term of this patent is extended or adjusted under 35 U.S.C. 154(b) by 743 days.

(21) Appl. No.: 17/998,152

(22) PCT Filed: May 5, 2021

(86) PCT No.: PCT/IB2021/053814
§ 371 (c)(1),
(2) Date: Nov. 7, 2022

(87) PCT Pub. No.: WO2021/224830
PCT Pub. Date: Nov. 11, 2021

(65) Prior Publication Data

US 2023/0218623 A1 Jul. 13, 2023

Related U.S. Application Data

(60) Provisional application No. 63/020,223, filed on May 5, 2020.

(51) Int. Cl.
*A61K 31/519* (2006.01)
*A61K 31/195* (2006.01)
(Continued)

(52) U.S. Cl.
CPC .......... *A61K 31/519* (2013.01); *A61K 31/195* (2013.01); *A61K 31/5513* (2013.01);
(Continued)

(58) Field of Classification Search
CPC ................ A61K 31/519; A61K 31/195; A61K 31/5513; A61K 31/554; A61K 45/06;
(Continued)

(56) References Cited

U.S. PATENT DOCUMENTS 3,542,769 A 11/1970 Kaiser et al.
6,733,797 B1 * 5/2004 Summers .............. A61K 36/16 424/766

(Continued)

FOREIGN PATENT DOCUMENTS

AR 047459 A1 1/2006
CN 1239158 C 2/2006

(Continued)

OTHER PUBLICATIONS

Rahman et al., Tannate complexes of antihistaminic drug: Sustained release and taste masking approaches, Int. J. Pharmaceut., 422, pp. 91-100 (Year: 2012).*

(Continued)

*Primary Examiner* — Jeffrey S Lundgren
*Assistant Examiner* — Alexander K. Showalter
(74) *Attorney, Agent, or Firm* — Mintz, Levin, Cohn, Ferris, Glovsky and Popeo, P.C

(57) ABSTRACT

A salt of a neuroceutical and of an acid, wherein the neuroceutical is a substituted benzodiazepine, a substituted benzothiazepine, a substituted pyridopyrimidines or a sub-
(Continued)

stituted amino-cyclohexaneacetic acid; and the acid is benzoic acid, nicotinic acid, pantothenic acid and tannic acid. The molar ratio of the neuroceutical and the acid in the salt ranges from about 6:1 to about 1:5. Also disclosed herein are compositions comprising the neuroceutical salt and therapeutic uses thereof for treating a central nervous system (CNS) disorder or a metabolic disorder associated with the CNS disorder.

18 Claims, 53 Drawing Sheets

(51) Int. Cl.

| | |
|---|---|
| ***A61K 31/455*** | (2006.01) |
| ***A61K 31/496*** | (2006.01) |
| ***A61K 31/551*** | (2006.01) |
| ***A61K 31/5513*** | (2006.01) |
| ***A61K 31/554*** | (2006.01) |
| ***A61K 45/06*** | (2006.01) |
| ***A61P 3/10*** | (2006.01) |
| ***A61P 25/00*** | (2006.01) |
| ***A61P 25/18*** | (2006.01) |
| ***C07D 213/80*** | (2006.01) |
| ***C07D 243/38*** | (2006.01) |
| ***C07D 281/16*** | (2006.01) |
| ***C07D 309/10*** | (2006.01) |
| ***C07D 417/12*** | (2006.01) |
| ***C07D 471/04*** | (2006.01) |
| ***C07D 493/04*** | (2006.01) |
| ***C07D 495/04*** | (2006.01) |

(52) U.S. Cl.
CPC ............ *A61K 31/554* (2013.01); *A61K 45/06* (2013.01); *A61P 3/10* (2018.01); *A61P 25/18* (2018.01); *C07B 2200/13* (2013.01)

(58) Field of Classification Search
CPC .. A61K 31/496; A61K 31/551; A61K 31/455; A61P 3/10; A61P 25/18; A61P 25/00; C07B 2200/13; C07D 243/38; C07D 281/16; C07D 309/10; C07D 471/04; C07D 493/04; C07D 213/80; C07D 417/12; C07D 495/04
See application file for complete search history.

(56) References Cited

U.S. PATENT DOCUMENTS 7,459,449 B2 * 12/2008 Keltjens .................. A61P 25/18 540/557
7,550,628 B2 * 6/2009 Kiel .................. A61K 31/7024 562/507
2019/0274984 A1 9/2019 Tsai et al.

FOREIGN PATENT DOCUMENTS

| | | | |
|---|---|---|---|
| CN | 101084222 | A | 12/2007 |
| CN | 104327095 | A | 2/2015 |
| CN | 112142746 | A | 12/2020 |
| WO | WO 99/16313 | A1 | 4/1999 |
| WO | WO 2005/070938 | A1 | 8/2005 |
| WO | 2006/010620 | A2 | 2/2006 |
| WO | 2006/056772 | A2 | 6/2006 |
| WO | 2007/032695 | A1 | 3/2007 |
| WO | 2007/102074 | A2 | 9/2007 |

OTHER PUBLICATIONS

Thakuria et al., Olanzapinium Salts, Isostructural Solvates, and Their Physicochemical Properties, Cryst. Growth & Design, 13, pp. 3672-3680 (Year: 2013).*

Kaur et al., The crystal structures of three clozapinium salts: different molecular configurations, and supraÂ-molecular assembly in one, two and three dimensions, Acta Crystallogr. E Crystallogr. Commun., 71, pp. 406-413 (Year: 2015).*

Ravikumar, K., et al. "Olazipinium nicotinate" Acta Crystallographica Section E: Structure Reports Online, vol. 61, No. 8, pp. 02720-02723, Aug. 2005.

* cited by examiner (A)

(B)

(A)

(B)

(A)

(B)

(A)

(B)

SALTS OF NEUROCEUTICALS AND USES THEREOF

CROSS REFERENCE TO RELATED APPLICATIONS

This application is a United States National Phase under 35 U.S.C. § 371 of International Application No. PCT/IB2021/053814, filed May 5, 2021, which claims the benefit of the filing date of U.S. Provisional Application No. 63/020,223, filed May 5, 2020, the entire contents of both of which are incorporated by reference herein in their entirety.

BACKGROUND OF THE INVENTION

The central nervous system (CNS) includes the brain and spinal cord, and is vulnerable to disorders that may be caused by various factors, including trauma, infections, degeneration, structural defects and/or damages, tumors, blood flow disruption, and autoimmune disorders. Symptoms of a CNS disorder depend on the area of the nervous system that is involved and the cause of the disorder.

The development of effective therapies for CNS disorders has lagged behind other therapeutic areas, due to the complexity of the CNS disorders and the difficulties associated with delivering therapeutic agents across the blood-brain barrier. Furthermore, numerous neuroceuticals approved for treating CNS disorders are associated with undesirable side effects, such as metabolic disorders or diseases.

Different crystal and/or salt forms of a therapeutic compound may have different the physicochemical or biopharmaceutical properties. These different properties may include different chemical stabilities, solubilities, bioavailabilities (including, for example, improved passage through the blood-brain barrier) and/or reduced side effects. Accordingly, it is of great interest to develop new forms of therapeutic agents that have improved properties, and to use these new forms to treat CNS disorders, especially if the new form exhibits decreased or even no side effects.

SUMMARY OF THE INVENTION

The present disclosure is based on the unexpected discovery that some acid addition salts of certain CNS drugs exhibited improved properties, such as improved water solubility, improved physical features such as flowability, increased bioavailability, mitigated side effects (such as metabolic syndromes induced by treatment with the neuroceuticals) improved pharmacodynamic effects, enhanced therapeutic effects (e.g., for treating neuropsychiatric disorders and/or metabolism disorders), or a combination thereof. The acids used to prepare the salts include, for example, nicotinic acid, benzoic acid, pantothenic acid, and tannic acid.

Accordingly, some aspects of the present disclosure features a salt of a neuroceutical and an acid. In some embodiments, the neuroceutical is a substituted benzodiazepine, a substituted benzothiazepine, a substituted pyridopyrimidine or a substituted amino-cyclohexaneacetic acid; and the acid can be benzoic acid, nicotinic acid, pantothenic acid, or tannic acid. The molar ratio of the neuroceutical and the acid in the salt may range from about 6:1 to about 1:5. In some examples, the neuroceutical is clozapine, olanzapine, quetiapine, risperidone, paliperidone, lurasidone, or gabapentin.

In some embodiments, the molar ratio of the neuroceutical and the acid in the salt is 1:1. For example, (a) the acid is benzoic acid and the neutoceutical is clozapine, paliperidone, or lurasidone; (b) the acid is nicotinic acid and the neuroceutical is clozapine, olanzapine, quetiapine, or risperidone; or (c) the acid is tannic acid and the neuroceutical is gabapentin. In specific examples:

- the salt is a benzoic acid salt of clozapine, and wherein the salt comprises a solid form having a powder X-ray diffraction pattern, which comprises characteristic peaks at a reflection angel 2θ of approximately 7.6, 12.4, 13.6, 15.3, 15.7, 16.0, 19.5, 19.9, 23.1, 24.9, 25.1, and 28.4 degrees;
- the salt is a nicotinic acid salt of clozapine, and wherein the nicotinic acid salt of clozapine comprises a solid form having a powder X-ray diffraction pattern, which comprises characteristic peaks at a reflection angel 2θ of approximately 7.7, 8.2, 10.9, 12.6, 13.8, 16.0, 17.9, 18.2, 18.8, 19.5, 21.9, 22.2, 22.4, 23.3, 24.1, 25.2, 31.2, 31.5, 35.0, and 44.2 degrees;
- the salt is a nicotinic acid salt of olanzapine, and wherein the nicotinic acid salt of olanzapine comprises a solid form having a powder X-ray diffraction pattern, which comprises characteristic peaks at a reflection angel 2θ of approximately 7.9, 8.1, 9.6, 13.7, 15.8, 16.4, 17.2, 17.9, 19.3, 24.3, 29.4, 33.1, 34.6, 39.4, and 42.7 degrees;
- the salt is a nicotinic acid salt of quietiapine, and wherein the nicotinic acid salt of quetiapine comprises a solid form having a powder X-ray diffraction pattern, which comprises characteristic peaks at a reflection angel 2θ of approximately 6.2, 9.2, 10.3, 11.4, 12.4, 12.9, 16.2, 16.5, 17.0, 17.2, 17.3, 17.5, 19.4, 19.9, 21.1, 21.3, 22.1, 27.1, 32.9, and 35.6 degrees;
- the salt is a nicotinic acid salt of risperidone, and wherein the nicotinic acid salt of risperidone comprises a solid form having a powder X-ray diffraction pattern, which comprises characteristic peaks at a reflection angel 2θ of approximately 9.7, 10.9, 12.0, 12.4, 14.4, 17.1, 17.4, 24.4, 36.8, 42.8, and 44.1 degrees; or the salt is a benzoic acid salt of paliperidone, and wherein the benzoic acid salt of paliperidone comprises a solid form having a powder X-ray diffraction pattern, which comprises characteristic peaks at a reflection angel 2θ of approximately 6.8, 9.0, 10.9, 11.4, 11.8, 16.6, 18.3, 18.6, 20.8, 22.2, 22.8, 27.5, 29.0, 30.3, and 32.3 degrees.

In some embodiments, the molar ratio of the neuroceutical and the acid in the salt is 1:2. For example, (a) the acid is tannic acid and the neuroceutical is clozapine or gabapentin, or (b) the acid is nicotinic acid and the neuroceutical is paliperidone. In a specific example, the salt is a nicotinic acid salt of paliperidone, and wherein the nicotinic acid salt of paliperidone comprises a solid form having a powder X-ray diffraction pattern, which comprises peaks at a reflection angel 2θ of approximately 6.7, 8.9, 11.0, 11.2, 11.7, 16.1, 16.4, 17.6, 18.4, 22.8, 27.2, and 29.9 degrees.

In some embodiments, the molar ratio of the neuroceutical and acid in the salt is 1:3. For example, the salt is a tannic acid salt of gabapentin.

In some embodiments, the molar ratio of neuroceutical and acid in the salt is 2:1. For example, the acid is tannic acid, and the neuroceutical is clozapine, olanzapine, or gabapentin.

In some embodiments, the molar ratio of the neuroceutical and acid in the salt is 3:1. For example, the salt is a tannic acid salt of gabapentin.

In some embodiments, the molar ratio of the neuroceutical and acid in the salt is 4:1. For example, the salt is a tannic acid salt of clozapine.

In some embodiments, the molar ratio and acid in the salt is 5:1. For example, the salt is a pantothenic acid salt of olanzapine, and wherein the pantothenic acid salt comprises a solid form having a powder X-ray diffraction pattern, which comprises characteristic peaks at a reflection angel 2θ of approximately 7.7, 8.1, 8.7, 11.2, 11.7, 13.5, 15.4, 16.0, 16.2, 16.4, 19.0, 20.3, 22.2, 22.4, 23.1, 24.4, 25.7, 25.8, 26.7, 27.7, 29.4, 33.6, 34.3, 34.6, and 37.7 degrees.

In another aspect, provided herein is a composition comprising any of the salts disclosed herein and a pharmaceutically acceptable carrier. In some instances, the composition further comprises an additional therapeutic agent, which is different from the neuroceutical in the salt. For example, the additional therapeutic agent is an antipsychotic drug, an antidepressant drug, an analgesic drug, an anticonvulsant drug, or a neurodegeneration drug. Examples of the additional therapeutic agents include, but are not limited to, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, LY2140023, droperidol, pimozide, butaperazine, carphenazine, remoxipride, piperacetazine, sulpiride, acamprosate, chlorpromazine, blonanserine, bromperidol, carpipramine, clocapramine, clotiapine, cyamemazine, fluspirilene, haloperidol, iloperidone, loxapine, lurasidone, melperone, molindone, mosapramine, nemonapride, oxypertine, penfluridol, pyrazine, pericyazine, perospirone, pipamperone, pipotiazine, prothipendyl, sertindole, spiperone, sultopride, tiapride, timiperone, zotepine, haloperidol decanoate, fluphenazine decanoate, fluphenazine enanthate, risperdal consta, acetophenazine, donepezil, galantamine, memantine, riluzole, rivastigmine, tacrine, bupropion, lithium, mirtazapine, nortriptyline, sertraline, triiodothyronine, tranylcypromine, venlafaxine, amitriptyline, imipramine, nortriptiline, protriptyline, desipramine, trimipramine, amoxapine, bupropion, citalopram, escitalopram, clomipramine, desipramine, doxepin, duloxetine, milnacipran, fluoxetine, fluvoxamine, imipramine, isocarboxazid, isoniazid, iproniazid, fluoxetine, paroxetine, sarcosine, sertraline fluvoxamine, venlafaxine, velafaxine, milnacipram and duloxetine, mirtazapine, mianserin, reboxetine, selegiline, tranylcypromine, trazodone, nefazodone, phenelzine, diazepam, bromazepam, prazepam, chlordiazepoxide, clobazam, estazolam, flurazepam, clonazepam, temazepam, triazolam, alprazolam, midazolam, brotizolam, nitrazepam, flunitrazepam, oxazepam, quazepam, lorazepam, temazepam, triazolam, zolpidem, zopiclone, zaleplon, carphenazine, remoxipride, piperacetazine, lamatrogine, topiramate, gabapentin, carbamazepine, oxacarbazepine, valporate, maprotiline, brofaromine, gepirone, moclobemide, physostigmine, nicotine, huperzine alpha, vitamin c, vitamin, carotenoids, *Ginkgo biloba*, statinsamphetamine, modafinil, desoxyn, methamphetamine, cocaine, arecoline, dexmethylphenidate, dextroamphetamine, methylphenidate, lisdexamfetamine dimesylate (vyvanse), mixed salts amphetamine, atomoxetine, clonidine hydrochloride, guanfacine hydrochloride, arecoline, pemoline, acetaminophen, aspirin, bromfenac, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, nepafenac, oxaprozin, phenylbutazone, piroxicam, sulindac, tolmetin, celecoxib, lidocaine, nefopam, orphenadrine, cyclobenzaprine, hyoscine, fentanyl, hydrocodone, hydromorphone, levorphanol, meperidine, methadone, oxycodone, oxymorphone, propoxyphene, tapentadol, tramadol, buprenorphine, butorphanol, nalbuphine, pentazocine, acetazolamide, divalproex sodium, eslicarbazepine, ethosuximide, ethotoin, felbamate, fosphenytoin, lacosamide, levetiracetam, mephenytoin, metharbital, methsuximide, methazolamide, oxcarbazepine, phenobarbital, phenytoin, phensuximide, pregabalin, primidone, valproic acid, sodium valproate, stiripentol, tiagabine, topiramate, trimethadione, vigabatrin, zonisamide, xenazine, tereabenazine, baclofen, austedo, lioresal, kemstro, deutetrabenazine, edaravone, acetylcholinesterase (AChE) inhibitors, levodopa, and a monoamine oxidase-B inhibitor.

In yet another aspect, the present disclosure features a method of treating a central nervous system (CNS) disorder or a metabolic disorder associated with a central nervous system (CNS) disorder, the method comprising administering to a human subject in need thereof an effective amount of any of the salts disclosed herein or a composition comprising such as also disclosed herein. In some instances, the method may further comprise administering to the human subject an additional therapeutic agent, which is different from the neuroceutical in the salt, e.g., those disclosed herein. In some examples, the salt is a nicotinic acid salt and wherein the amount of the salt is sufficient to mitigate one or more metabolic symptoms in the human subject.

In some embodiments, the human subject may have or be suspected of having a neuropsychiatric disorder. Examples include, but are not limited to, schizophrenia, psychotic disorder, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorder, attention deficit disorder, obsessive compulsive disorder, tic disorder, childhood learning disorder, premenstrual syndrome, depression, major depressive disorder, anhedonia, suicidal ideation and/or behavior, bipolar disorder, anxiety disorder, panic disorder, post-traumatic stress disorder, chronic mild and unpredictable stress, eating disorder, addiction disorder, personality disorder, Parkinson's disorder, Huntington's disorder, multiple sclerosis, amyotrophic lateral sclerosis, ataxia, Friedreich's ataxia, Tourette's syndrome, nocturnal enuresis, non-epileptic seizure, blepharospasm, Duchenne muscular dystrophy, stroke, chronic pain, neuropathic pain, hyperalgesia, allodynia, diabetic polyneuropathy, seizures and epilepsy. In some examples, the CNS disorder is a neurodegenerative disease, e.g., amyotrophic lateral sclerosis, dementia, Alzheimer's disease, Parkinson's disease, and Huntington's disease.

In some embodiments, the human subject is administered the salt or the composition comprising such at a frequency of four times a day to one time every three months. In some embodiments, the human subject has undergone or is treated concurrently with one or more additional therapeutic agents for the CNS disorder. The one or more therapeutic agents can be different from the neuroceutical in the salt. In some examples, the additional therapeutic agent is an antipsychotic drug, an antidepressant drug, an analgesic drug, an anticonvulsant drug or a neurodegeneration drug. Examples are provided herein.

Also within the scope of the present disclosure are any of the salts disclosed herein or the compositions comprising such for use in treating any of the target CNS disorders or for use in manufacturing a medicament for such therapeutic purposes.

The term "neurodegeneration" is the progressive loss of structure or function of neurons, including the death of neurons. Neurodegenerative diseases include, but are not limited to amyotrophic lateral sclerosis, dementia, and Huntington's disease.

The term "dementia" is a category of brain diseases that cause a long-term and often gradual decrease in the ability to think and remember that is severe enough to affect a person's daily functioning. Other common symptoms include emotional problems, difficulties with language, and a decrease in motivation. Common dementia diseases include, but not limited to Alzheimer's disease, Parkinson's disease, vascular dementia, dementia with Lewy bodies, and frontotemporal dementia.

The term "neuropsychiatric disorder," includes either neurological diseases or psychiatric disorders or CNS disorders, or refers to a disorder that involves either psychiatric symptoms or syndromes caused by organic brain disorders. The main characteristics of neuropsychiatric symptoms include occurrence of the various psychiatric symptoms, cognitive impairment, neurological symptoms or the possibility of early cerebral development symptoms. For example, the neuropsychiatric disorder can include, but not limited to, schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, mania, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, chronic pain syndromes, seizures and epilepsy.

"Metabolism" is includes the enzymatic reactions, helped by minerals and vitamins, by which the body derives energy and synthesizes the other molecules it needs from the fats, carbohydrates and proteins that are eaten as food.

Metabolic syndrome is a cluster of conditions, such as two or more of increased blood pressure, high blood sugar, excess body fat around the waist, abnormal cholesterol or triglyceride levels, hyperglycemia and glucose intolerance that result from ingesting the non-salt form of the neuroceutical. Metabolic syndrome occur simultaneously or essentially simultaneously and can lead to increased risk of heart disease, stroke and/or diabetes.

Types of "Metabolic disorders" include, but are not limited to acid-base imbalance, metabolic brain diseases, disorders of calcium metabolism, DNA repair-deficiency disorders, glucose metabolism disorders, hyperlactatemia, iron metabolism disorders, lipid metabolism disorders, malabsorption syndromes, metabolic syndrome X, inborn error of metabolism, mitochondrial diseases, phosphorus metabolism disorders, porphyrias, proteostasis deficiencies, metabolic skin diseases, wasting syndrome, and water-electrolyte imbalance.

"Metabolic diseases" include, but are not limited to adrenoleukodystrophy, diabetes type 1, Gaucher disease, glucose galactose malabsorption, hereditary hemochromatosis, Lesch-Nyhan syndrome, Maple syrup urine disease, Menkes syndrome, Niemann-Pick disease, obesity, pancreatic cancer, phenylketonuria, Prader-Willi syndrome, *porphyria*, refsum disease, Tangier disease, Tay-Sachs disease, Wilson's disease, and Zellweger syndrome.

The terms "health food" or "health food product" refer to any kind of liquid and solid/semi-solid materials that are used to nourish humans and animals, while ameliorating or improving one or more of basic behavioral functioning, hyperactivity, anxiety, depression, sensorimotor gating, pain threshold, memory and/or cognitive functioning, body weight, or for facilitating treatment of any of the target diseases noted herein.

The term "nutraceutical composition" refers to compositions containing components from food sources and conferring extra health benefits in addition to the basic nutritional value found in foods.

The terms "medical food" or "medical food product" refer to a food product formulated to be consumed or administered enterally, including a food product that is usually used under the supervision of a physician for the specific dietary management of a target disease, such as those described herein.

A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

The details of one or more embodiments of the invention are set forth in the description below. Other features or advantages of the present invention will be apparent from the following drawings and detailed description of several embodiments, and also from the appended claims.

BRIEF DESCRIPTIONS OF THE DRAWINGS

The following drawings form part of the present specification and are included to further demonstrate certain aspects of the present disclosure, which can be better understood by reference to the drawing in combination with the detailed description of specific embodiments presented herein.

FIG. 1 shows a 1H-NMR spectrum of clozapine:benzoic acid 1:1 salt.

FIG. 2 shows a XRPD spectrum of clozapine:benzoic acid 1:1 salt. Angle (2θ) peaks include 7.6; 8.1; 10.5; 12.4; 12.6; 13.6; 15.3; 15.7; 16.0; 16.1; 16.4; 17.6; 18.1; 19.3; 19.5; 19.9; 20.9; 21.2; 21.6; 21.8; 22.2; 22.7; 23.1; 23.3; 23.8; 24.2; 24.4; 24.5; 24.9; 25.1; 26.4; 27.3; 27.6; 27.9; 28.4; 29.8; 30.4; 30.6; 30.9; 31.0; 31.3; 31.5; 31.6; 31.7; 32.2; 32.5; 32.6; 33.2; 33.3; 33.5; 33.8; 34.1; 34.2; 35.1; 35.6; 36.1; 36.9; 37.7; 37.9; 38.3; 38.8; 39.8; 40.2; 40.4; 40.9; 41.7; 42.6; 43.1; 43.3; and 44.0.

24.1; 24.4; 25.2; 25.4; 25.6; 25.9; 26.2; 27.0; 27.8; 28.2; 28.4; 28.8; 29.0; 29.7; 30.1; 30.2; 30.4; 30.5; 31.2; 31.5; 31.6; 31.9; 32.0; 32.2; 32.8; 33.0; 33.2; 34.4; 35.0; 35.6; 36.3; 36.6; 37.0; 37.1; 37.6; 37.7; 37.9; 38.1; 38.2; 38.9; 39.0; 39.3; 39.8; 40.2; 40.7; 41.3; 41.8; 42.1; 42.5; 43.2; 44.1; and 44.2.

Figure 1:
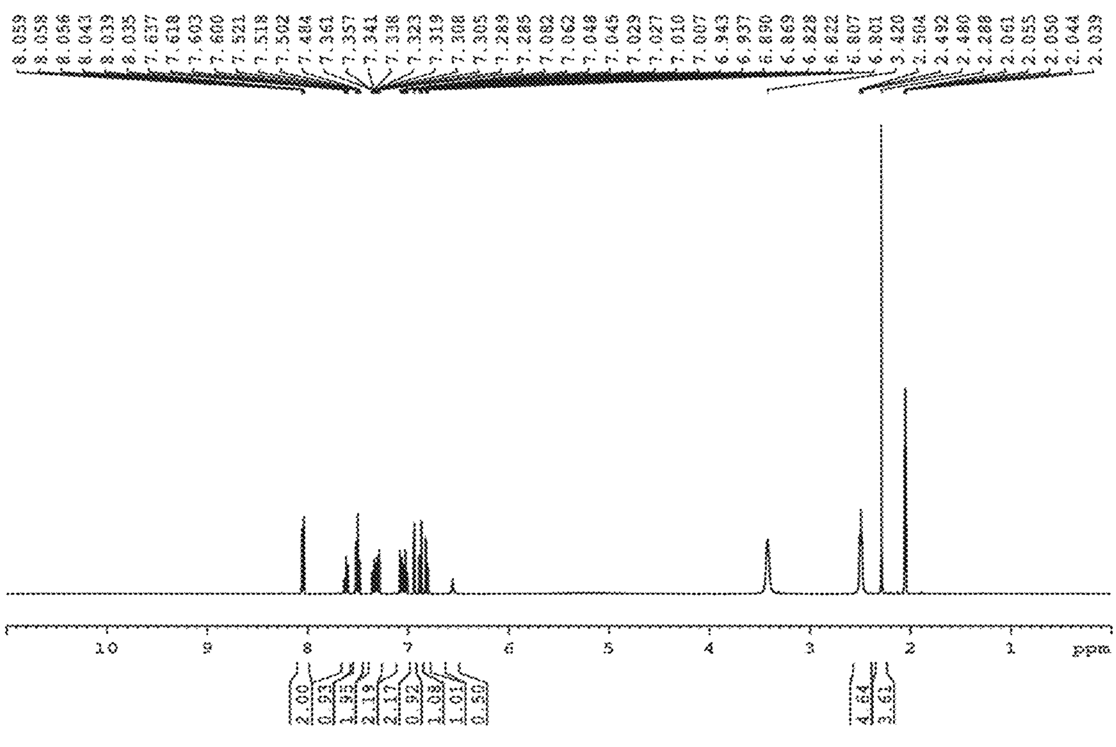
Figure 2:
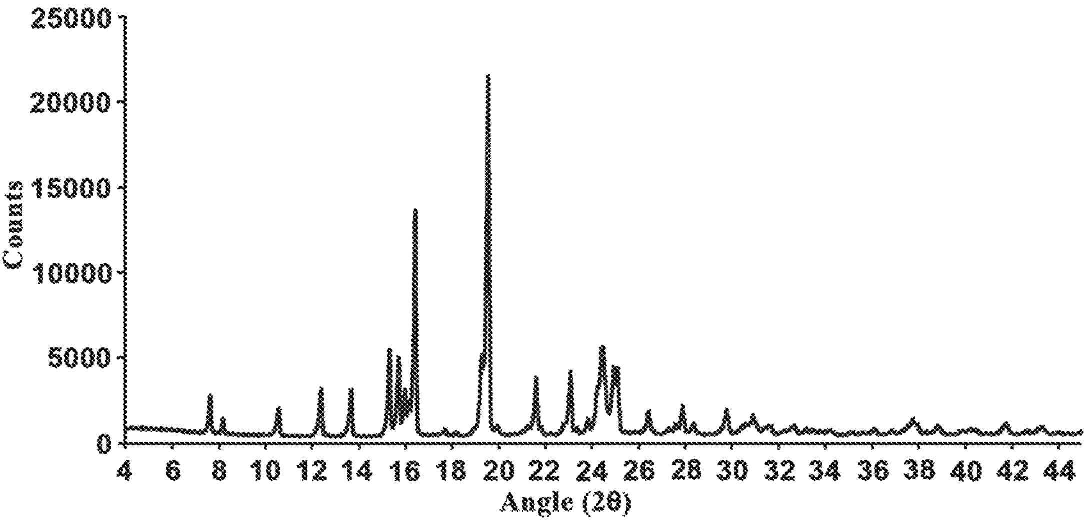
Figure 3:
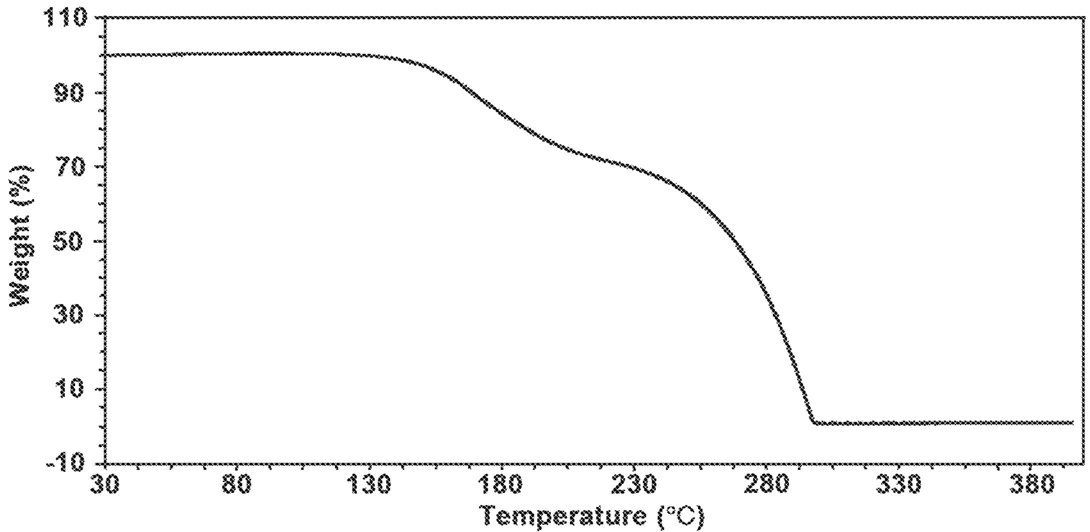
FIG. 3 shows a TGA spectrum of clozapine:benzoic acid 1:1 salt.
Figure 4:
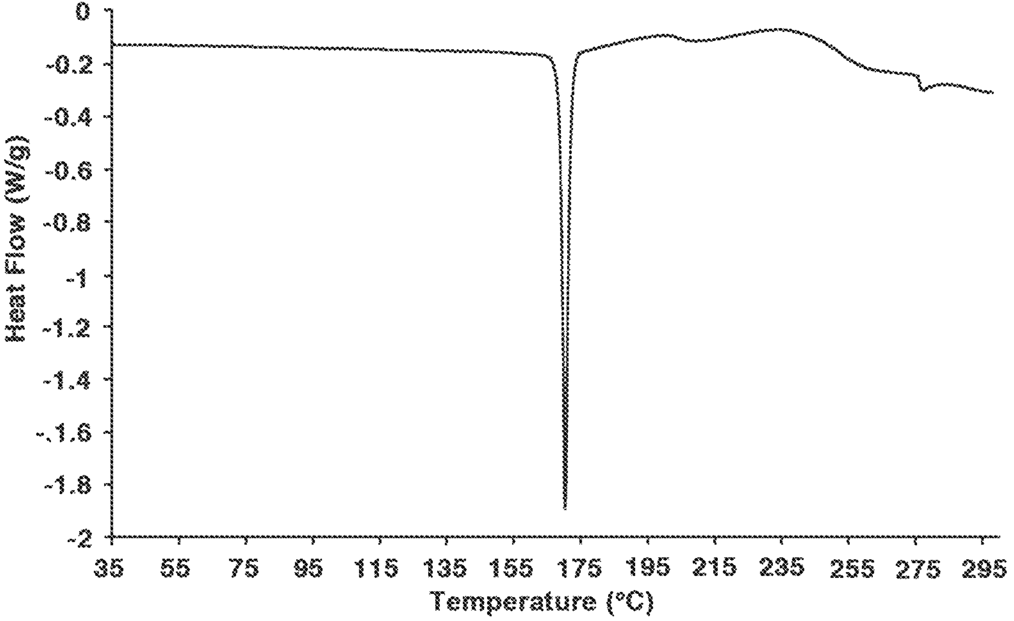
FIG. 4 shows a DSC spectrum of clozapine:benzoic acid 1:1 salt.
Figure 5:
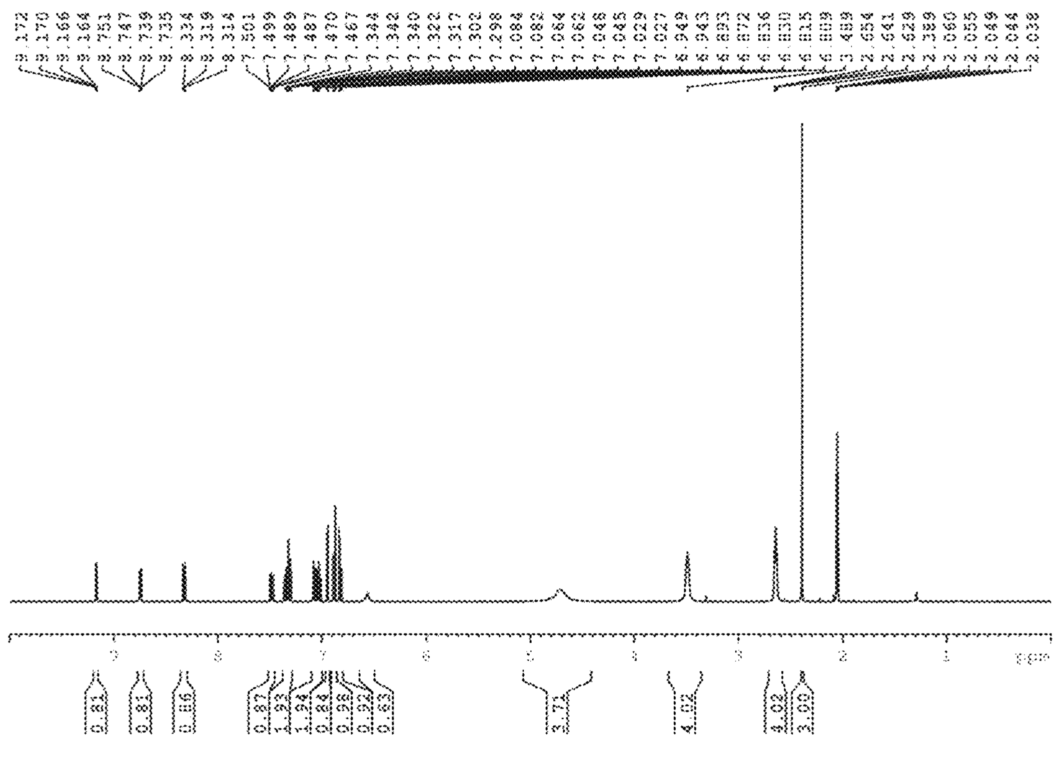
FIG. 5 shows a 1H-NMR spectrum of clozapine:nicotinic acid 1:1 salt (seeds).
Figure 6:
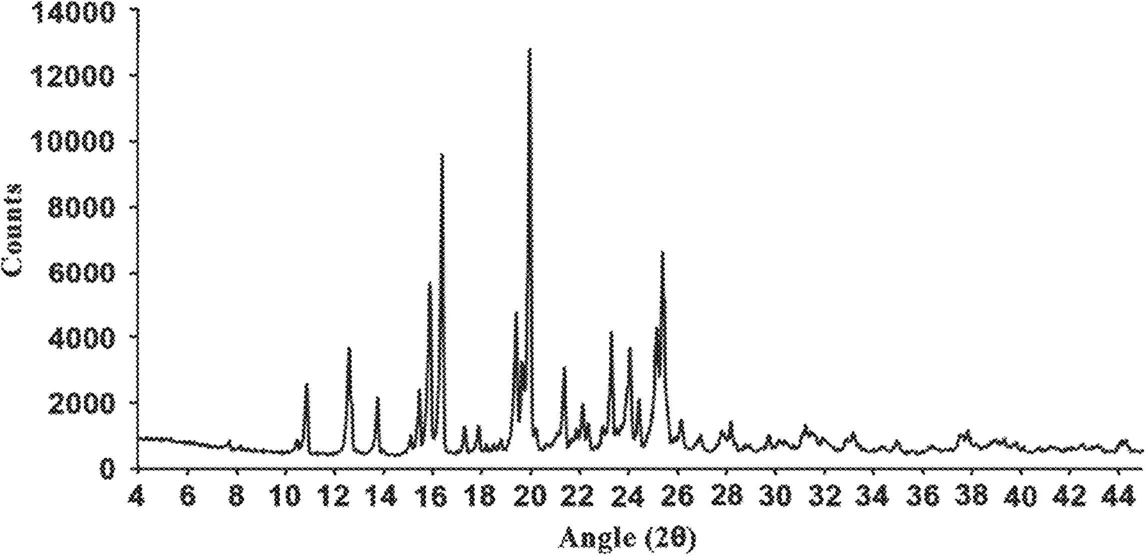
FIG. 6 shows a XRPD spectrum of clozapine:nicotinic acid 1:1 salt (seeds). Angle (2θ) peaks include 7.7; 8.2; 10.4; 10.9; 12.6; 12.9; 13.8; 14.1; 15.1; 15.5; 16.0; 16.5; 17.3; 17.9; 18.2; 18.5; 18.8; 19.5; 19.7; 20.0; 20.2; 20.7; 21.0; 21.4; 21.7; 21.9; 22.2; 22.4; 22.7; 23.0; 23.3; 23.5; 24.0.
Figure 7:
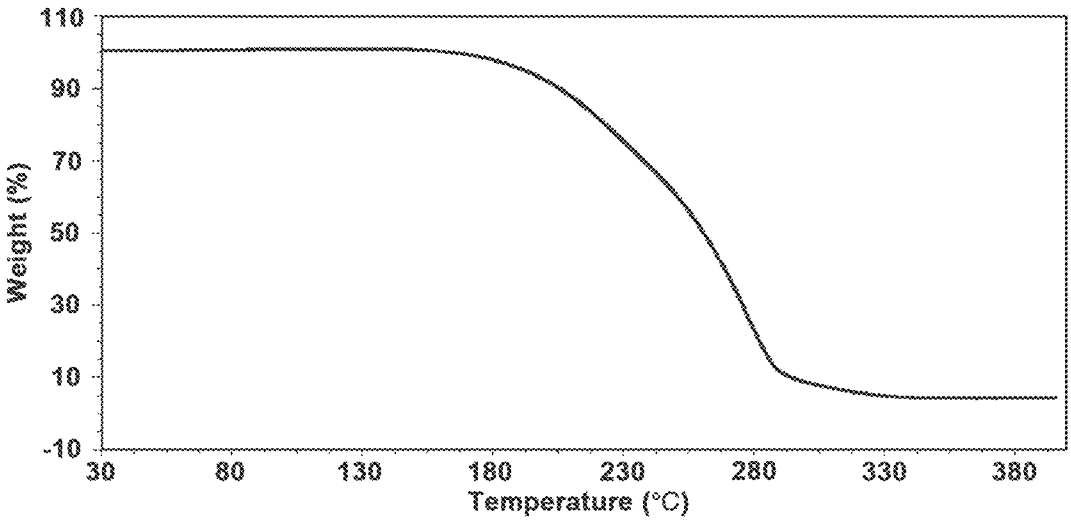

FIG. 7 shows a TGA spectrum of clozapine:nicotinic acid 1:1 salt (seeds).

Figure 8:
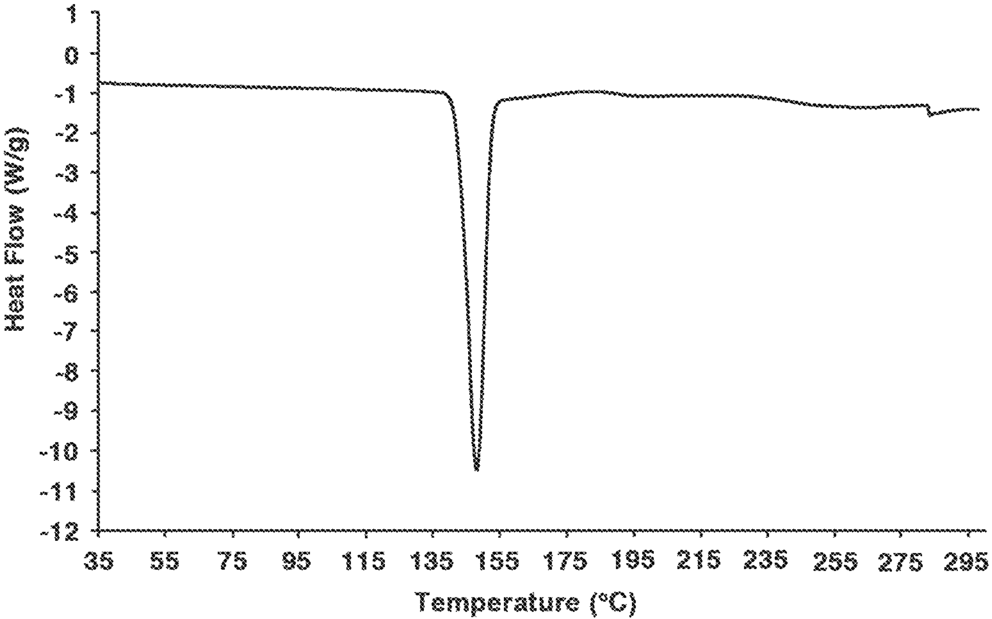

FIG. 8 shows a DSC spectrum of clozapine:nicotinic acid 1:1 salt (seeds).

Figure 9:
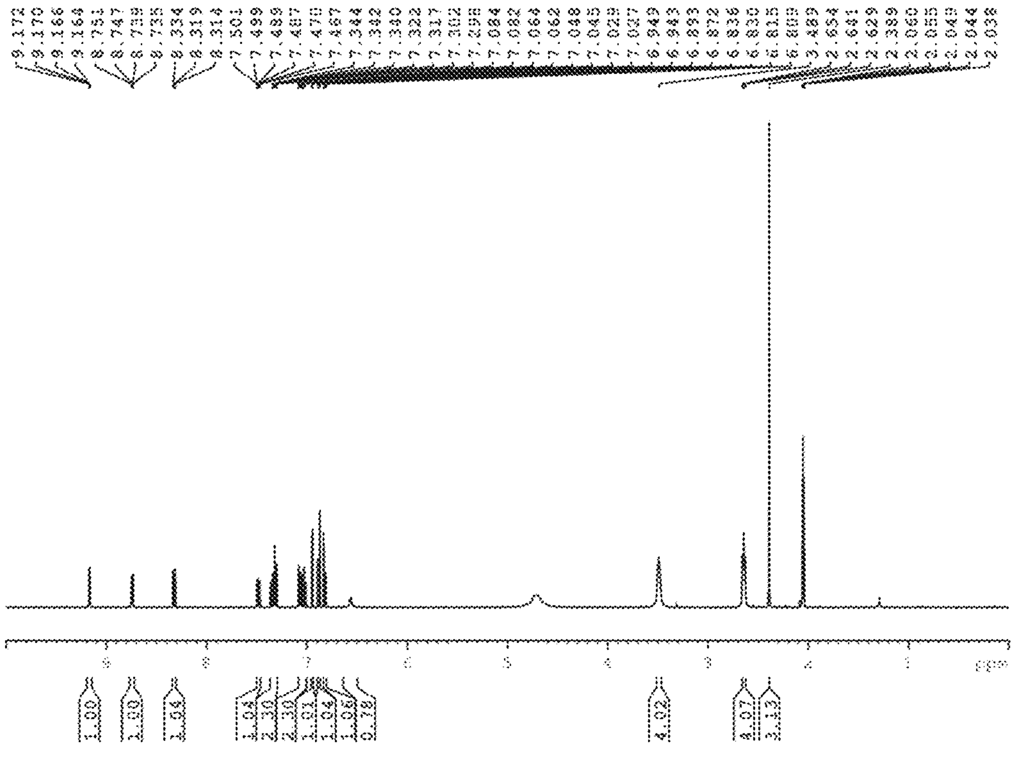

FIG. 9 shows a 1H-NMR spectrum of clozapine:nicotinic acid 1:1 salt.

Figure 10:
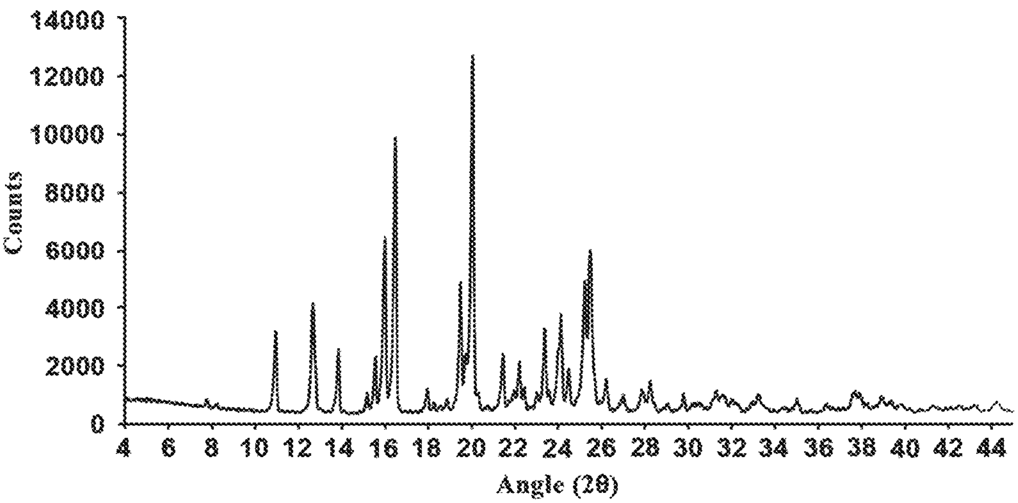

FIG. 10 shows a XRPD spectrum of clozapine:nicotinic acid 1:1 salt. Angle (2θ) peaks include 7.7; 8.2; 10.9; 12.6; 12.9; 13.8; 14.1; 15.1; 15.5; 16.0; 16.5; 17.9; 18.2; 18.5; 18.8; 19.5; 19.7; 20.0; 20.2; 20.7; 21.0; 21.4; 21.7; 21.9; 22.2; 22.4; 22.7; 23.0; 23.3; 23.5; 24.0; 24.1; 24.4; 25.2; 25.4; 25.6; 25.9; 26.2; 27.0; 27.8; 28.2; 28.4; 28.8; 29.0; 29.7; 30.1; 30.2; 30.4; 30.5; 31.2; 31.5; 31.6; 31.9; 32.0; 32.2; 32.8; 33.0; 33.2; 34.4; 35.0; 35.6; 36.3; 36.6; 37.0; 37.1; 37.6; 37.7; 37.9; 38.1; 38.2; 38.9; 39.0; 39.3; 39.8; 40.2; 40.7; 41.3; 41.8; 42.1; 42.5; 43.2; 44.1; and 44.2.

Figure 11:
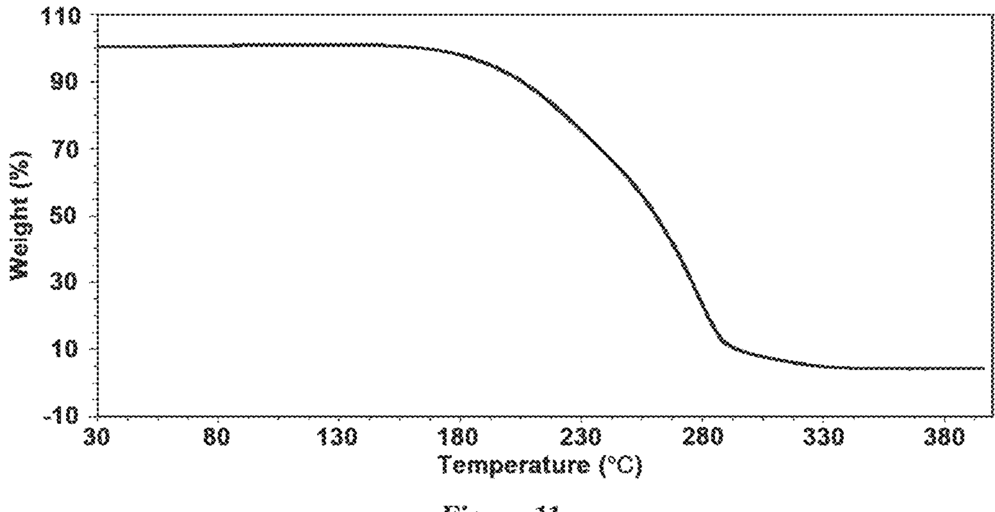

FIG. 11 shows a TGA spectrum of clozapine:nicotinic acid 1:1 salt.

Figure 12:
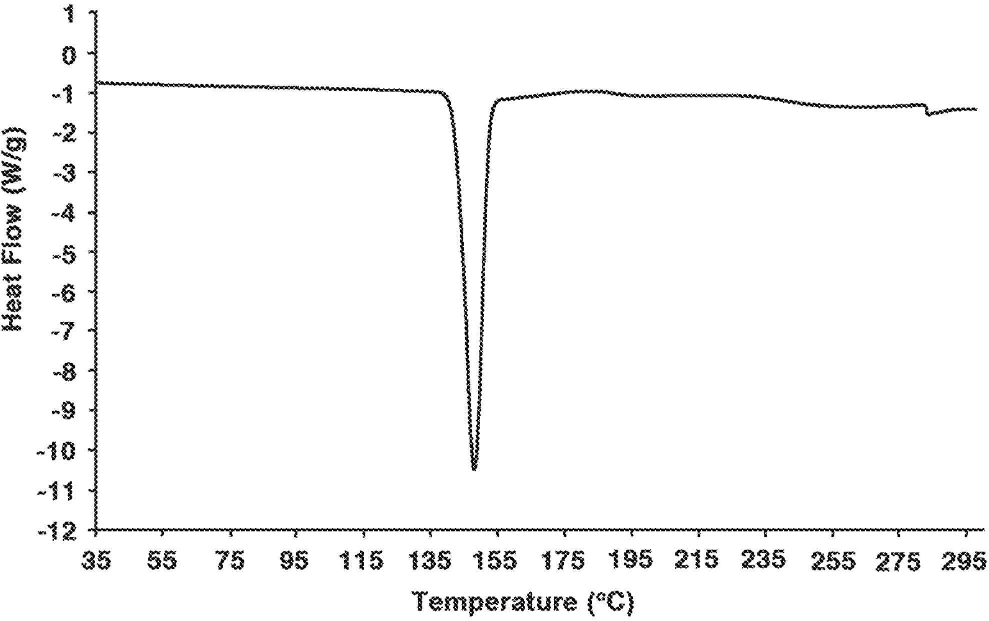

FIG. 12 shows a DSC spectrum of clozapine:nicotinic acid 1:1 salt.

Figure 13:
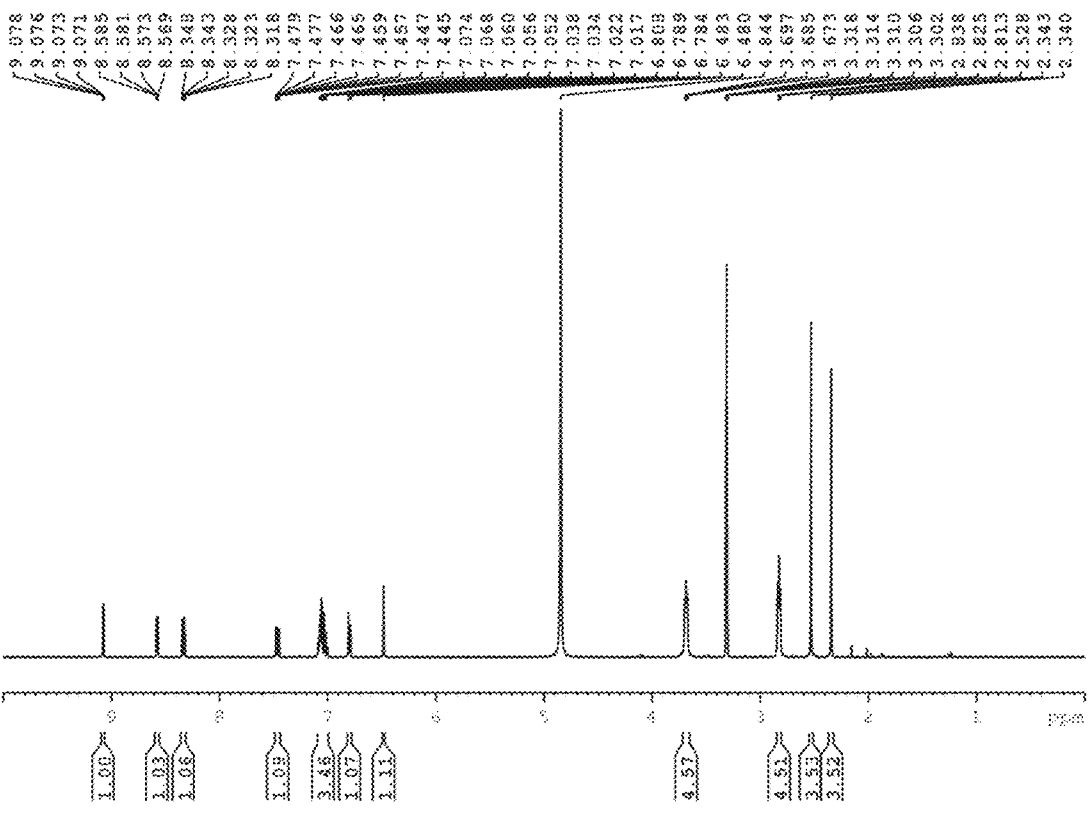

FIG. 13 shows a 1H-NMR spectrum of olanzapine:nicotinic acid 1:1 salt.

Figure 14:
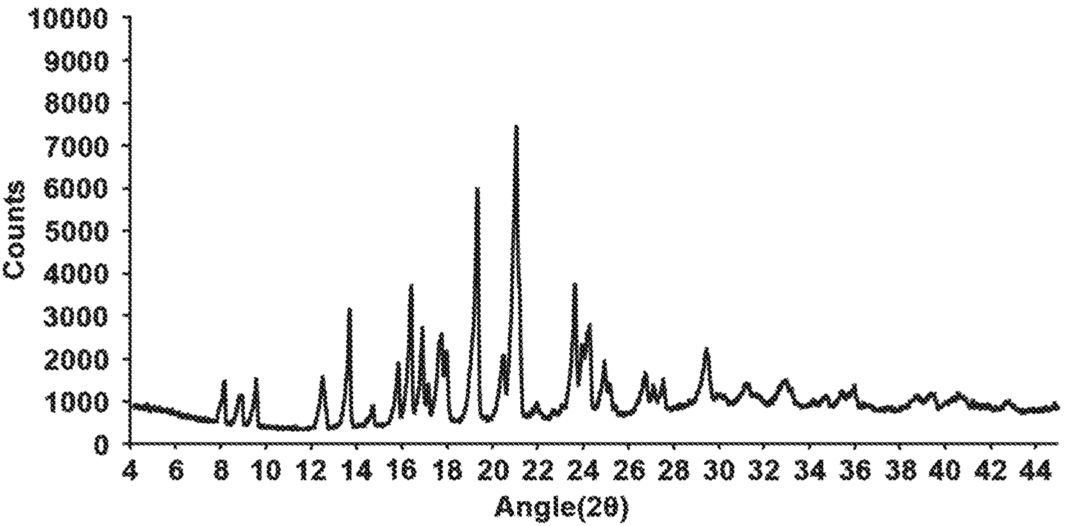

FIG. 14 shows a XRPD spectrum of olanzapine:nicotinic acid 1:1 salt. Angle (2θ) peaks include 7.9; 8.1; 8.8; 9.6; 12.5; 13.7; 14.4; 14.7; 15.8; 16.4; 16.6; 16.9; 17.2; 17.6; 17.7; 17.9; 19.3; 20.5; 21.1; 21.2; 21.9; 22.6; 23.0; 23.6; 23.9; 24.2; 24.3; 24.9; 25.2; 25.2; 26.7; 27.0; 27.1; 27.5; 29.4; 29.9; 30.2; 31.1; 31.6; 32.8; 33.1; 34.1; 34.6; 35.4; 35.9; 36.5; 38.7; 39.4; 40.5; and 42.7.

Figure 15:
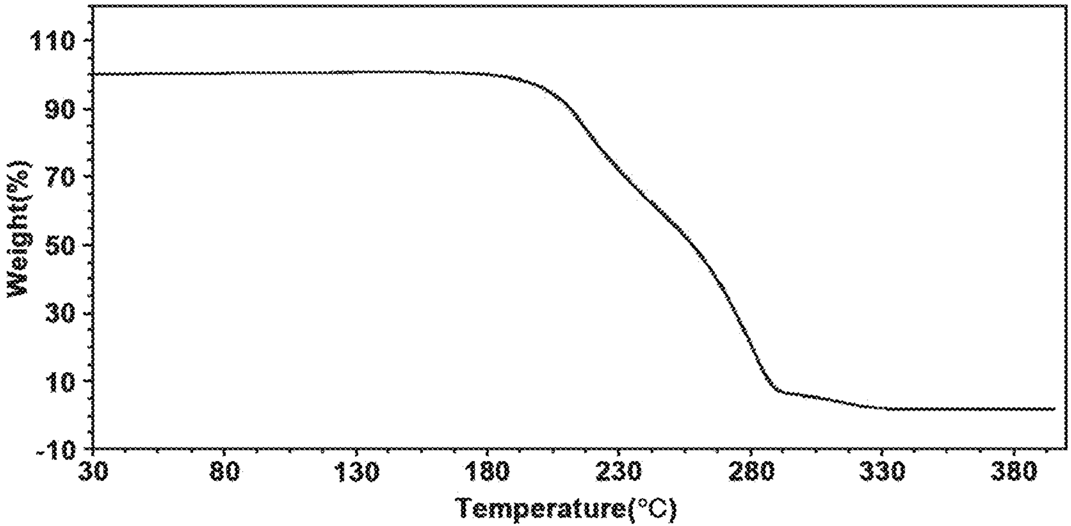

FIG. 15 shows a TGA spectrum of olanzapine:nicotinic acid 1:1 salt.

Figure 16:
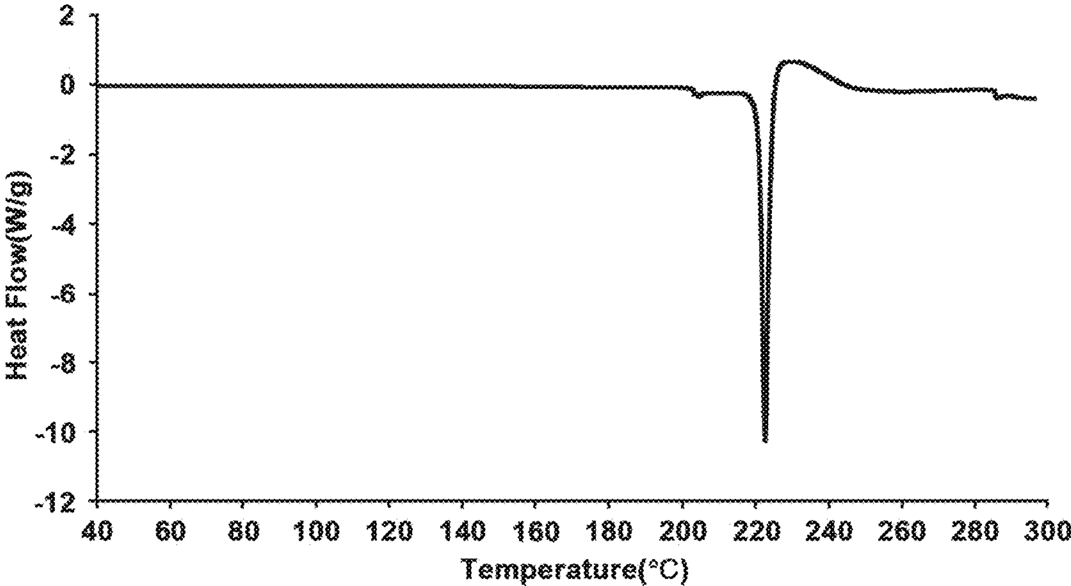

FIG. 16 shows a DSC spectrum of olanzapine:nicotinic acid 1:1 salt.

Figure 17:
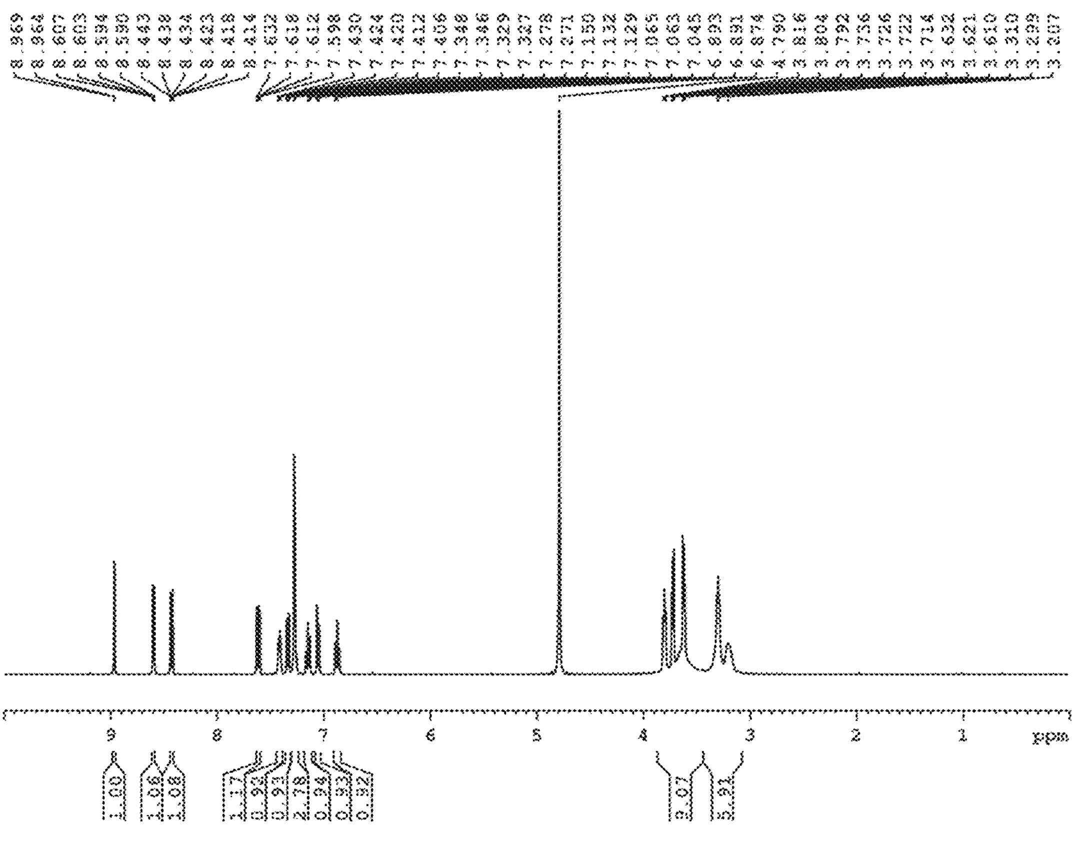

FIG. 17 shows a 1H-NMR spectrum of quetiapine:nicotinic acid 1:1 salt.

Figure 18:
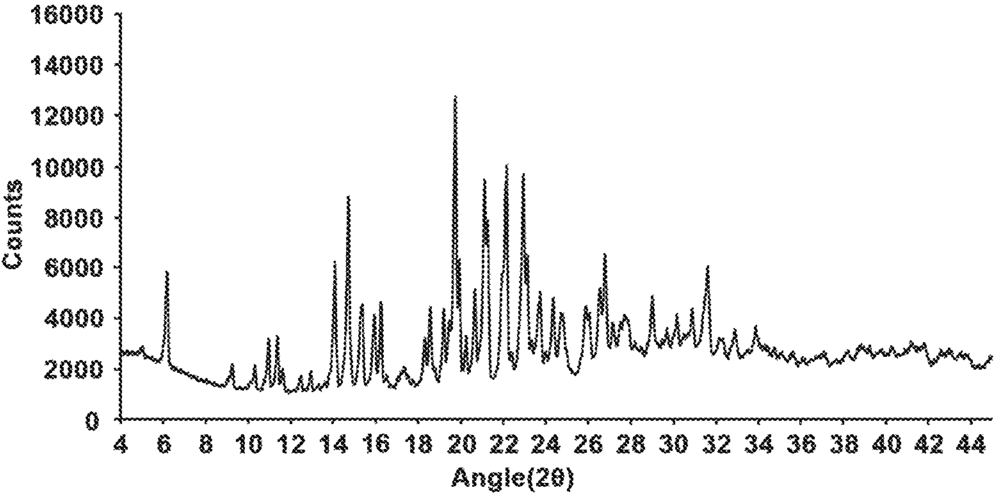

FIG. 18 shows a XRPD spectrum of quetiapine:nicotinic acid 1:1 salt. Angle (2θ) peaks include 5.0; 6.2; 9.0; 9.2; 10.0; 10.3; 10.7; 11.0; 11.4; 11.6; 12.4; 12.9; 13.3; 13.5; 13.8; 14.1; 14.7; 15.3; 15.9; 16.2; 16.5; 17.0; 17.2; 17.3; 17.5; 17.7; 18.3; 18.5; 18.7; 19.2; 19.4; 19.7; 19.9; 20.2; 20.6; 21.1; 21.3; 21.9; 22.1; 22.3; 23.0; 23.1; 23.3; 23.7; 24.0; 24.3; 24.7; 24.9; 25.9; 26.0; 26.5; 26.8; 27.1; 27.5; 27.7; 27.8; 28.1; 28.5; 29.0; 29.4; 29.7; 30.0; 30.2; 30.5; 30.9; 31.6; 32.2; 32.9; 33.4; 33.9; 34.2; 34.4; 34.7; 35.0; 35.6; 36.0; 36.6; 37.0; 37.6; 38.1; 38.7; 39.2; 39.7; 40.2; 41.2; 41.7; 42.6; 42.9; 43.5; 43.7; 43.9; and 44.9.

Figure 19:
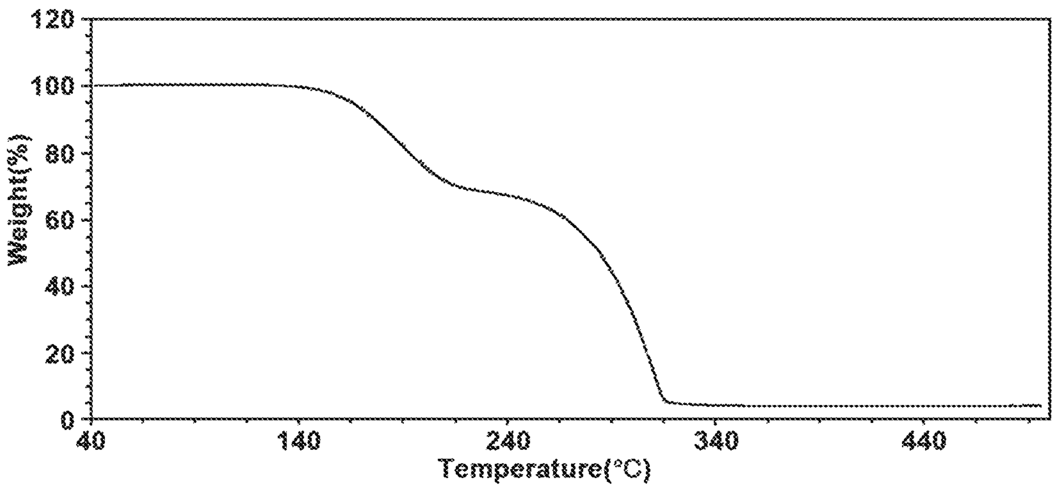

FIG. 19 shows a TGA spectrum of quetiapine:nicotinic acid 1:1 salt.

Figure 20:
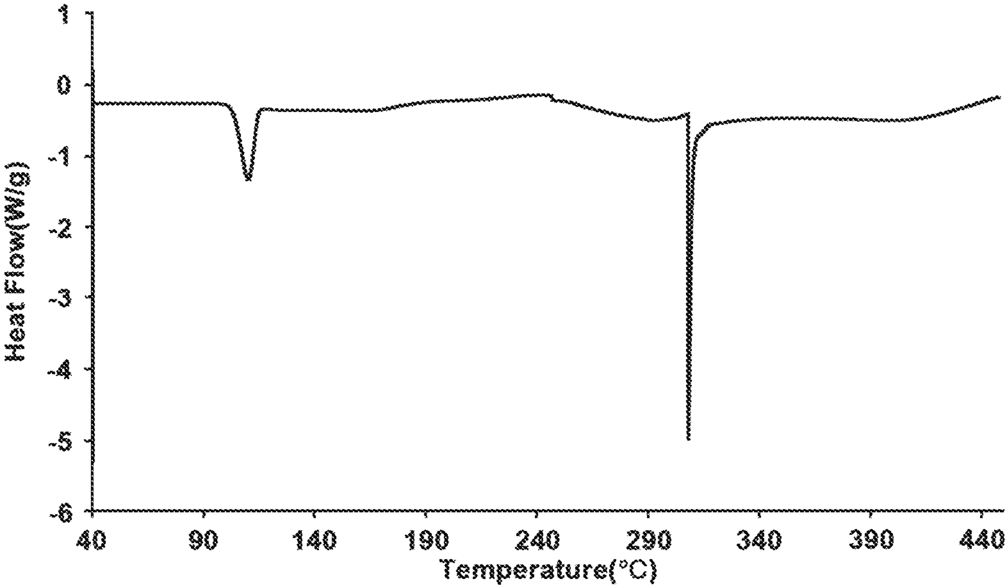

FIG. 20 shows a DSC spectrum of quetiapine:nicotinic acid 1:1 salt.

Figure 21:
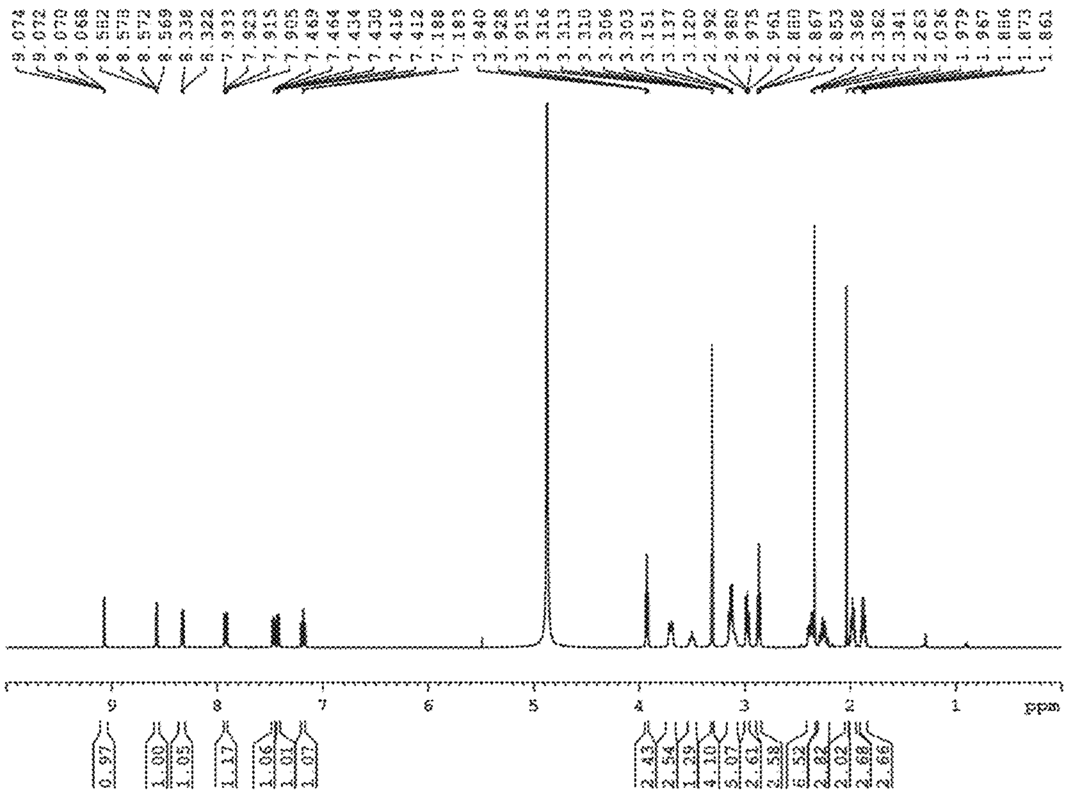

FIG. 21 shows a 1H-NMR spectrum of risperidone: nicotinic acid 1:1 salt.

Figure 22:
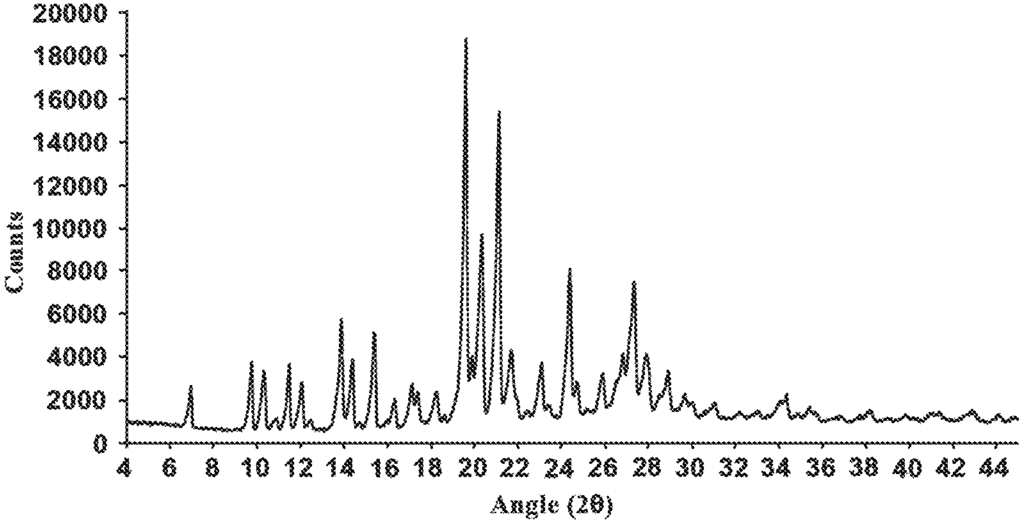

FIG. 22 shows a XRPD spectrum of risperidone:nicotinic acid 1:1 salt. Angle (2θ) peaks include 6.9; 9.7; 10.3; 10.9; 11.5; 12.0; 12.4; 13.9; 14.4; 14.7; 15.4; 16.0; 16.3; 17.1; 17.4; 18.2; 18.6; 19.6; 19.9; 20.3; 21.1; 21.7; 21.9; 22.4; 23.1; 23.4; 24.4; 24.7; 25.1; 25.8; 26.5; 26.8; 27.3; 27.9; 28.5; 28.9; 29.6; 31.0; 32.2; 33.0; 33.5; 34.1; 34.4; 34.8; 35.4; 35.6; 36.8; 37.7; 38.1; 39.0; 39.7; 40.9; 41.3; 42.8; 44.1; and 44.9.

Figure 23:
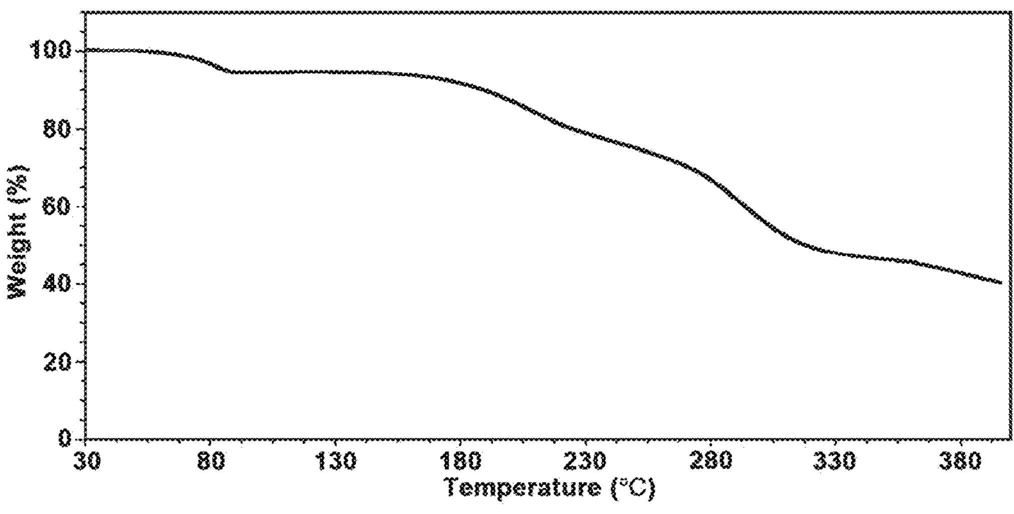

FIG. 23 shows a TGA spectrum of risperidone:nicotinic acid 1:1 salt.

Figure 24:
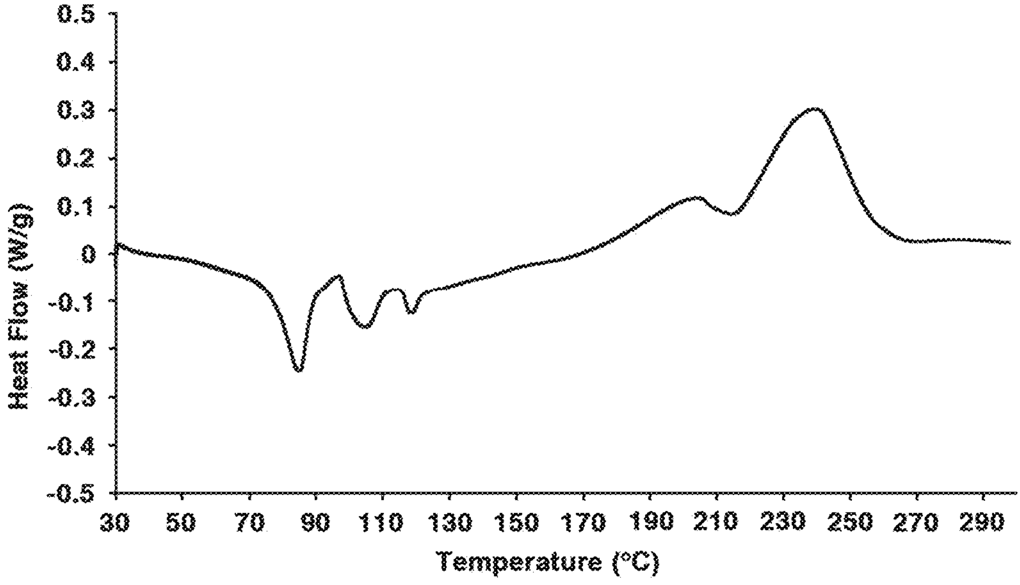

FIG. 24 shows a DSC spectrum of risperidone:nicotinic acid 1:1 salt.

Figure 25:
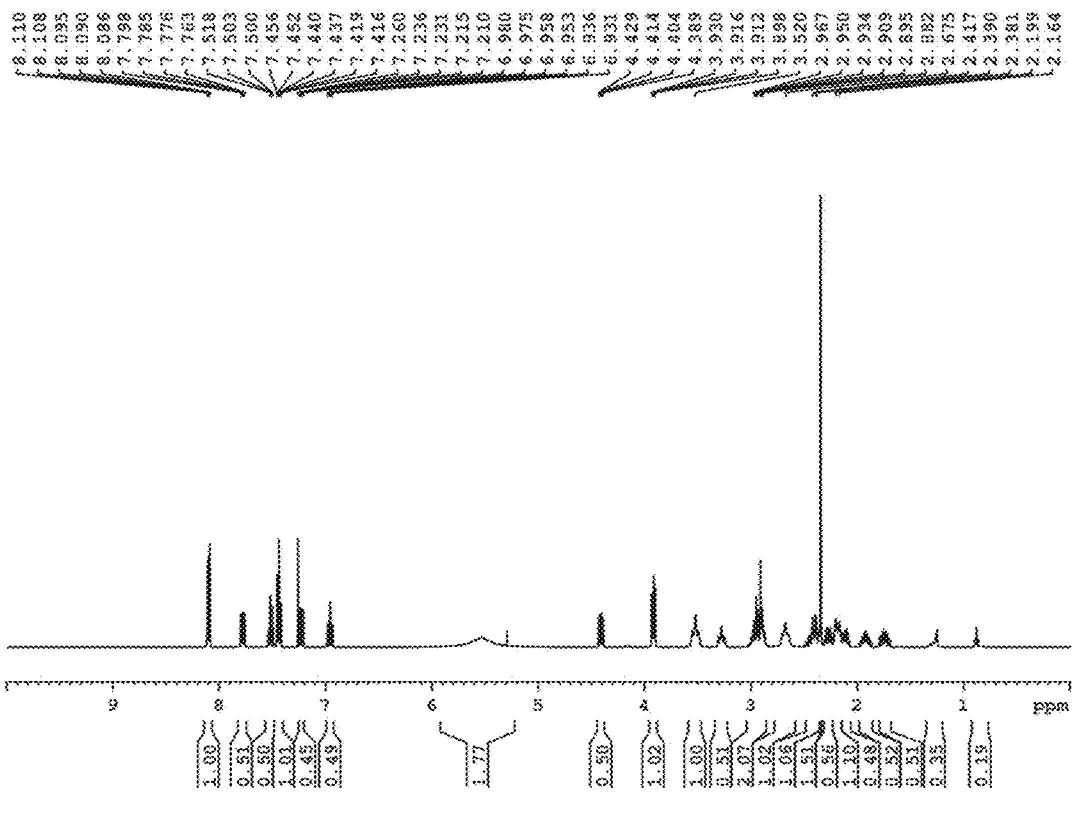

FIG. 25 shows a 1H-NMR spectrum of paliperidone: benzoic acid 1:1 salt.

Figure 26:
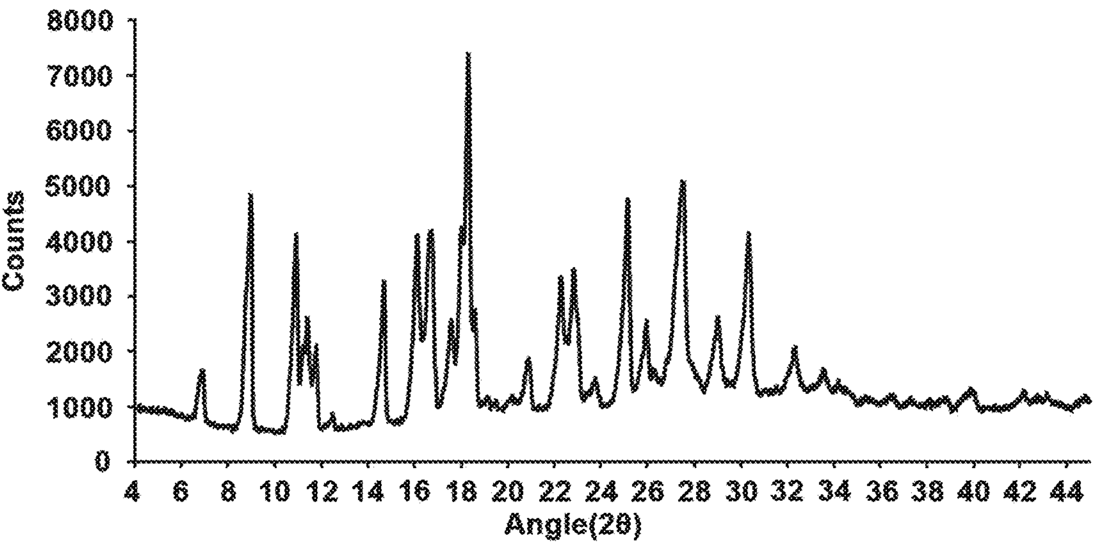

FIG. 26 shows a XRPD spectrum of paliperidone:benzoic acid 1:1 salt. Angle (2θ) peaks include 6.8; 9.0; 10.9; 11.2; 11.4; 11.8; 12.4; 13.7; 14.7; 16.1; 16.3; 16.6; 17.5; 18.0; 18.3; 18.6; 19.1; 19.4; 20.1; 20.8; 22.2; 22.4; 22.8; 23.3; 23.6; 25.1; 25.9; 26.2; 27.5; 27.8; 29.0; 30.3; 32.3; 33.5; 34.1; 35.3; 36.3; 37.2; 38.0; 38.7; 39.8; 42.0; 42.6; 43.1; and 44.9.

Figure 27:
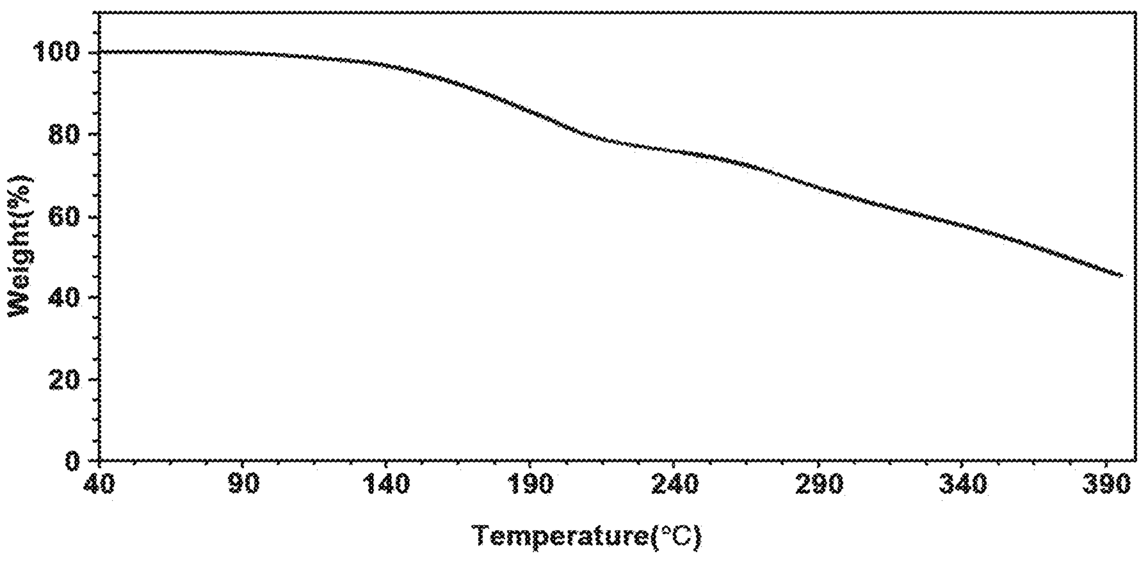

FIG. 27 shows a TGA spectrum of paliperidone:benzoic acid 1:1 salt.

Figure 28:
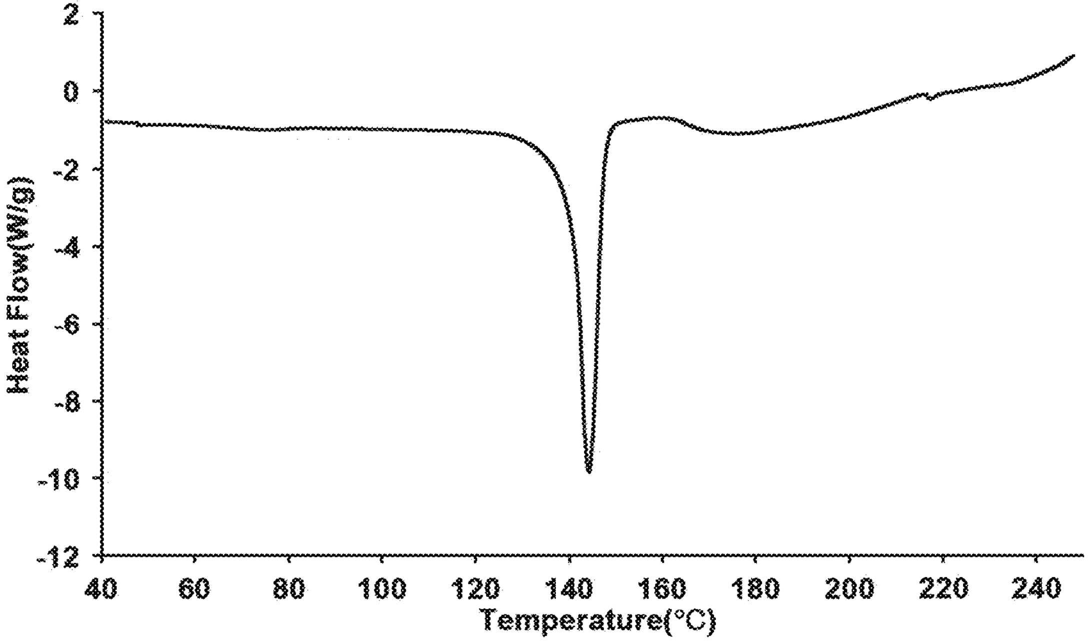

FIG. 28 shows a DSC spectrum of paliperidone:benzoic acid 1:1 salt.

Figure 29:
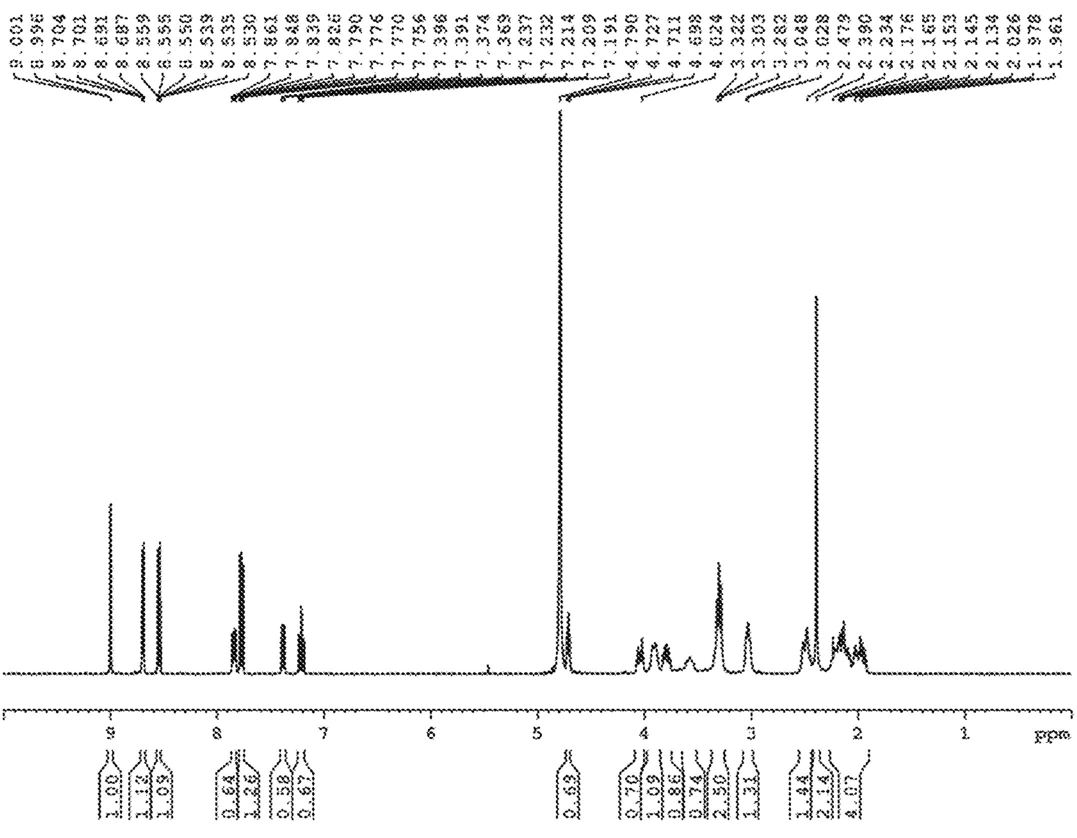

FIG. 29 shows a 1H-NMR spectrum of paliperidone: nicotinic acid 1:2 salt.

Figure 30:
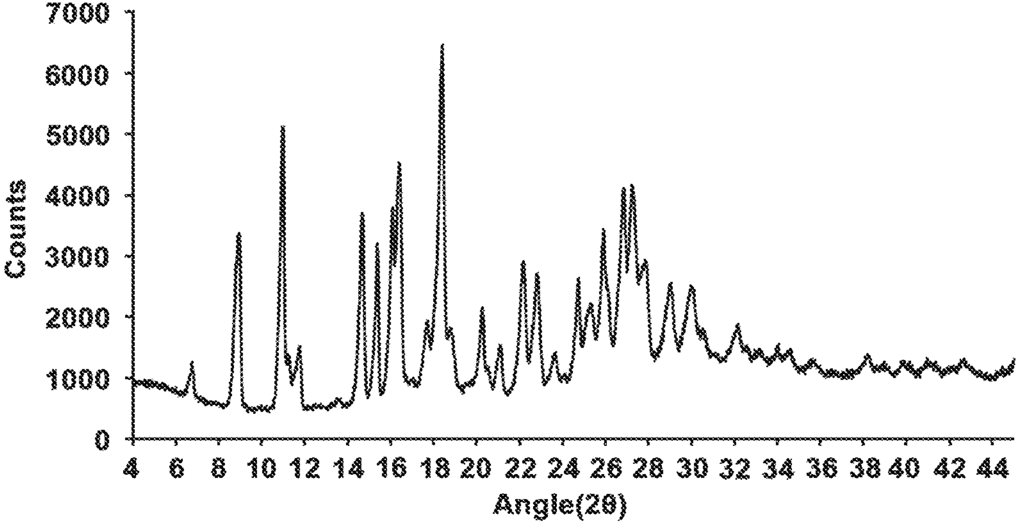

FIG. 30 shows a XRPD spectrum of paliperidone:nicotinic acid 1:2 salt. Angle (2θ) peaks include 6.7; 8.9; 11.0; 11.2; 11.7; 13.5; 14.7; 15.4; 16.1; 16.4; 16.9; 17.6; 18.4; 18.7; 20.2; 20.4; 21.0; 22.1; 22.8; 23.5; 23.9; 24.7; 25.2; 25.9; 26.1; 26.8; 27.2; 27.7; 29.0; 29.9; 30.4; 32.0; 32.5; 33.1; 33.9; 34.5; 35.5; 36.5; 38.1; 38.8; 39.7; 40.0; 40.9; 41.2; 42.0; 42.5; and 44.3.

Figure 31:
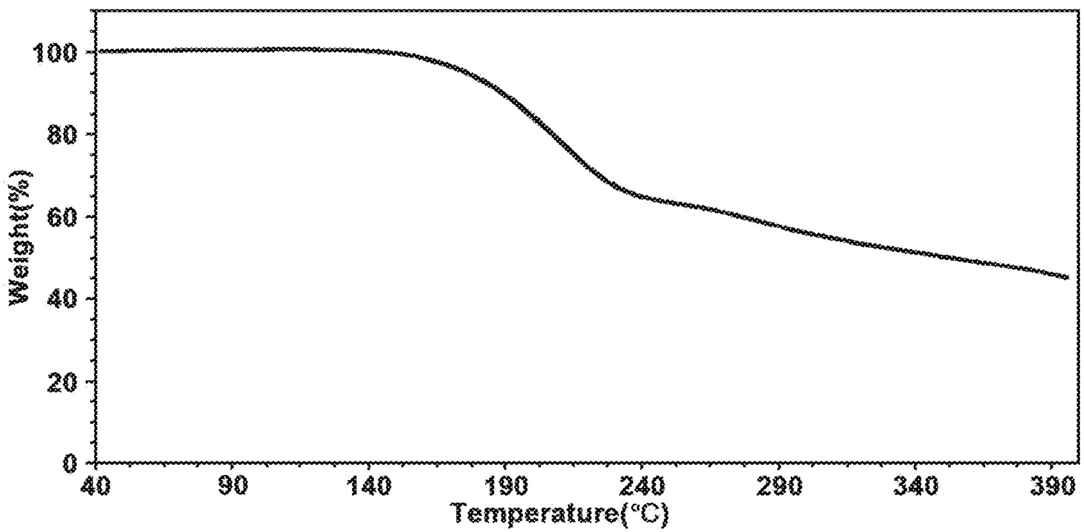

FIG. 31 shows a TGA spectrum of paliperidone:nicotinic acid 1:2 salt.

Figure 32:
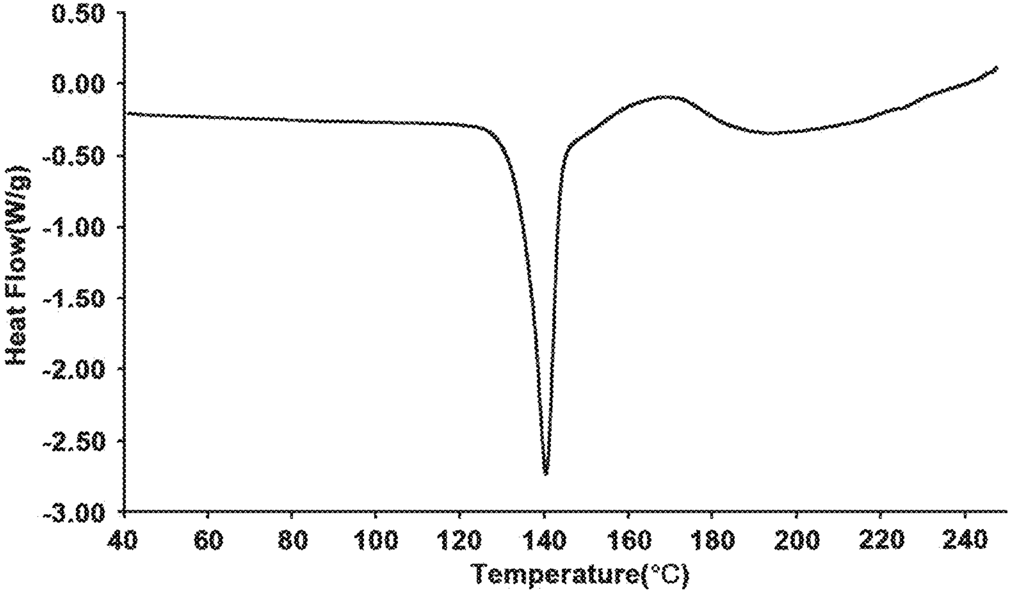

FIG. 32 shows a DSC spectrum of paliperidone:nicotinic acid 1:2 salt.

Figure 33:
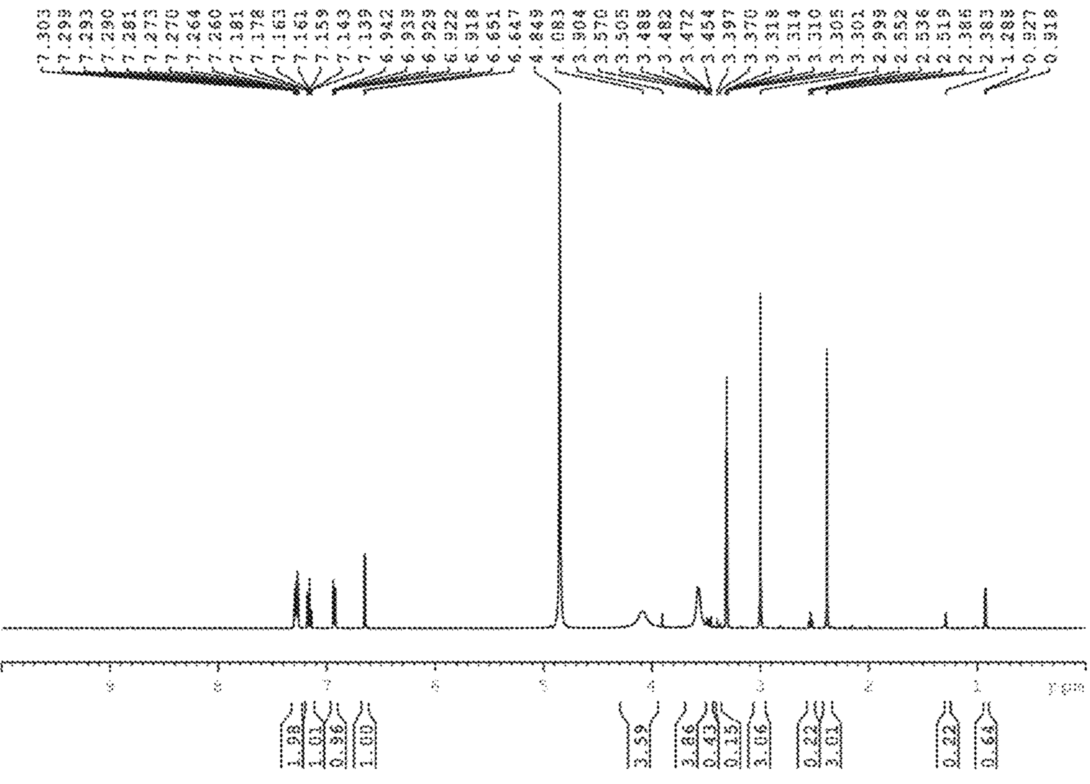

FIG. 33 shows a 1H-NMR spectrum of olanzapine:pantothenic acid 5:1 salt.

Figure 34:
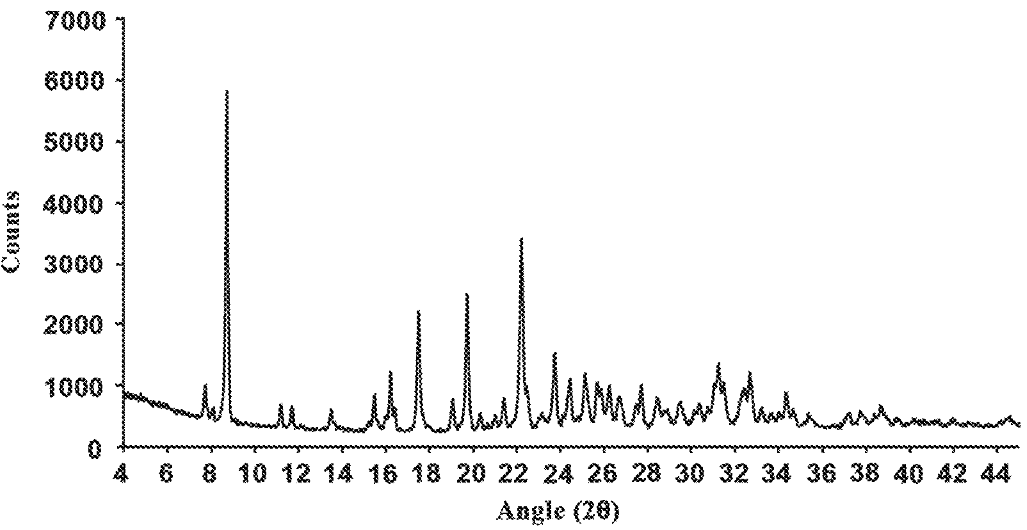

FIG. 34 show a XRPD spectrum of olanzapine:pantothenic acid 5:1 salt. Angle (2θ) peaks include 7.7; 7.8; 8.1; 8.7; 11.2; 11.7; 12.1; 13.5; 15.2; 15.4; 16.0; 16.2; 16.4; 17.5; 18.0; 19.0; 19.7; 20.3; 20.6; 21.0; 21.4; 22.2; 22.4; 23.1; 23.7; 24.1; 24.4; 24.8; 25.1; 25.7; 25.8; 26.2; 26.7; 27.4; 27.7; 28.4; 28.8; 29.4; 30.1; 30.3; 30.7; 31.0; 31.2; 31.4; 32.3; 32.6; 33.2; 33.6; 33.9; 34.3; 34.6; 35.3; 37.1; 37.7; 38.3; 38.6; 39.4; 40.1; 41.2; 42.0; 42.7; 43.0; 44.1; and 44.5.

Figure 35:
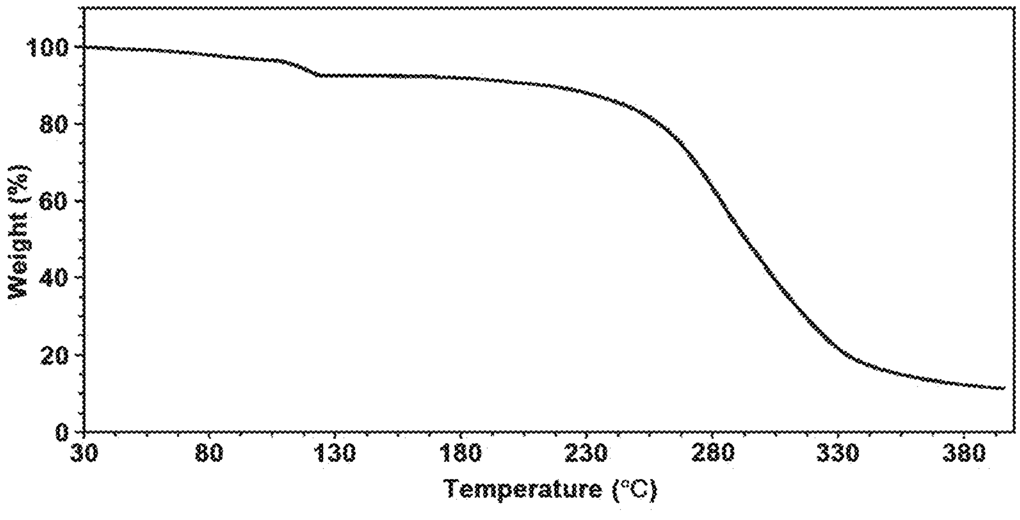

FIG. 35 shows a TGA spectrum of olanzapine:pantothenic acid 5:1 salt.

Figure 36:
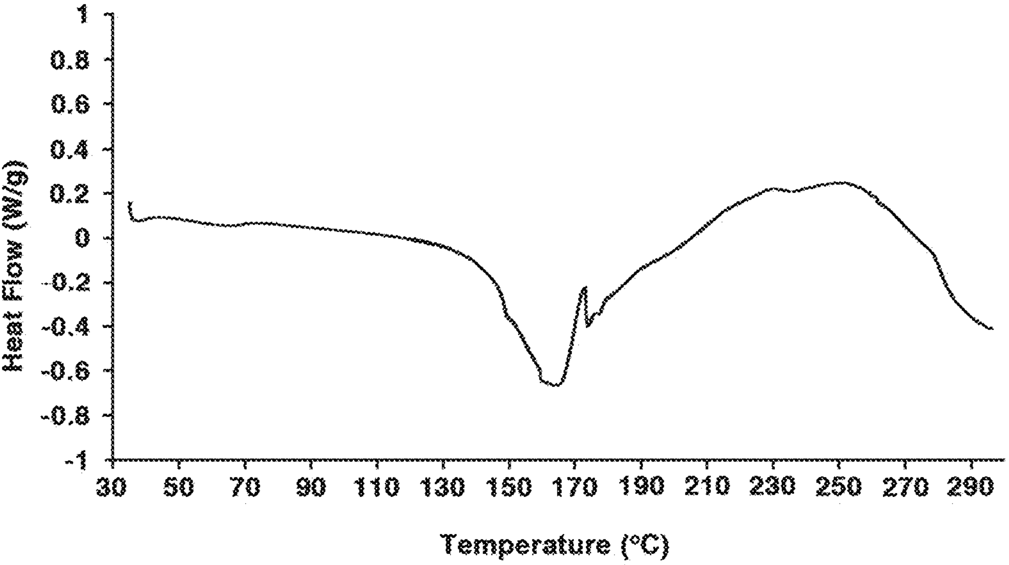

FIG. 36 shows a DSC spectrum of olanzapine:pantothenic acid 5:1 salt.

Figure 37:
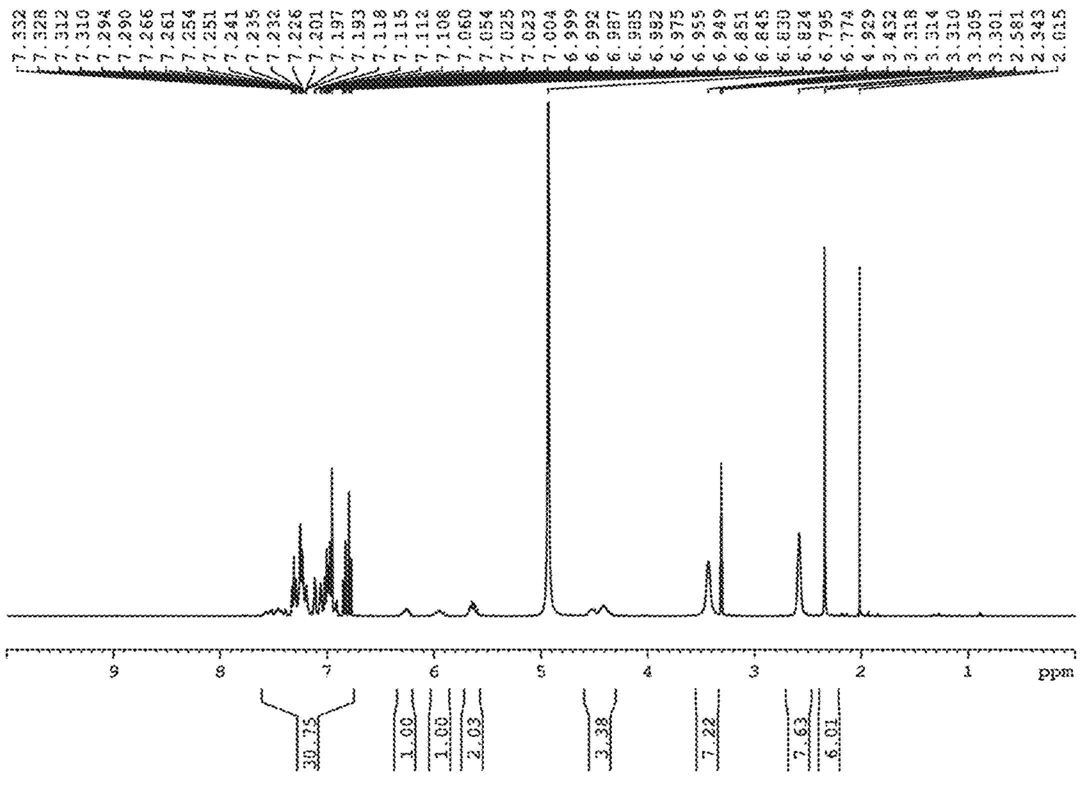

FIG. 37 shows a 1H-NMR spectrum of clozapine:enriched tannic acid 2:1 salt.

Figure 38:
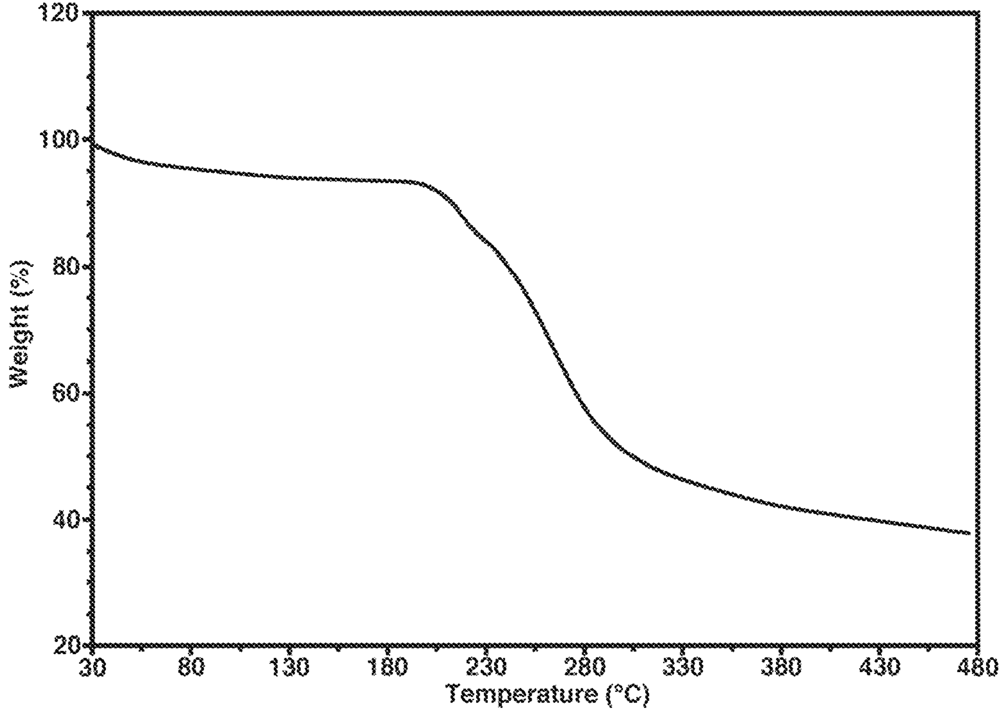

FIG. 38 shows a TGA spectrum of clozapine:enriched tannic acid 2:1 salt.

Figure 39:
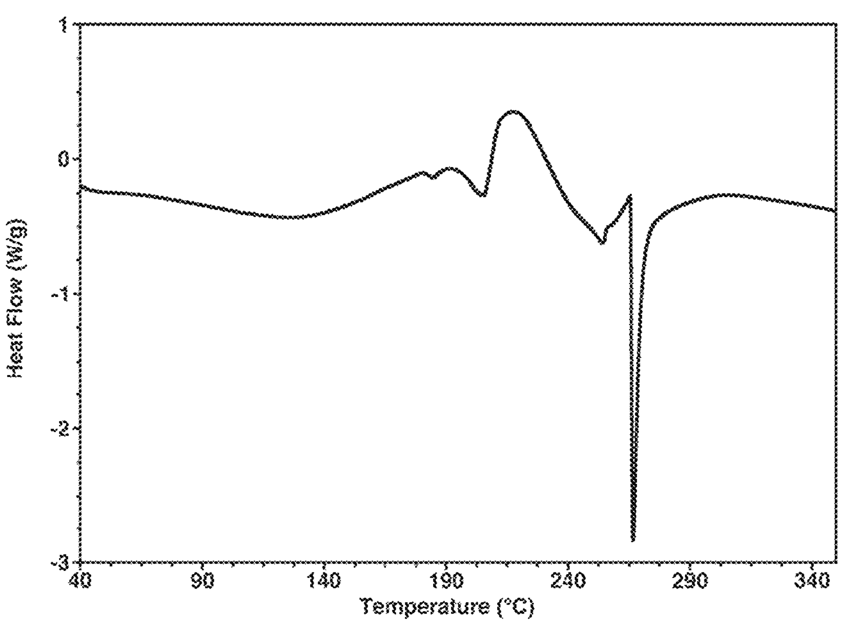

FIG. 39 shows a DSC spectrum of clozapine:enriched tannic acid 2:1 salt.

Figure 40:
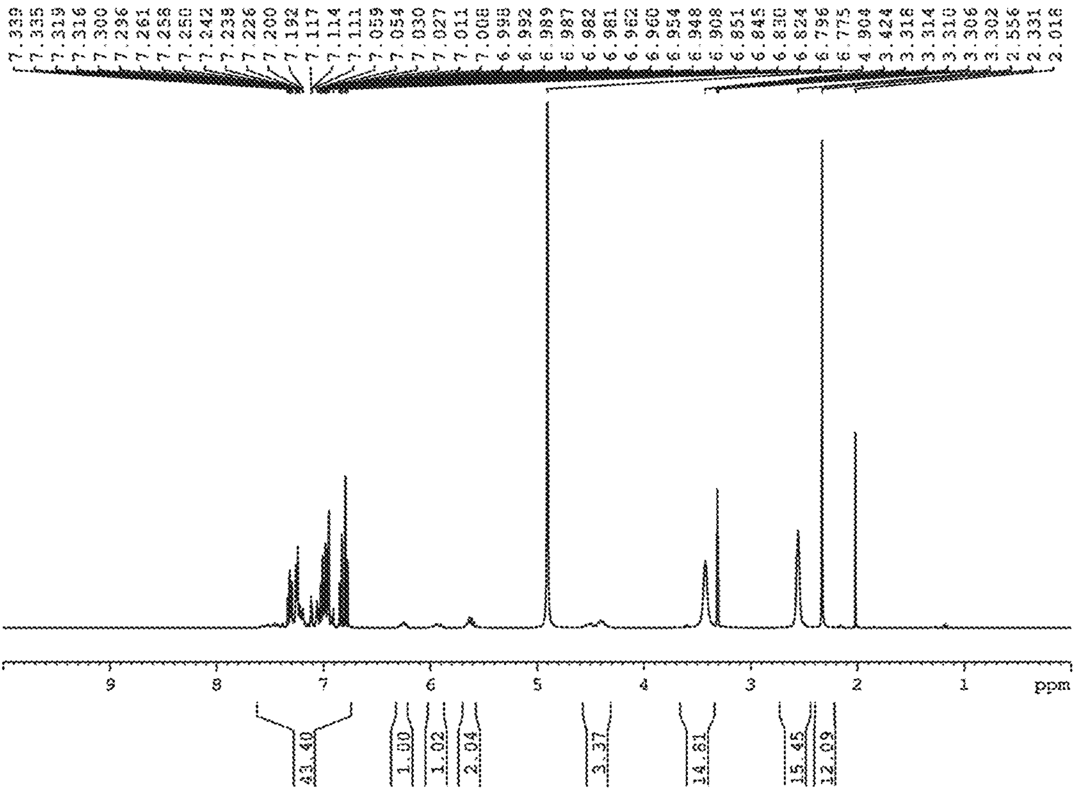

FIG. 40 shows a 1H-NMR spectrum of clozapine:enriched tannic acid 4:1 salt.

Figure 41:
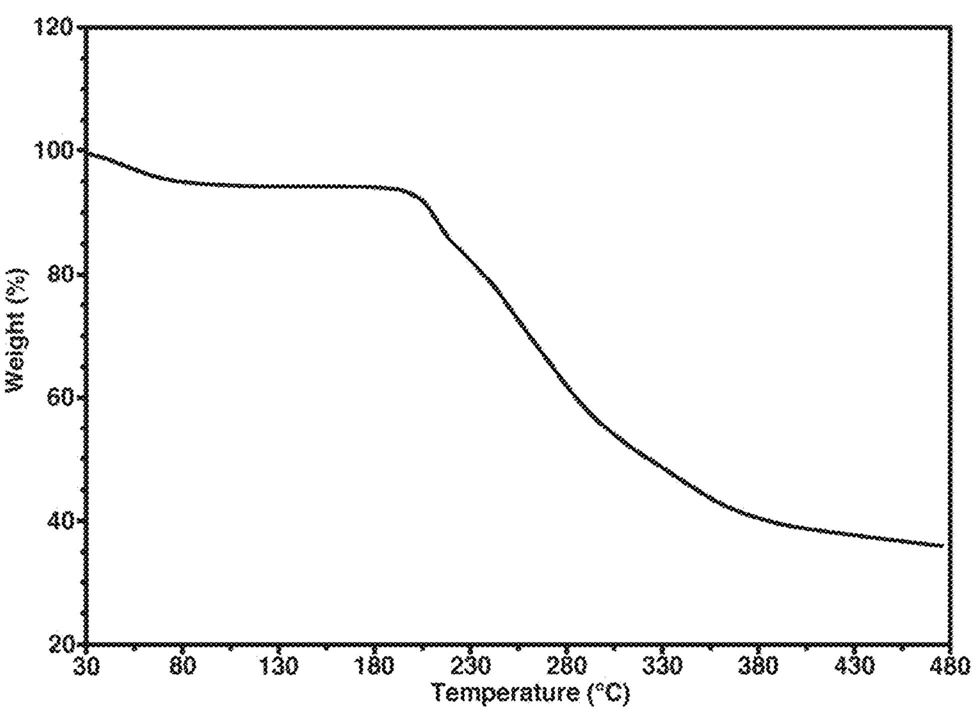

FIG. 41 shows a TGA spectrum of clozapine:enriched tannic acid 4:1 salt.

Figure 42:
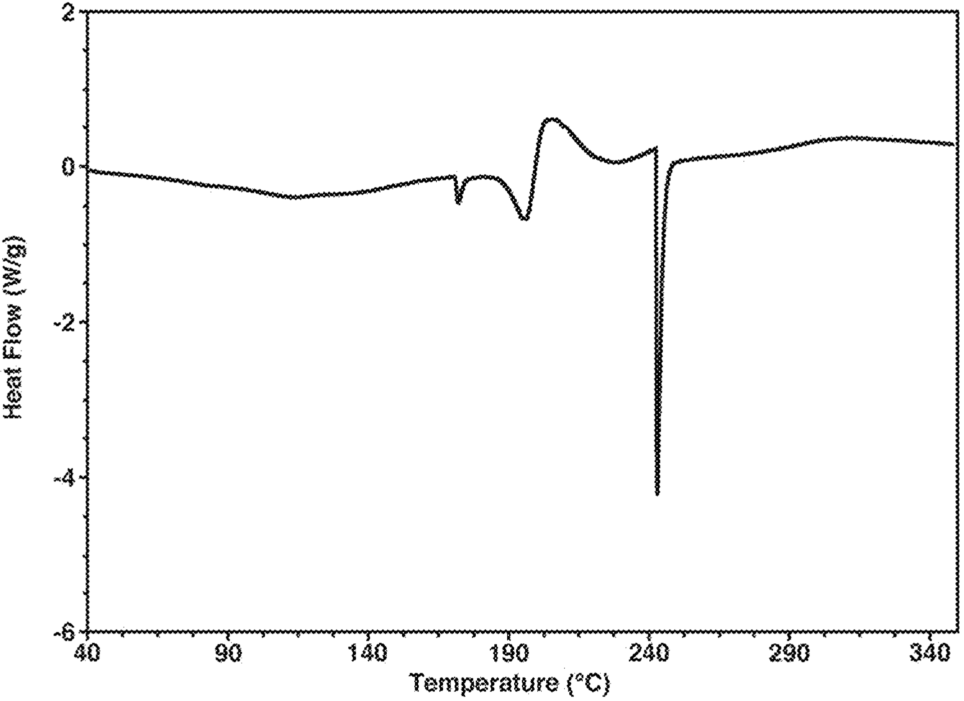

FIG. 42 shows a DSC spectrum of clozapine:enriched tannic acid 4:1 salt.

Figure 43:
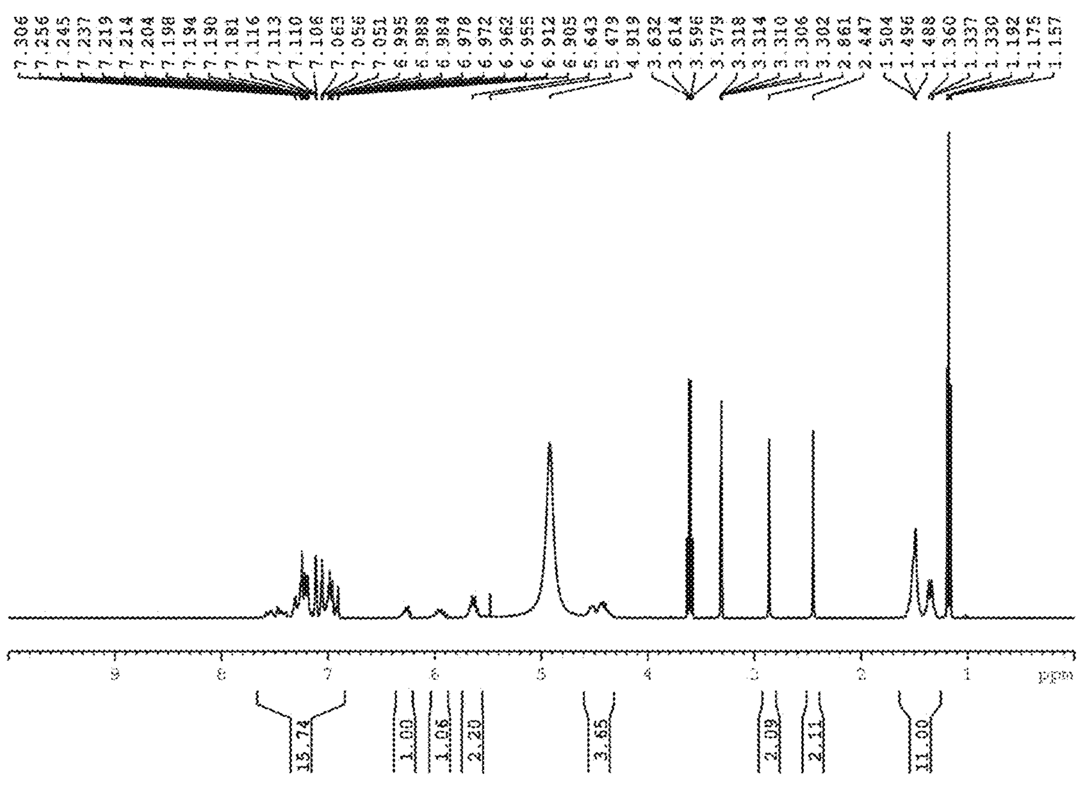

FIG. 43 shows a 1H-NMR spectrum of gabapentin:enriched tannic acid 1:1 salt.

Figure 44:
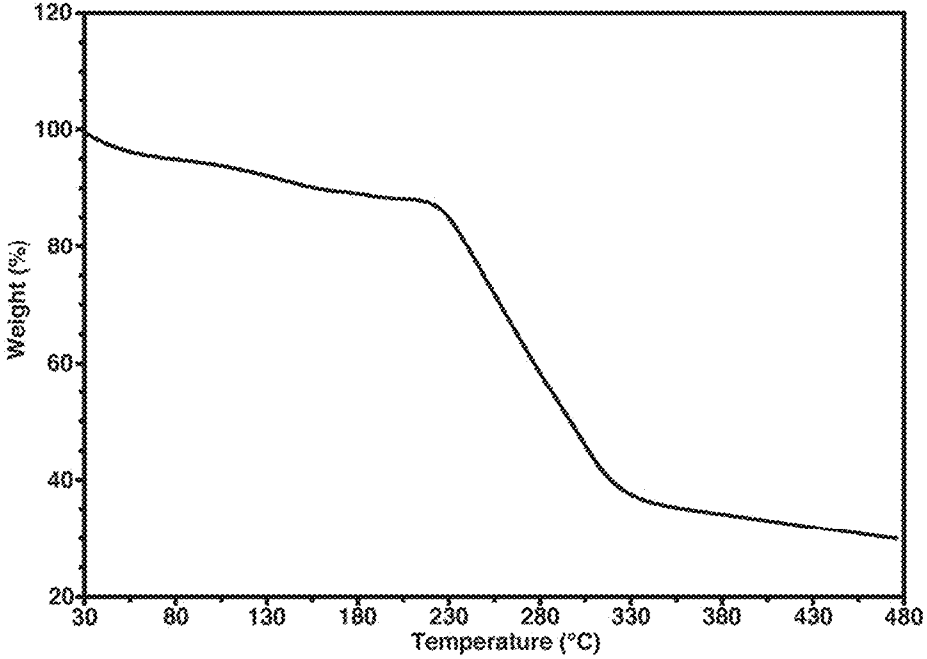

FIG. 44 shows a TGA spectrum of gabapentin:enriched tannic acid 1:1 salt.

Figure 45:
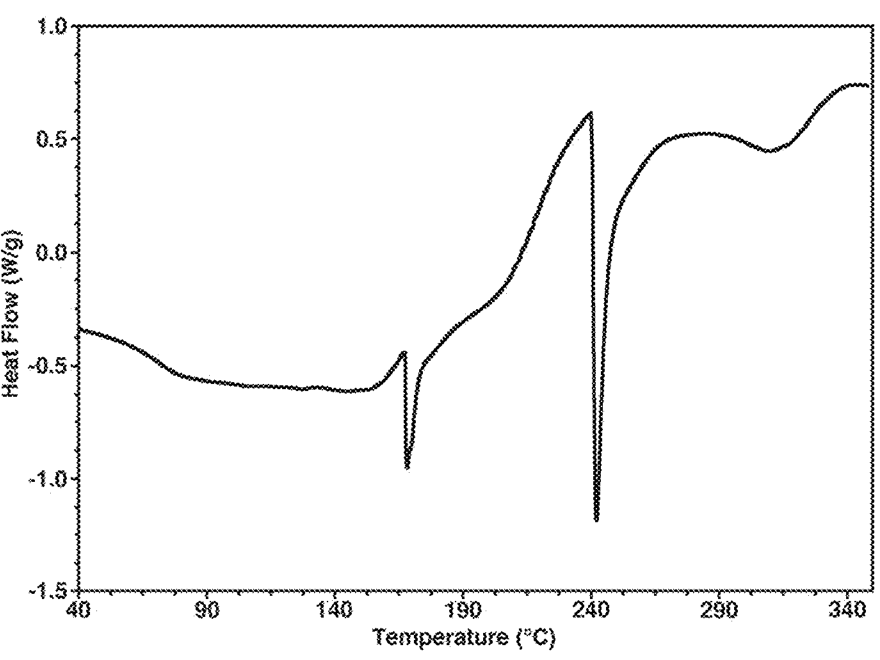

FIG. 45 shows a DSC spectrum of gabapentin:enriched tannic acid 1:1 salt.

Figure 46:
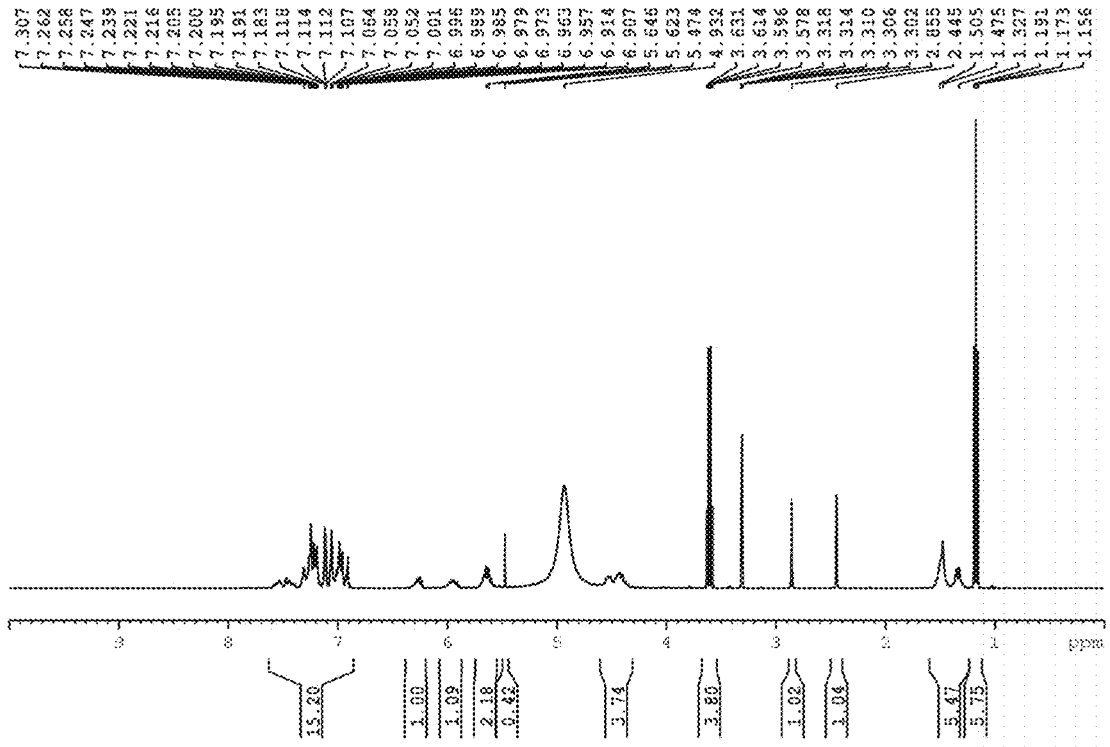

FIG. 46 shows a 1H-NMR spectrum of gabapentin:enriched tannic acid 1:2 salt.

Figure 47:
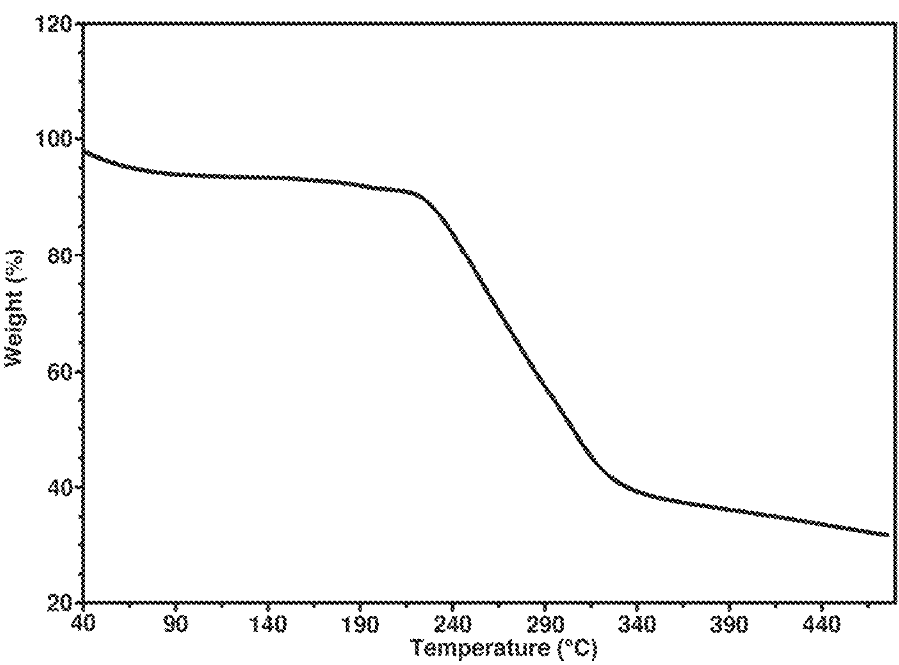

FIG. 47 shows a TGA spectrum of gabapentin:enriched tannic acid 1:2 salt.

Figure 48:
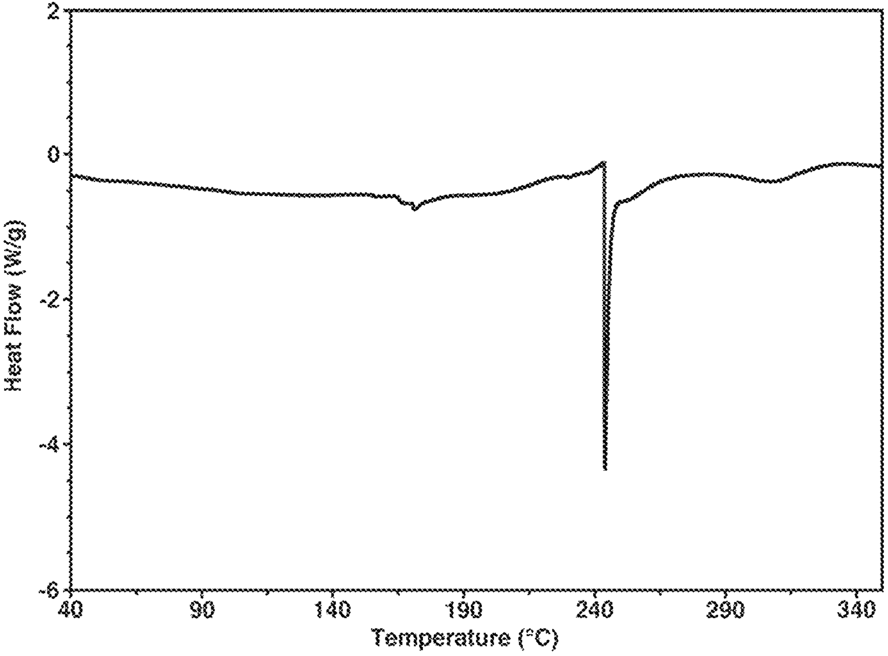

FIG. 48 shows a DSC spectrum of gabapentin:enriched tannic acid 1:2 salt.

Figure 49:
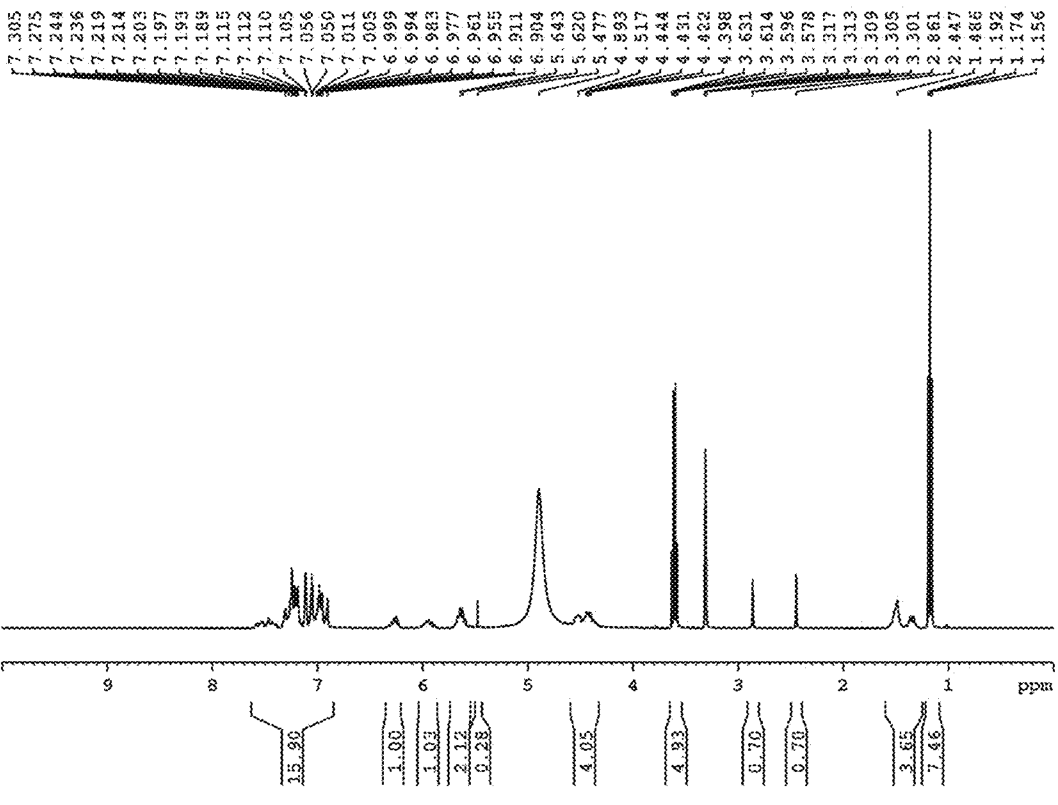

FIG. 49 shows a 1H-NMR spectrum of gabapentin:enriched tannic acid 1:3 salt.

Figure 50:
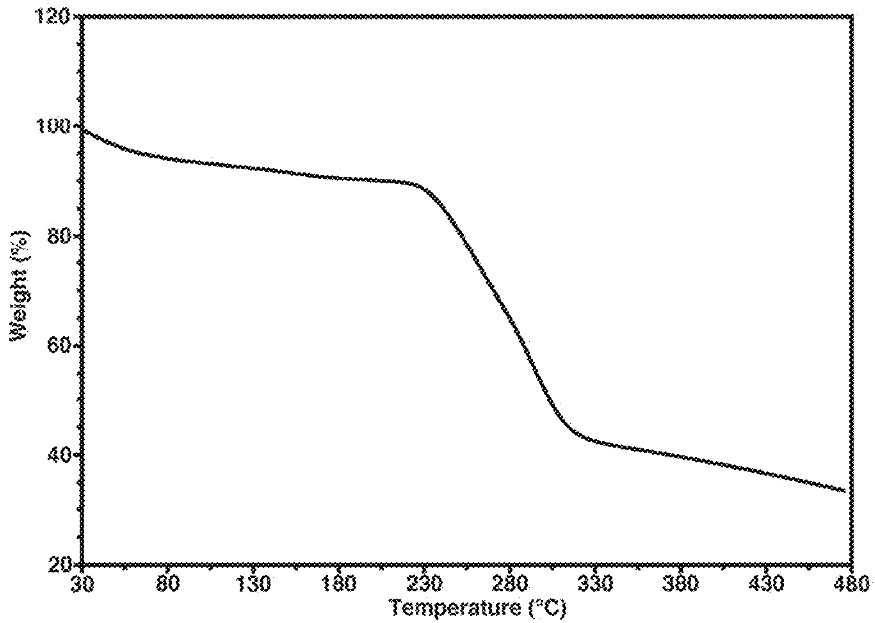

FIG. 50 shows a TGA spectrum of gabapentin:enriched tannic acid 1:3 salt.

Figure 51:
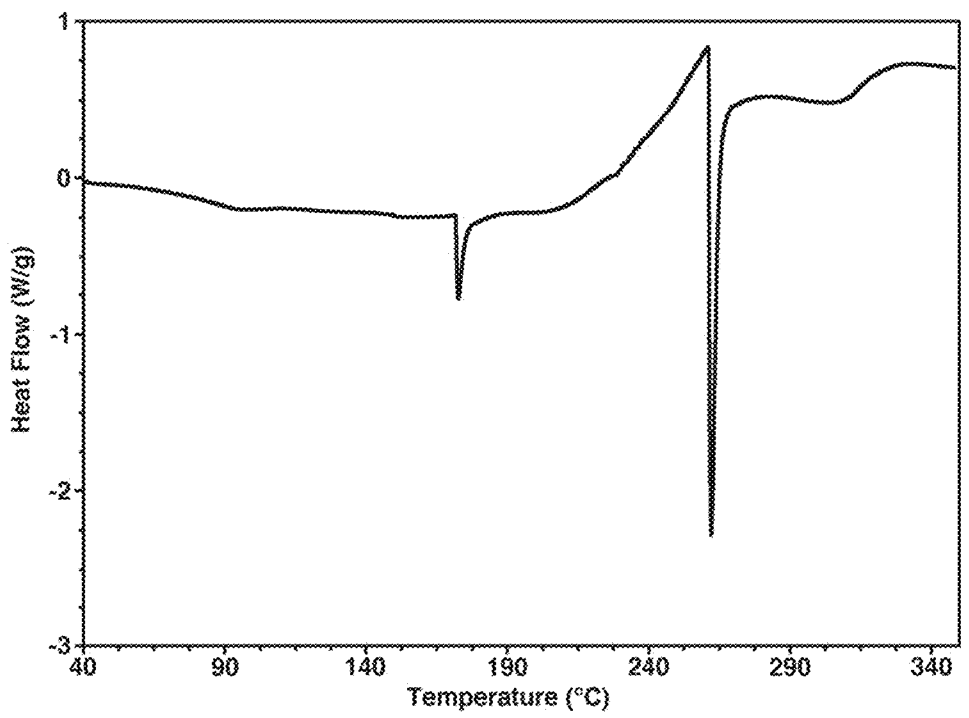

FIG. 51 shows a DSC spectrum of gabapentin:enriched tannic acid 1:3 salt.

Figure 52:
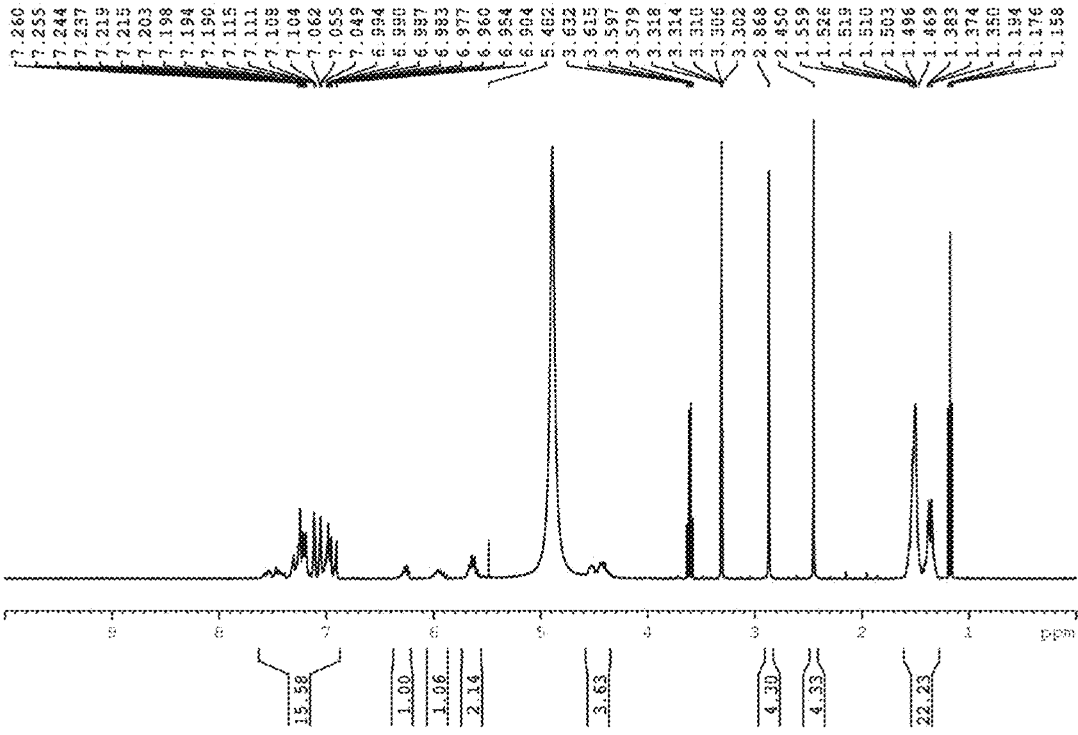

FIG. 52 shows a 1H-NMR spectrum of gabapentin:enriched tannic acid 2:1 salt.

Figure 53:
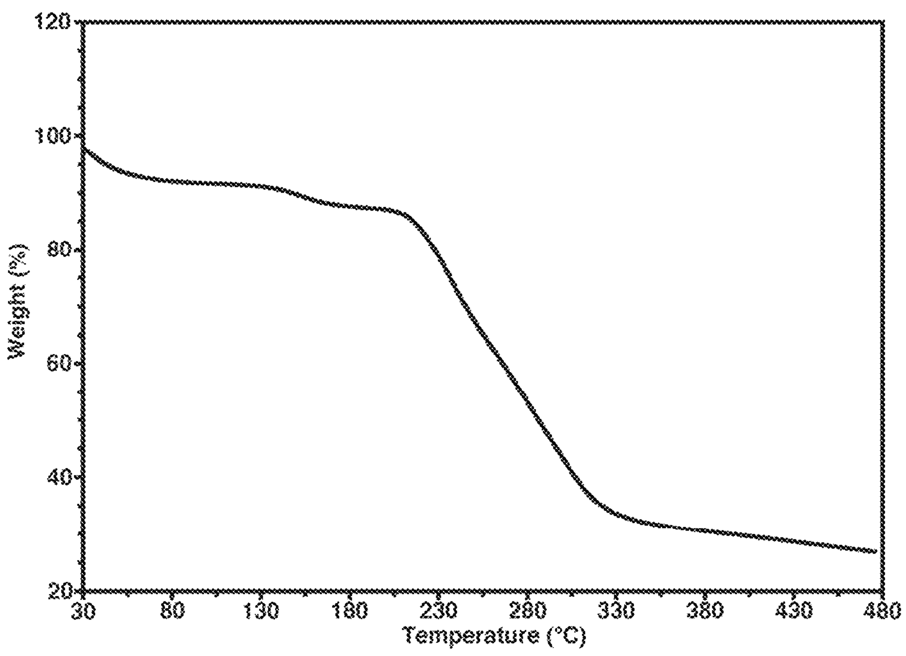

FIG. 53 shows a TGA spectrum of gabapentin:enriched tannic acid 2:1 salt.

Figure 54:
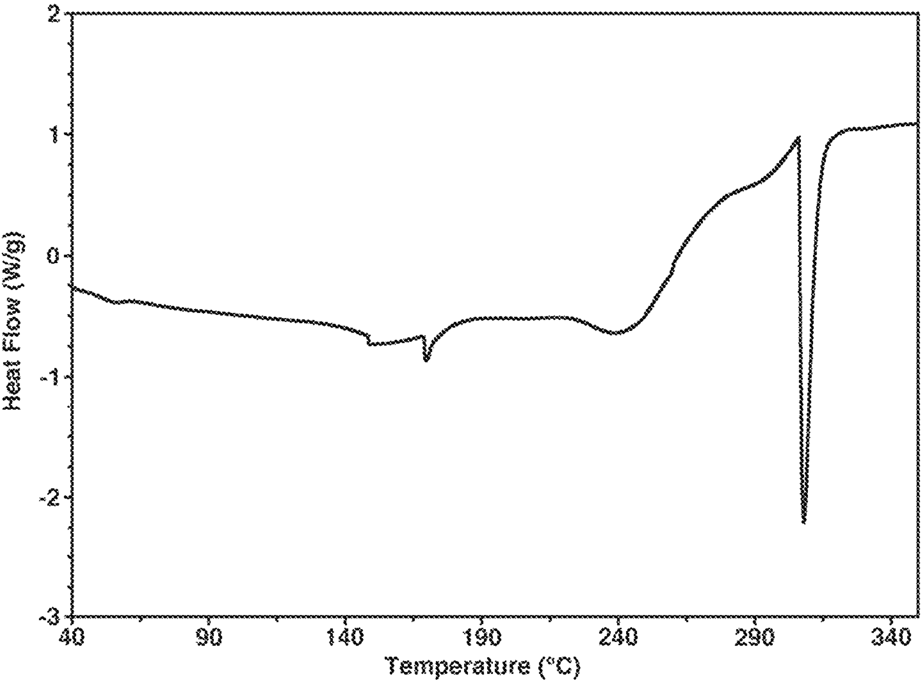

FIG. 54 shows a DSC spectrum of gabapentin:enriched tannic acid 2:1 salt.

Figure 55:
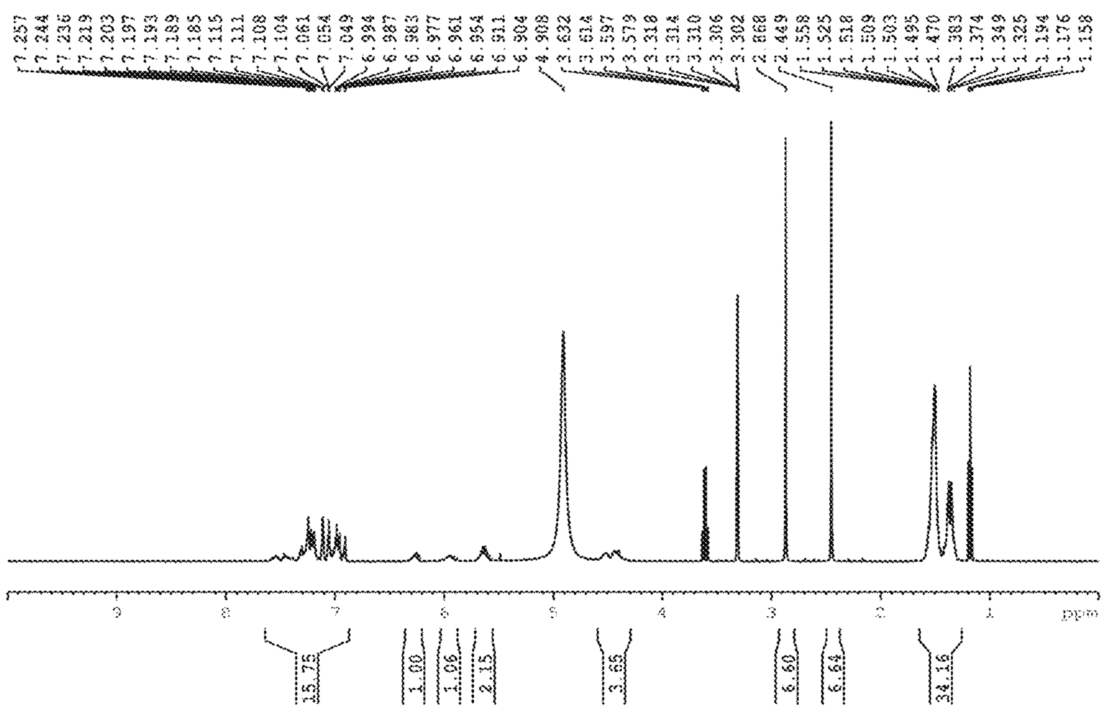

FIG. 55 shows a 1H-NMR spectrum of gabapentin:enriched tannic acid 3:1 salt.

Figure 56:
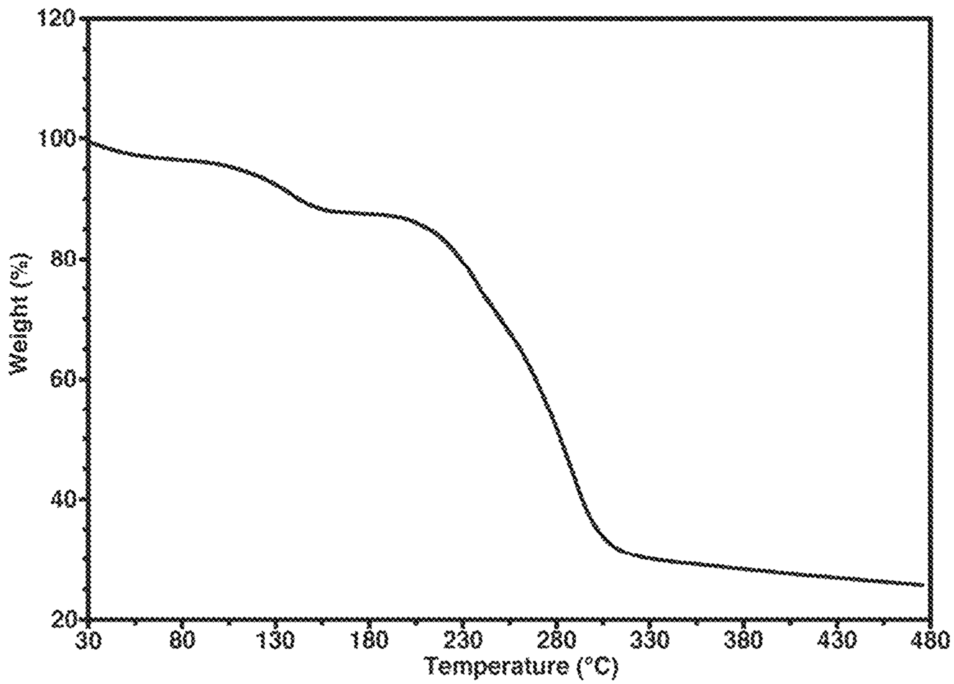

FIG. 56 shows a TGA spectrum of gabapentin:enriched tannic acid 3:1 salt.

Figure 57:
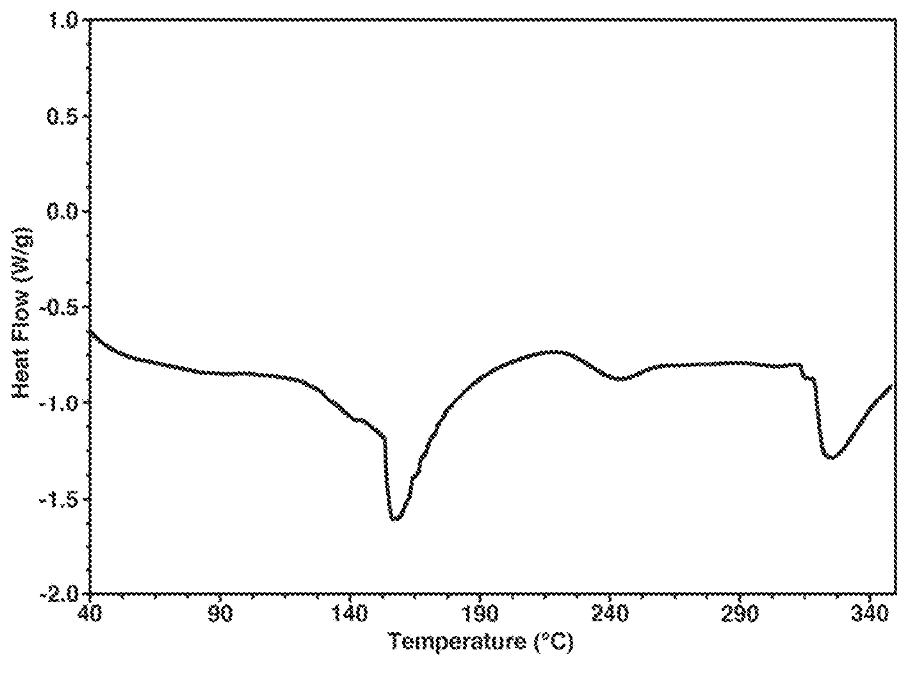

FIG. 57 shows a DSC spectrum of gabapentin:enriched tannic acid 3:1 salt.

Figure 58:
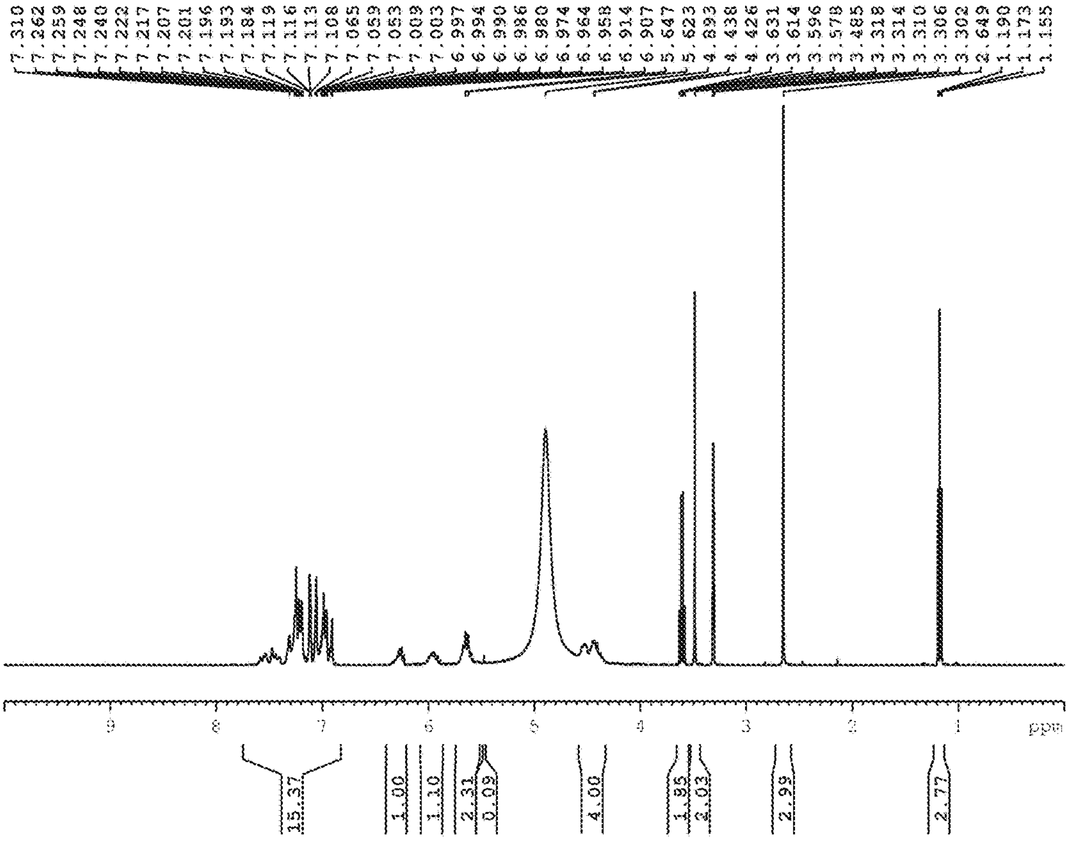

FIG. 58 shows a 1H-NMR spectrum of sarcosine:enriched tannic acid 1:1 salt.

Figure 59:
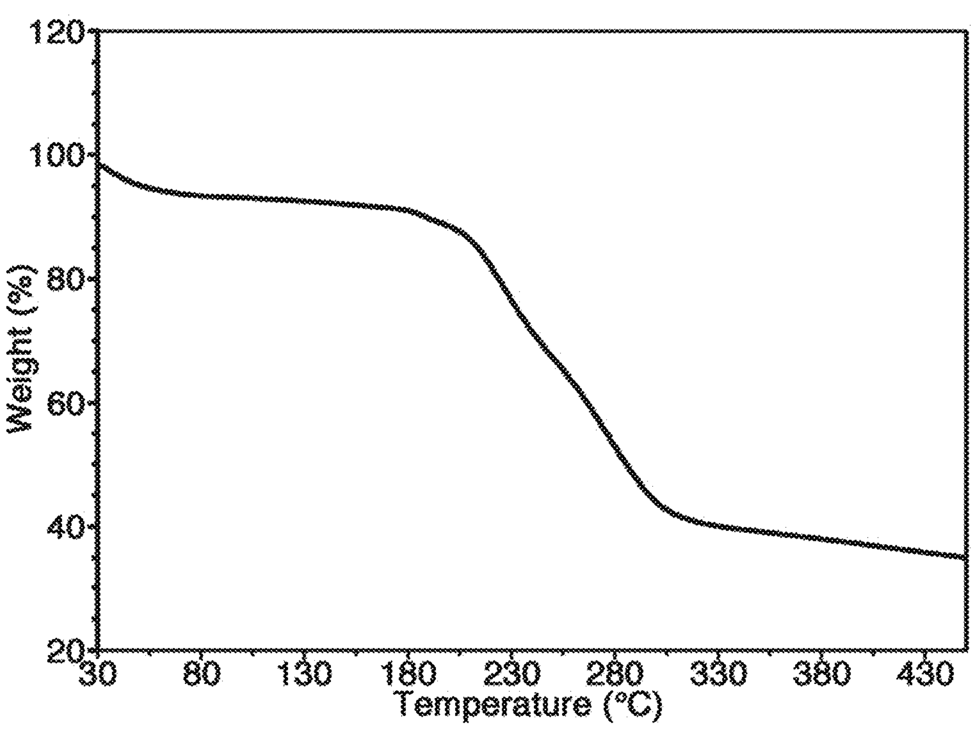

FIG. 59 shows a TGA spectrum of sarcosine:enriched tannic acid 1:1 salt.

Figure 60:
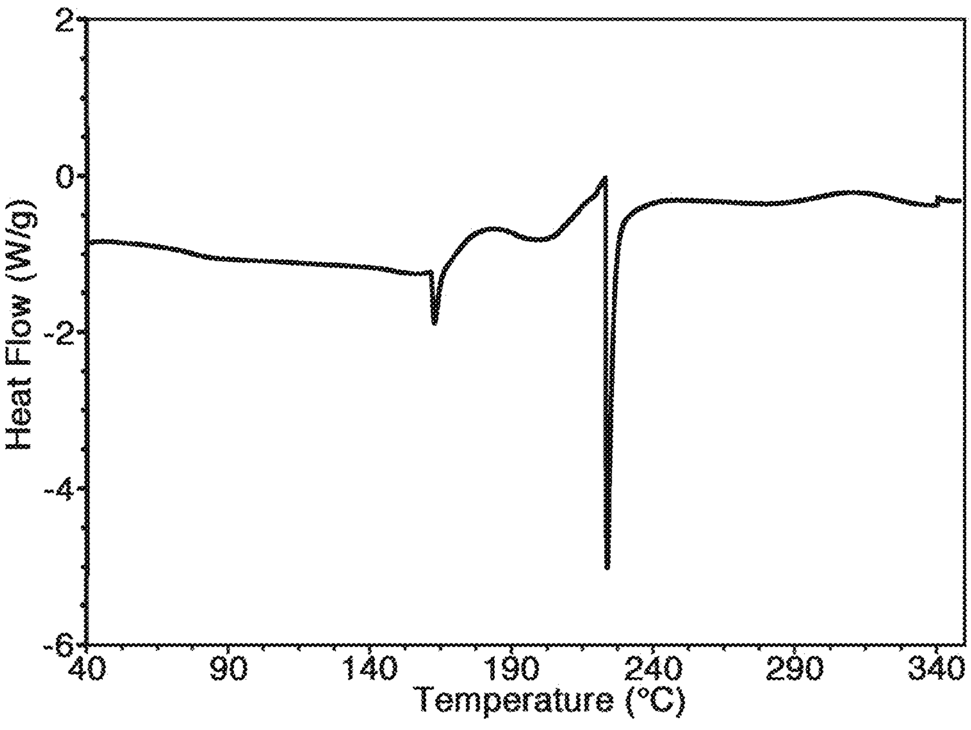

FIG. 60 shows a DSC spectrum of sarcosine:enriched tannic acid 1:1 salt.

Figure 61:
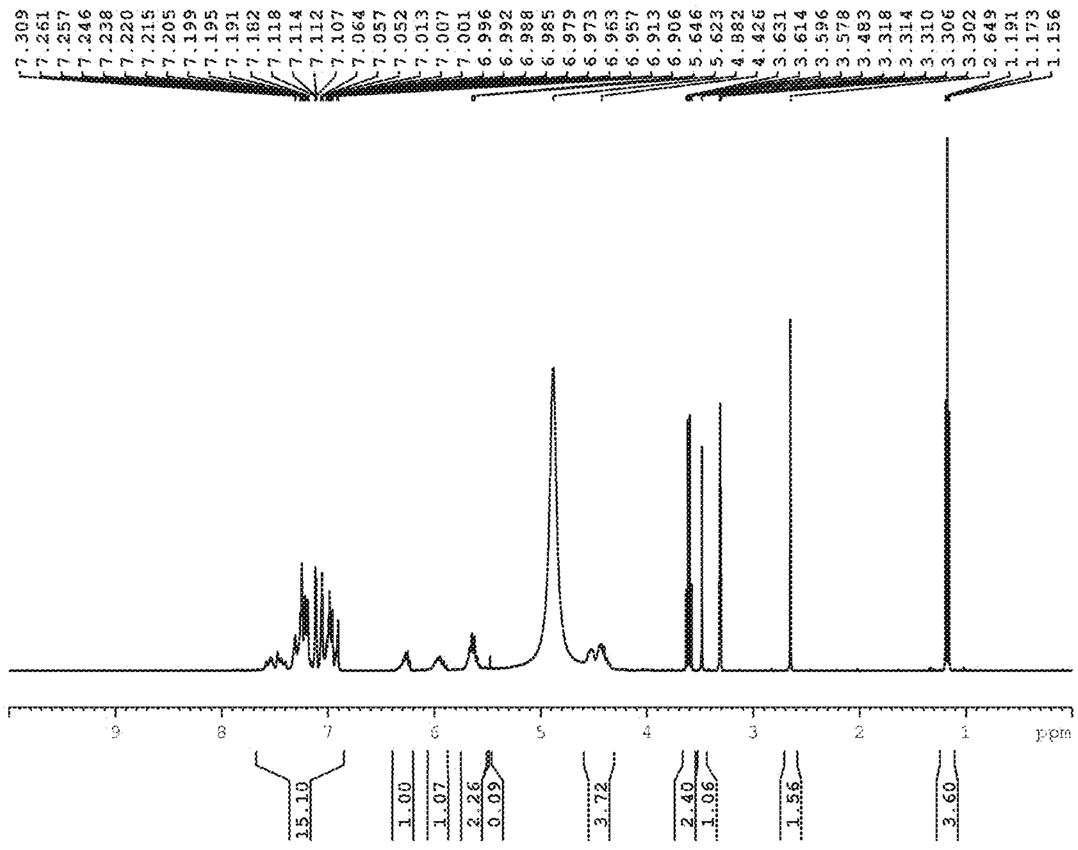

FIG. 61 shows a 1H-NMR spectrum of sarcosine:enriched tannic acid 1:2 salt.

Figure 62:
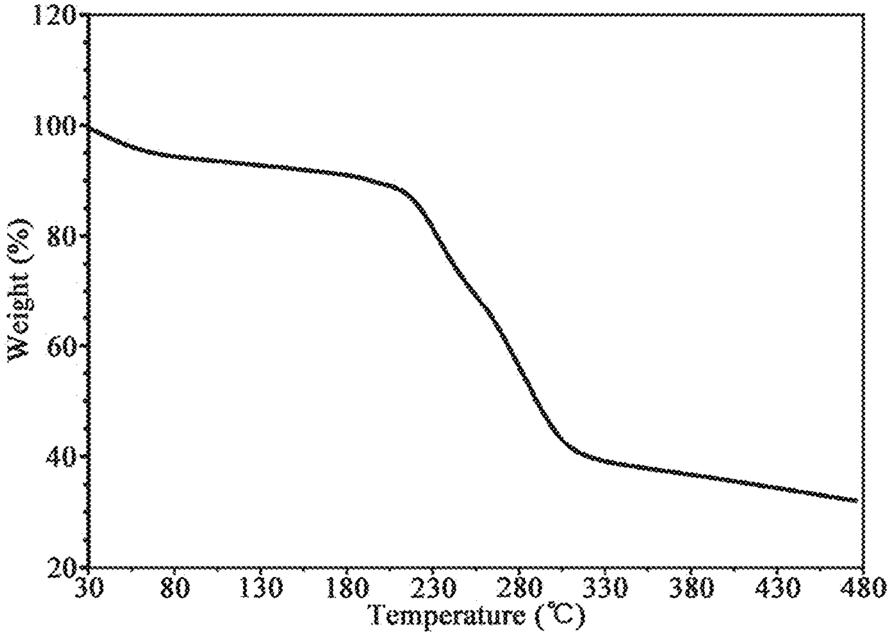

FIG. 62 shows a TGA spectrum of sarcosine:enriched tannic acid 1:2 salt.

Figure 63:
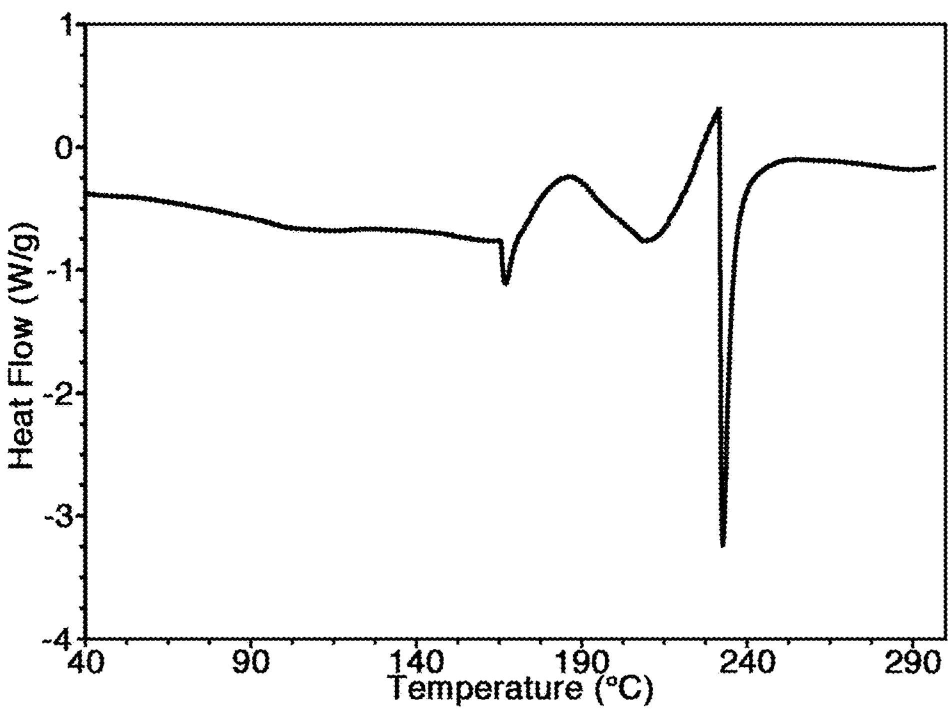

FIG. 63 shows a DSC spectrum of sarcosine:enriched tannic acid 1:2 salt.

Figure 64:
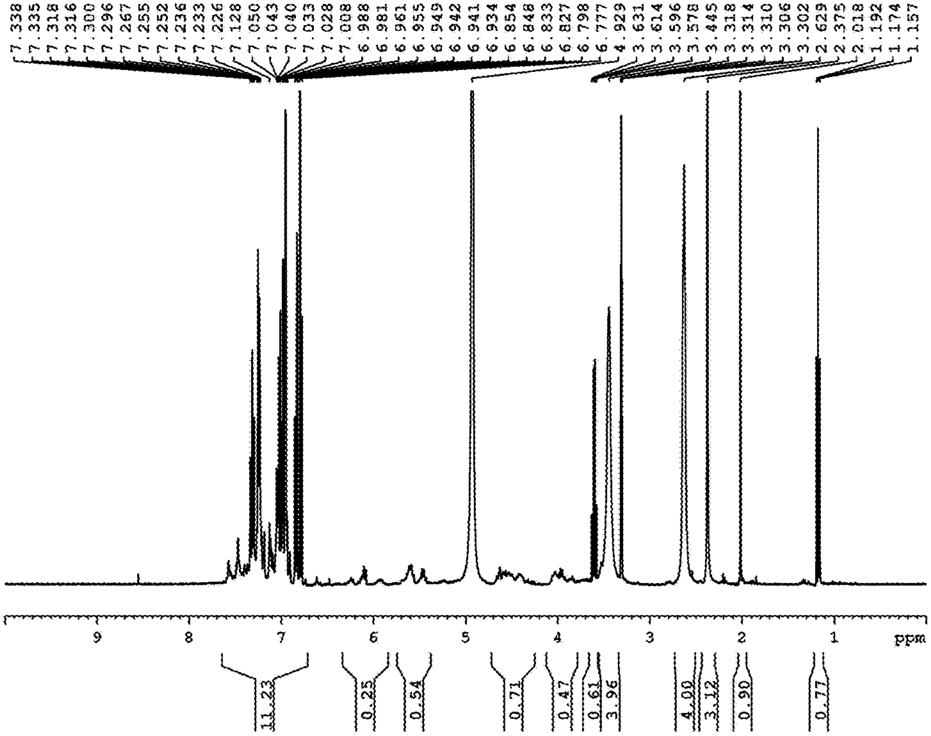

FIG. 64 shows a 1H-NMR spectrum of clozapine:tannic acid 6:1 salt.

Figure 65:
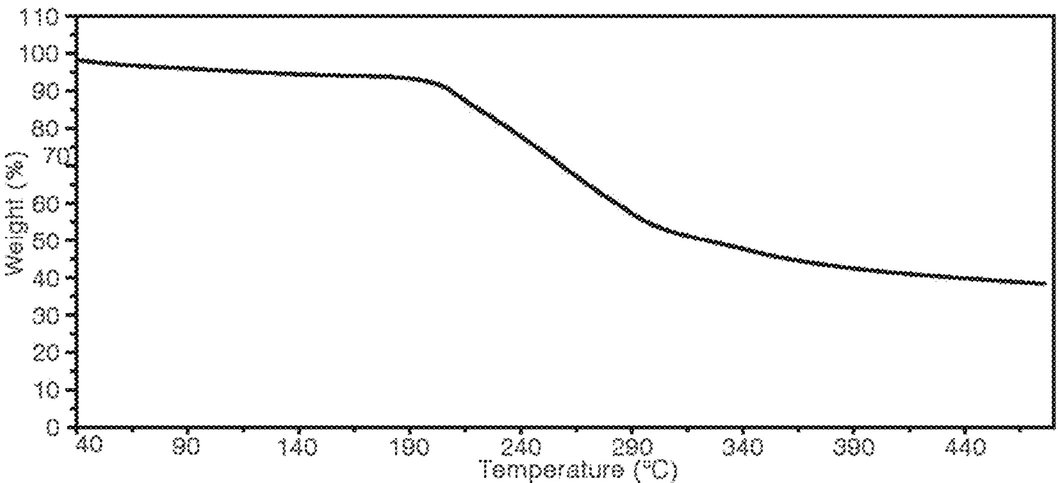

FIG. 65 shows a TGA spectrum of clozapine:tannic acid 6:1 salt.

Figure 66:
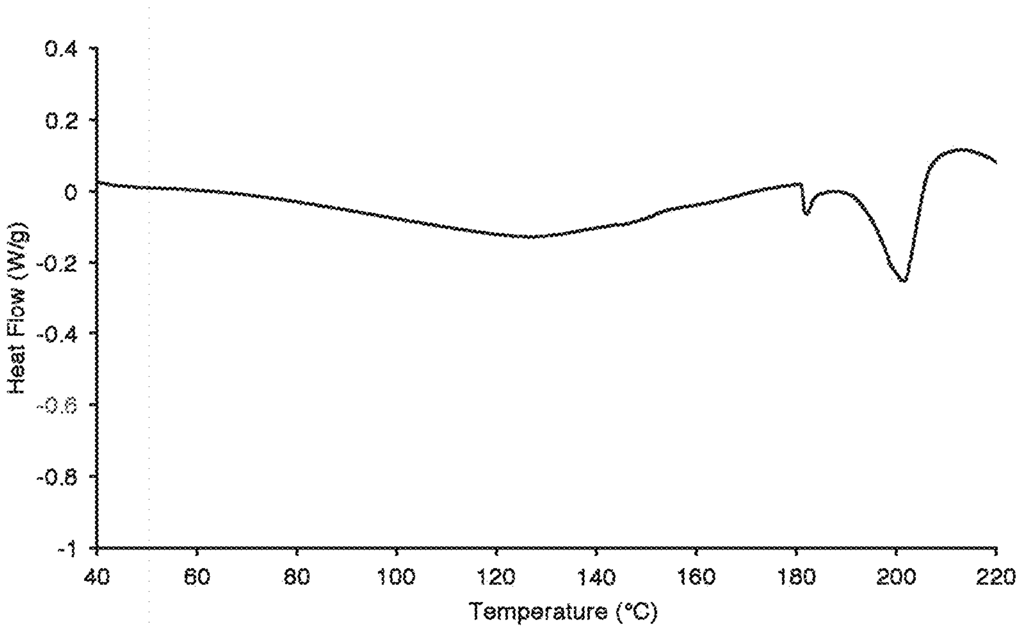

FIG. 66 shows a DSC spectrum of clozapine:tannic acid 6:1 salt.

Figure 67:
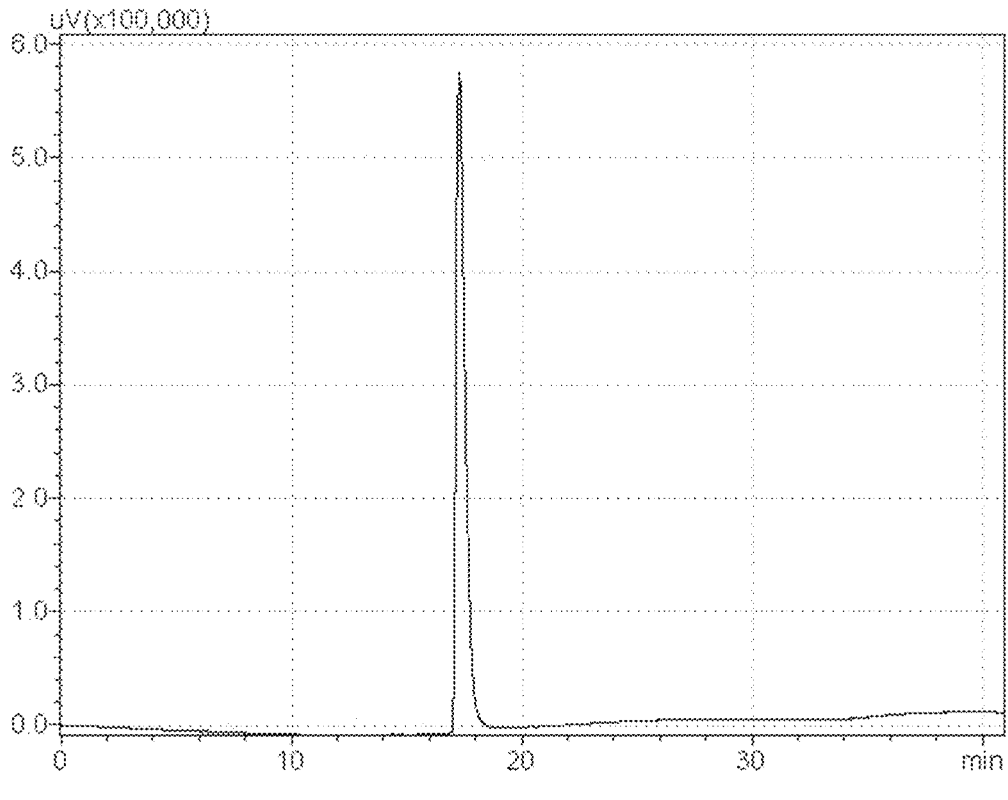

FIG. 67 shows HPLC analysis of clozapine before stress study.

Figure 68:
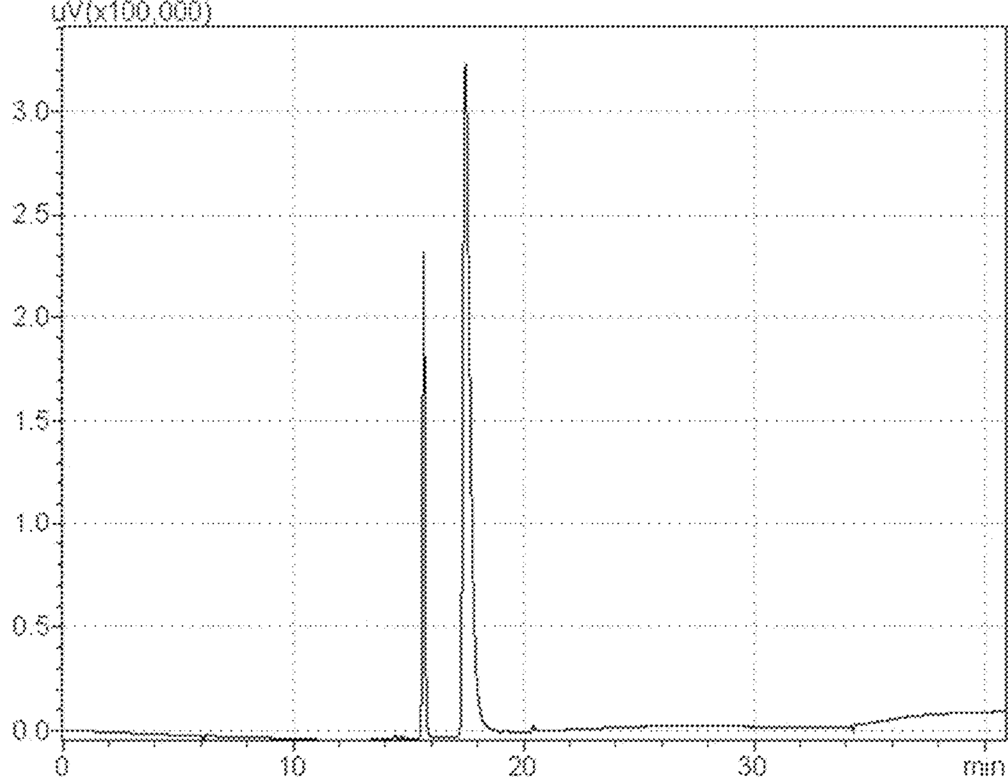

FIG. 68 shows HPLC analysis of clozapine mixed with benzoic acid before stress study.

Figure 69:
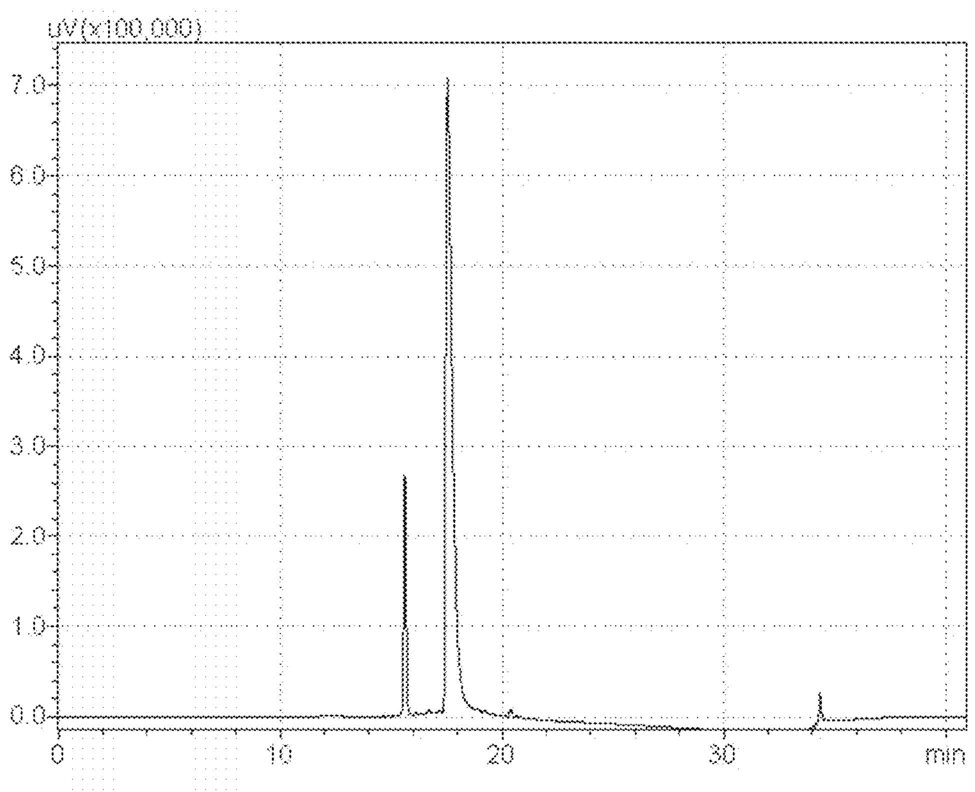

FIG. 69 shows HPLC analysis of clozapine benzoic acid 1:1 salt form mixed with benzoic acid before stress study.

Figure 70:
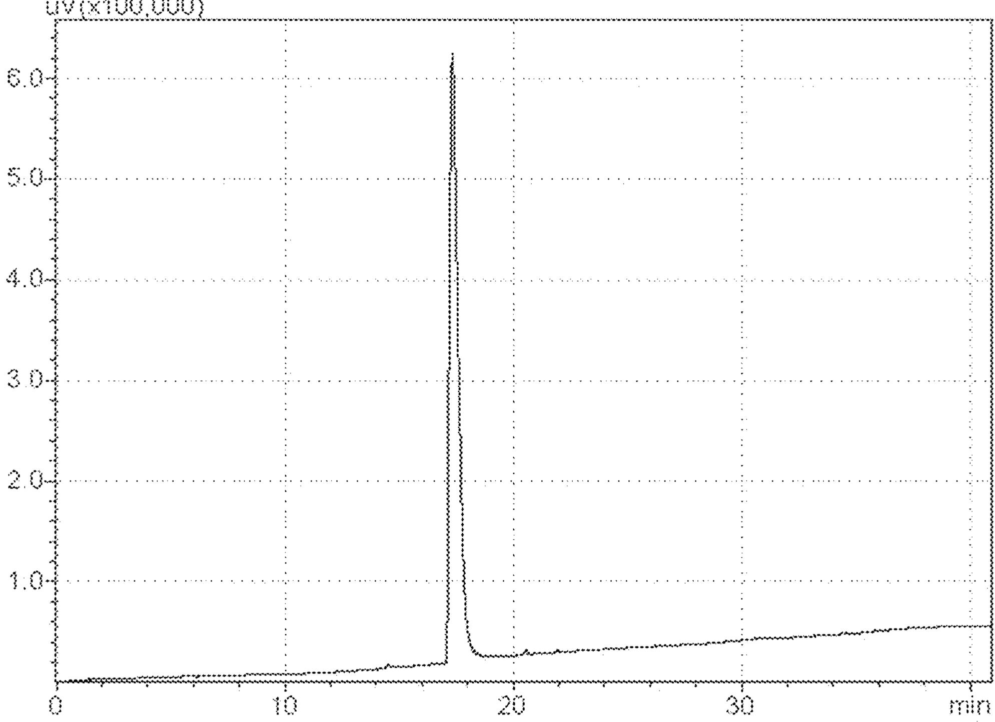

FIG. 70 shows HPLC analysis of clozapine kept at 40° C./75% RH (relative humidity) for 30 days.

Figures 71, 72:
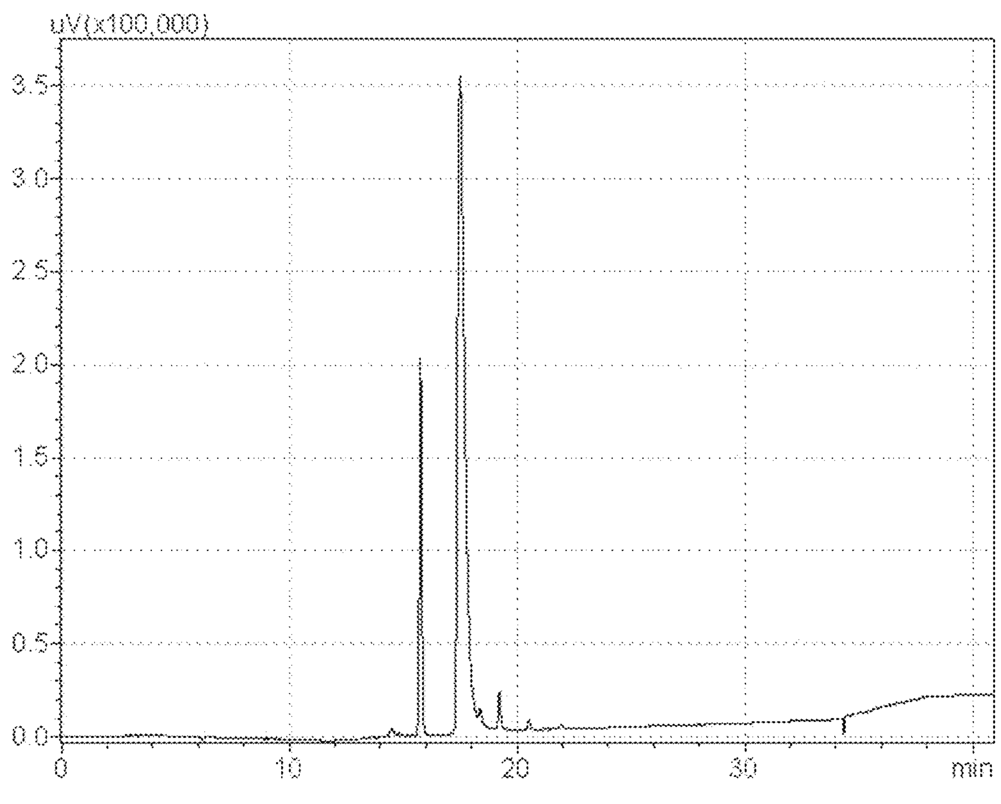

FIG. 71 shows HPLC analysis of clozapine mixed with benzoic acid kept at 40° C./75% RH for 30 days.

FIG. 72 shows HPLC analysis of clozapine benzoic acid 1:1 salt form mixed with benzoic acid kept at 40° C./75% RH for 30 days.

Figure 73:
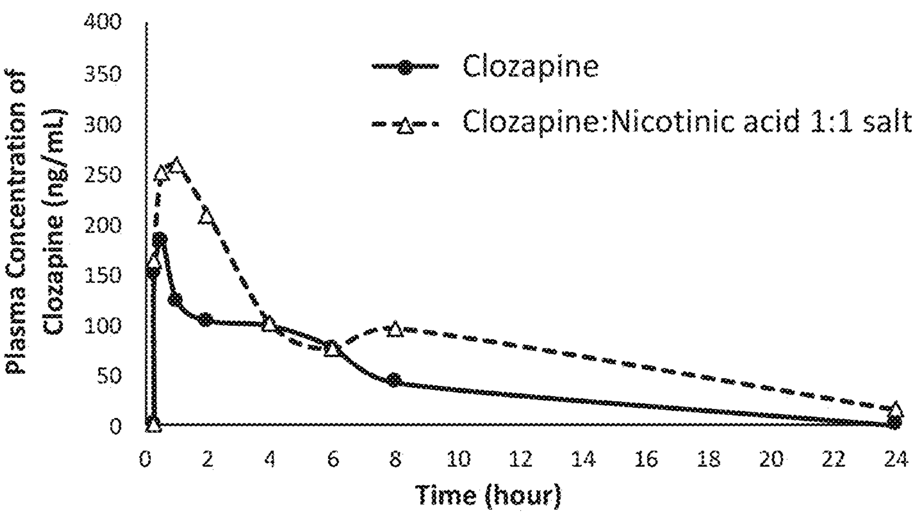

FIG. 73 is a diagram showing line charts of plasma concentration-time curve of clozapine and clozapine:nicotinic acid (1:1) salt in rats.

Figure 74:
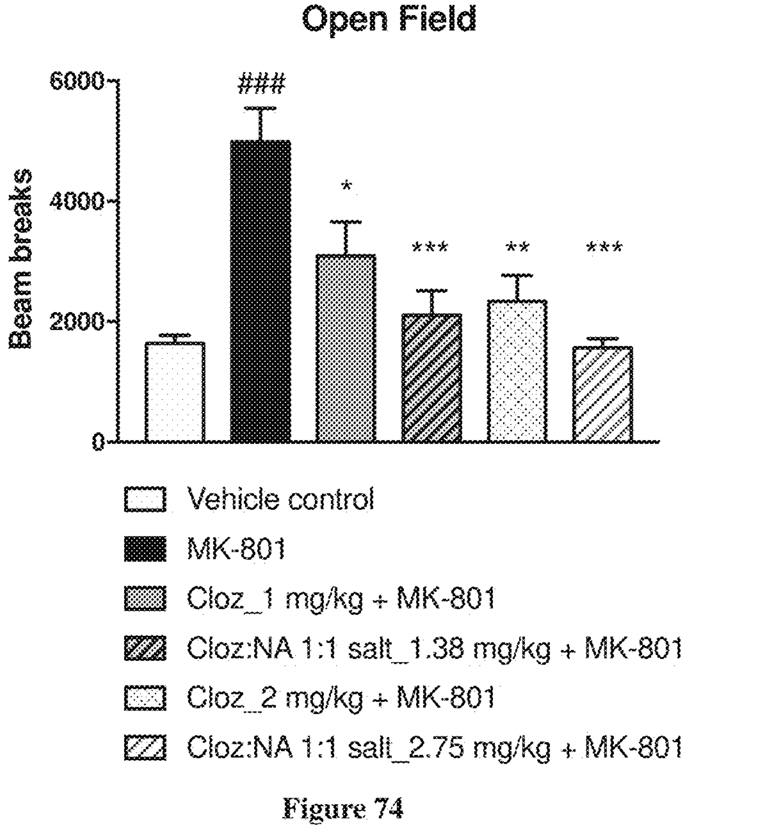

FIG. 74 is a diagram showing the effects of clozapine (Clz) and clozapine:nicotinic acid 1:1 salt (Clz:NA 1:1 salt) on locomotor activity in MK-801 treated mice. ###P<0.001 compared to vehicle control group; *P<0.05, P<0.01, *P<0.001 compared to MK-801 group.

Figure 75:
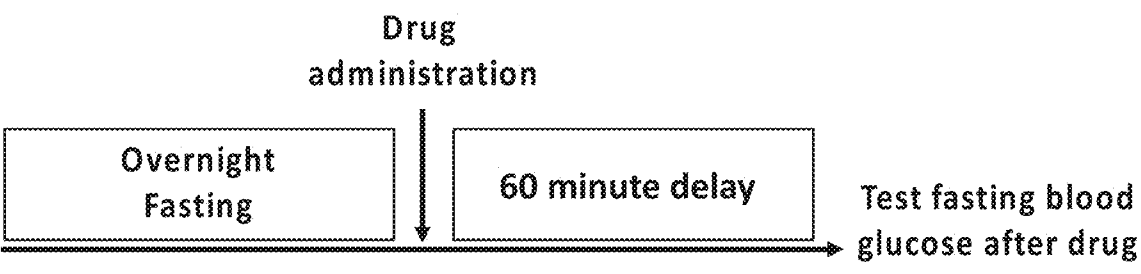

FIG. 75 is a schematic illustration of an experimental protocol describing blood glucose test in mice.

Figure 76:
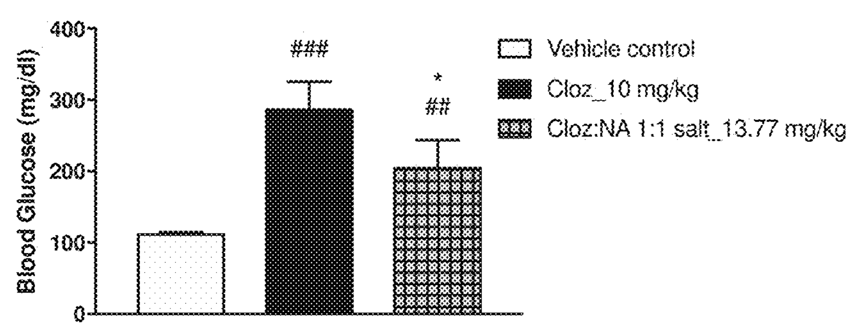
Figure 76:
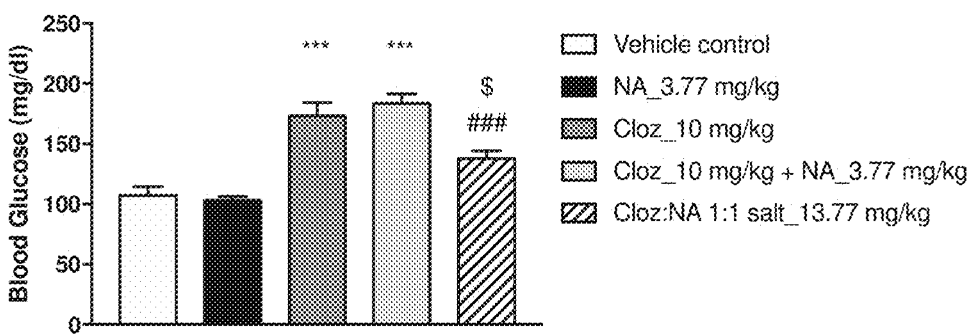

FIG. 76 is a diagram showing the fasting blood glucose levels in mice received acute administration of nicotinic acid (NA, 3.77 mg/kg), clozapine (Clz, 10 mg/kg) and clozapine: nicotinic acid 1:1 salt (Clz:NA 1:1 salt, 13.77 mg/kg) by (A) intraperitoneal (i.p.) injection and (B) oral gavage. ##P<0.01, ###P<0.001 compared to vehicle control group; *P<0.05 compared to Clz_10 mg/kg.

Figure 77:
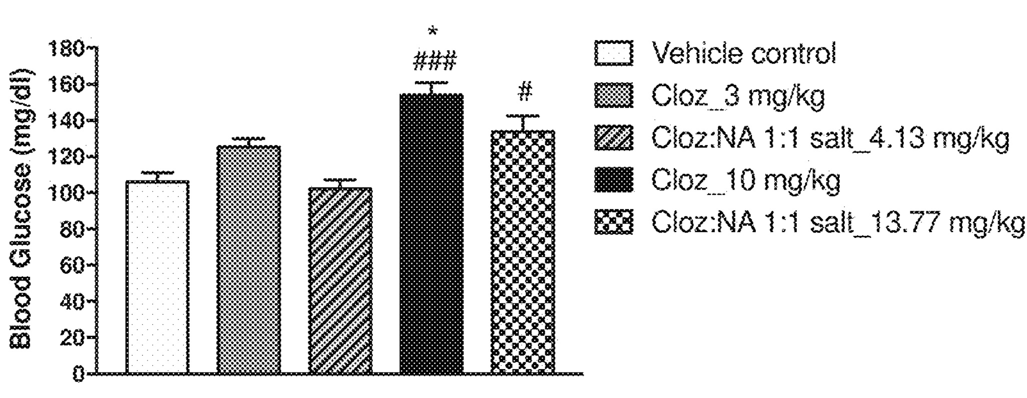

FIG. 77 is a diagram showing the effects of clozapine (Clz) and clozapine:nicotinic acid 1:1 salt (Clz:NA 1:1 salt) on the fasting blood glucose levels by oral administration for 3 days. ##P<0.01, ###P<0.001 compared to vehicle control group; *P<0.05 compared to clozapine_3 mg/kg.

Figure 78:
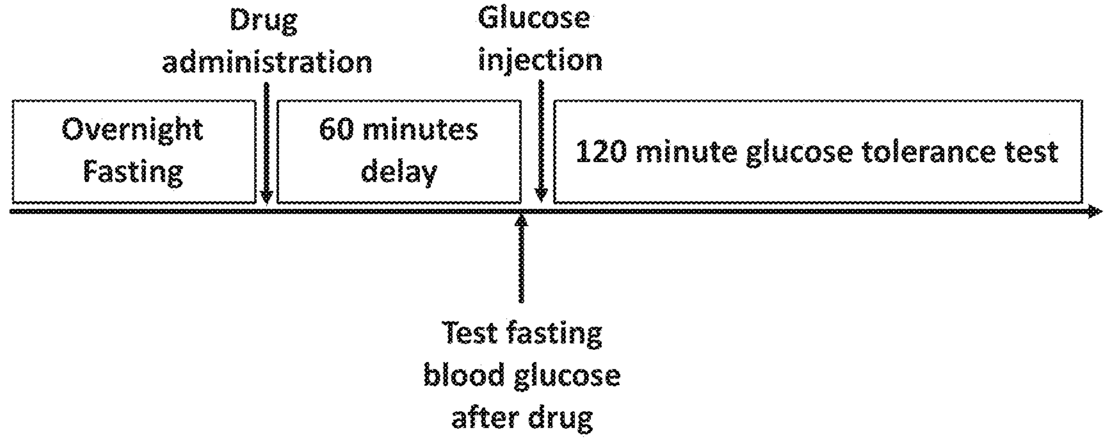

FIG. 78 is a schematic illustration of the experimental protocol describing glucose tolerance test (GTT) in mice.

Figure 79:
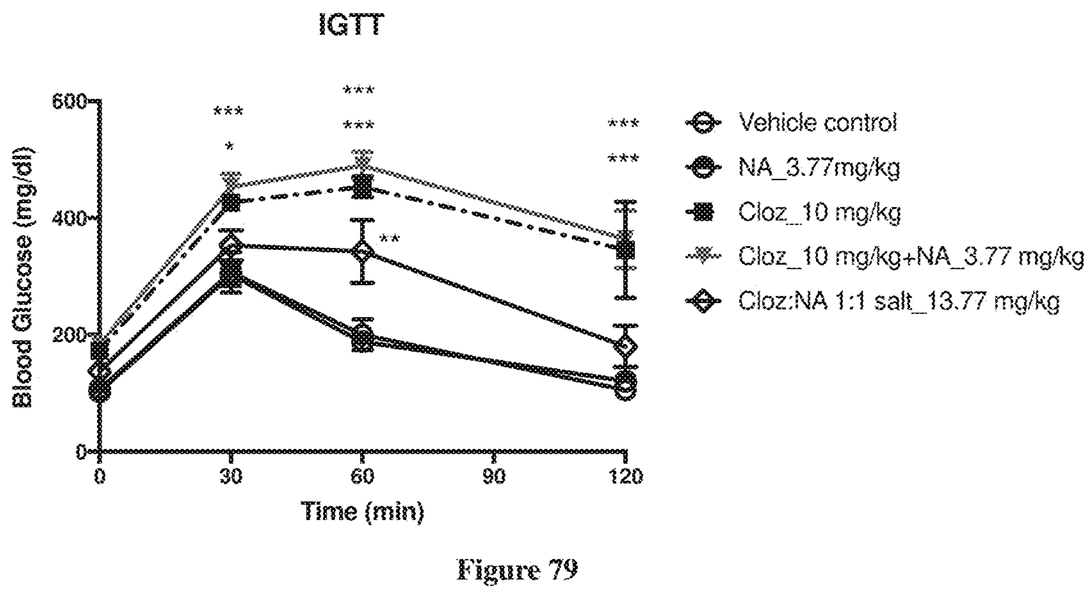

FIG. 79 is a diagram showing the effects of nicotinic acid (NA, 3.77 mg/kg), clozapine (Clz, 10 mg/kg), clozapine (Clz, 10 mg/kg)+nicotinic acid (3.77 mg/kg) and clozapine: nicotinic acid 1:1 salt (Clz:NA 1:1 salt, 13.77 mg/kg) on glucose metabolism in mice by oral administration. *P<0.05, P<0.01, *P<0.001 compared to vehicle control group.

Figure 80:
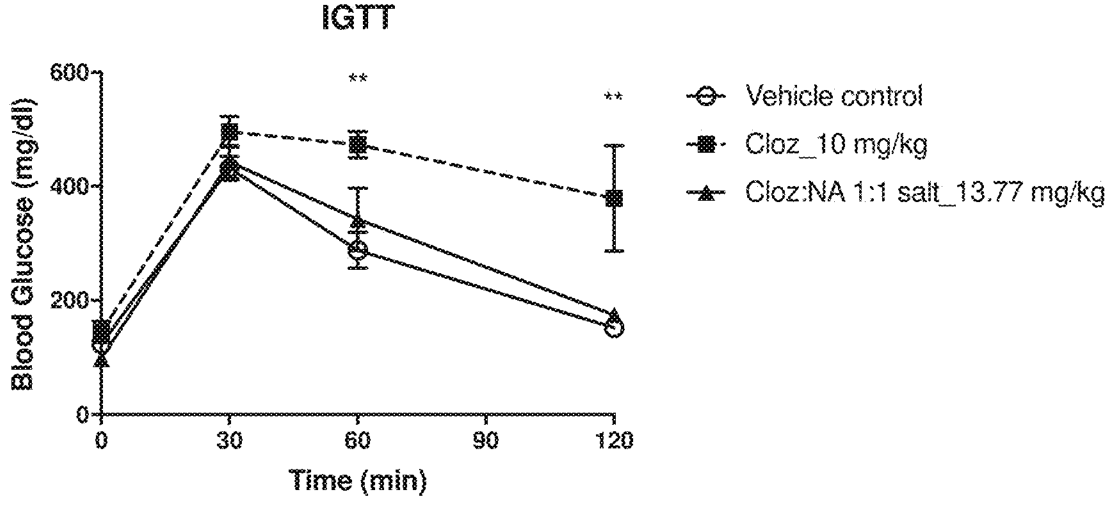

FIG. 80 is a diagram showing the effects of clozapine (Clz, 10 mg/kg), and clozapine:nicotinic acid 1:1 salt (Clz: NA 1:1 salt, 13.77 mg/kg) in glucose metabolism after oral administration for 19 days. **P<0.01 compared to vehicle control group.

Figure 81:
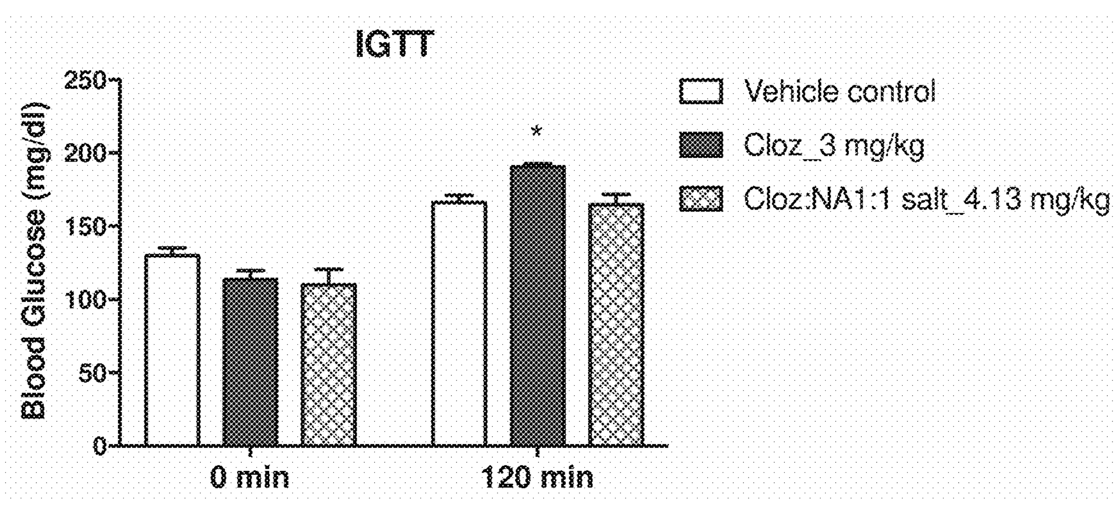

FIG. 81 is a diagram showing the effects of clozapine (Clz, 3 mg/kg) and clozapine:nicotinic acid 1:1 salt (Clz:NA 1:1 salt, 4.13 mg/kg) on glucose metabolism after oral administration for 36 days. *P<0.05 compared to vehicle control group.

Figure 82:
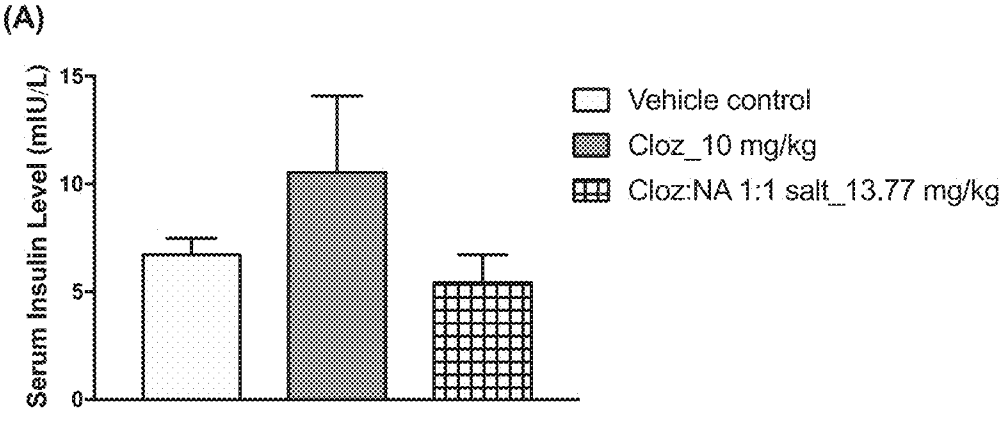
Figure 82:
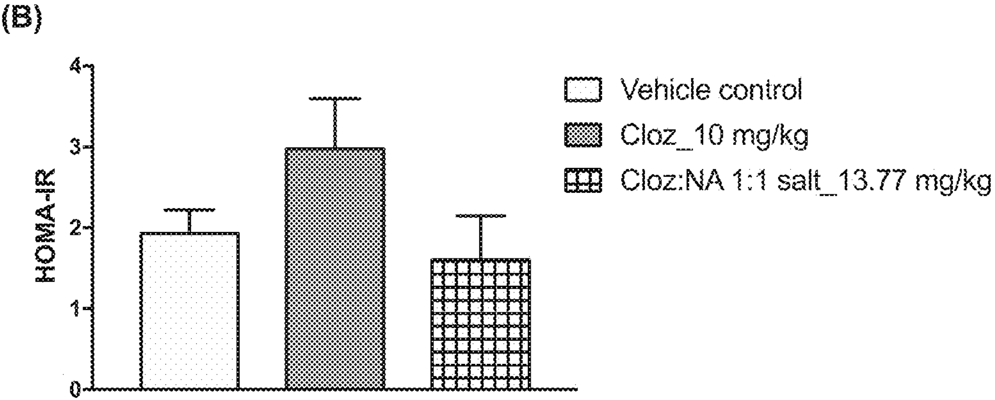

FIG. 82 is a diagram showing the effects of clozapine (Clz, 10 mg/kg) and clozapine:nicotinic acid 1:1 salt (Clz: NA 1:1 salt, 13.77 mg/kg) on (A) fasting insulin levels and (B) homeostatic model assessment-insulin resistance (HOMA-IR) index in mice by oral administration for 8 days.

Figure 83:
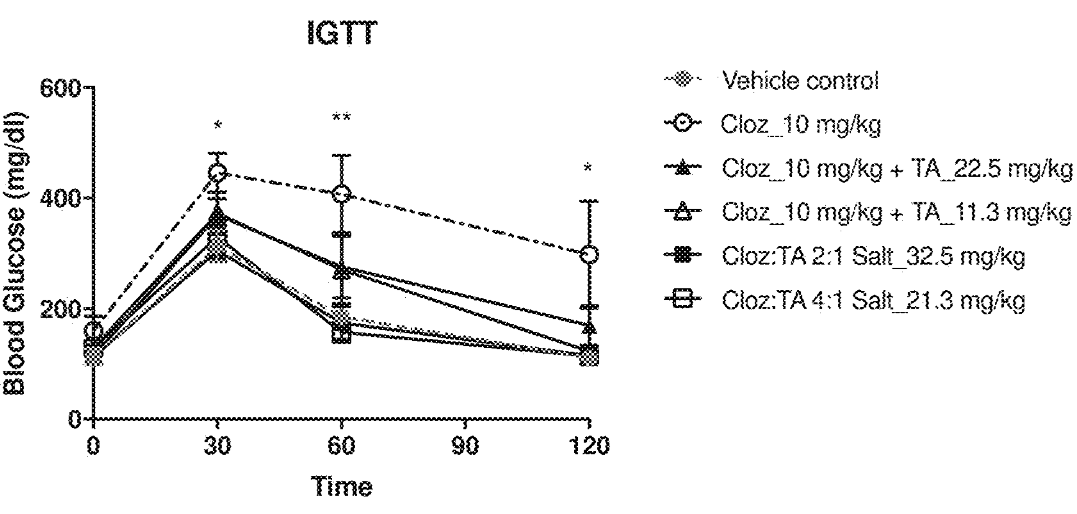

FIG. 83 is a diagram showing the changes in blood glucose levels over time in vehicle, clozapine (Clz, 10 mg/kg), clozapine (Clz, 10 mg/kg)+enriched tannic acid (TA, 22.5 mg/kg), clozapine (Clz, 10 mg/kg)+enriched tannic acid (TA, 11.3 mg/kg), clozapine:enriched tannic acid 2:1 salt (Clz:TA 2:1 salt, 32.5 mg/kg) and clozapine:enriched tannic acid 4:1 salt (Clz:TA 4:1 salt, 21.3 mg/kg) groups. *P<0.05, **P<0.01 compared to vehicle control.

Figure 84:
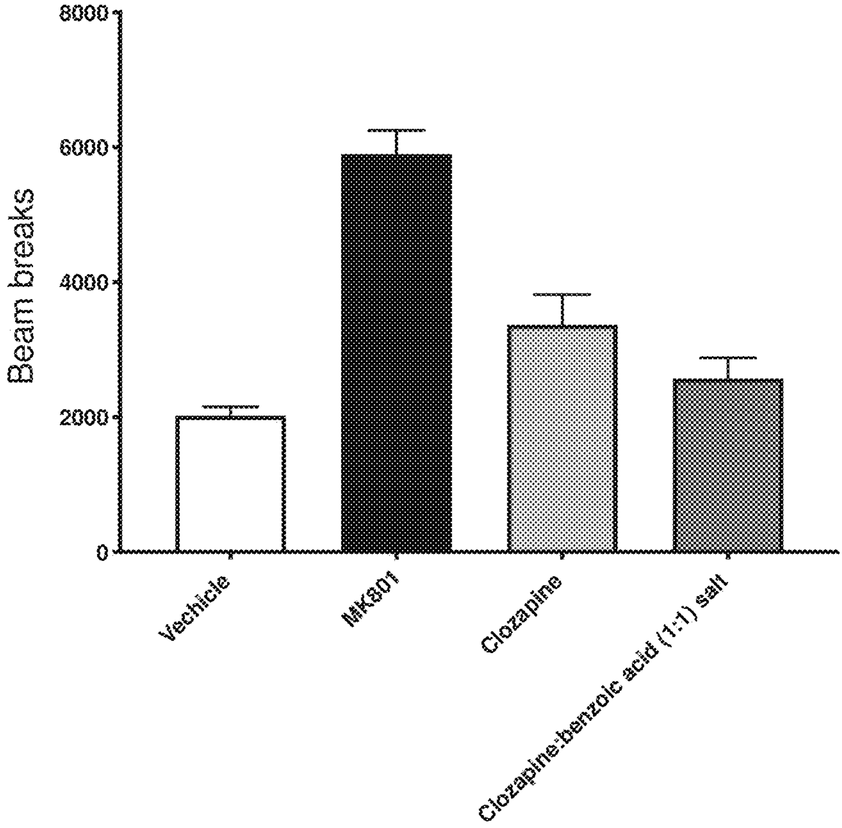

FIG. 84 is a diagram showing the effects of clozapine (1 mg/kg) and clozapine:benzoic acid (1:1) salt (1.37 mg/kg) on locomotor activity in MK-801 (0.2 mg/kg; intraperitoneal injection) treated mice.

Figure 85:
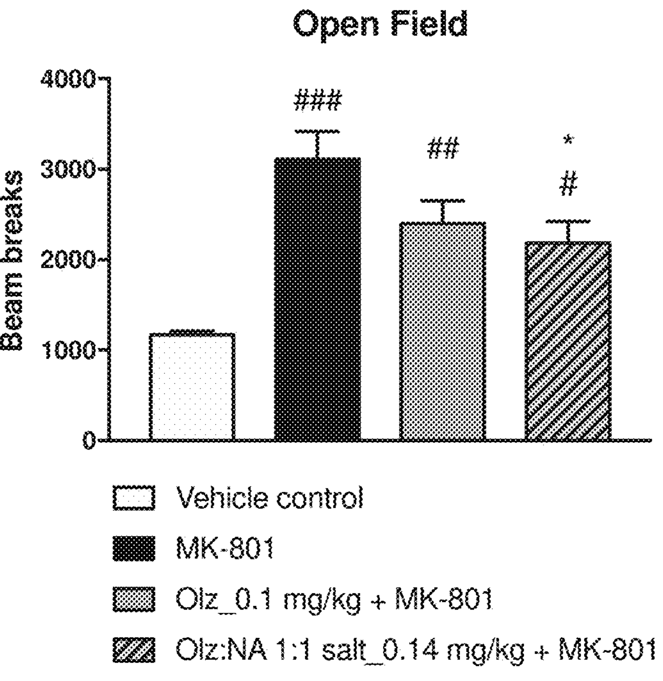

FIG. 85 is a diagram showing the effects of olanzapine and olanzapine salts on locomotor activity in MK-801 treated mice. #P<0.05, ##P<0.01, ###P<0.001 compared to vehicle control group; *P<0.05 compared to MK-801 group.

Figure 86:
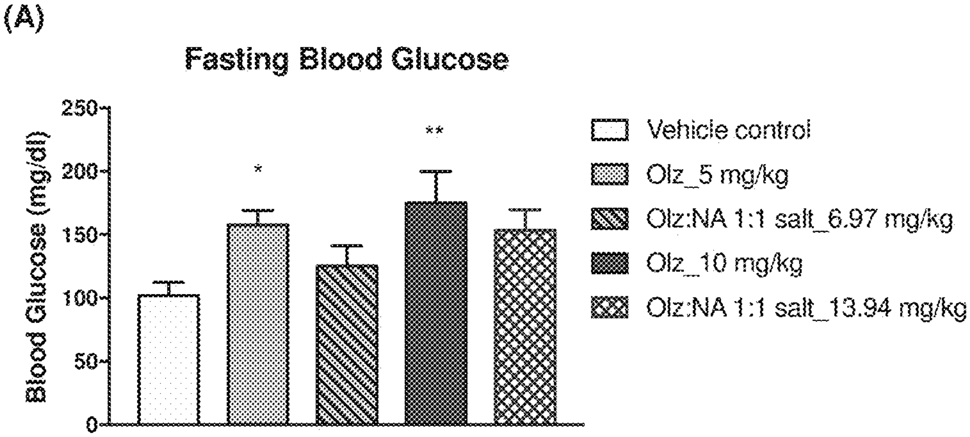
Figure 86:
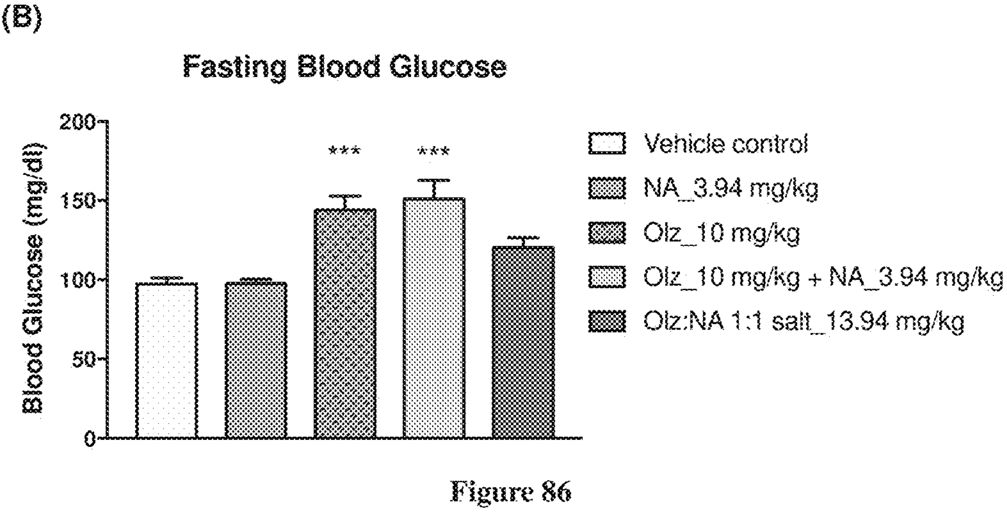

FIG. 86 is a diagram showing the fasting blood glucose levels in mice received acute administration of nicotinic acid (NA, 3.94 mg/kg), olanzapine (Olz, 10 mg/kg) and olanzapine:nicotinic acid 1:1 salt (Olz:NA 1:1 salt, 13.94 mg/kg) by (A) intraperitoneal (i.p.) injection and (B) oral gavage. *P<0.05, P<0.01, *P<0.001 compared to vehicle control group.

Figure 87:
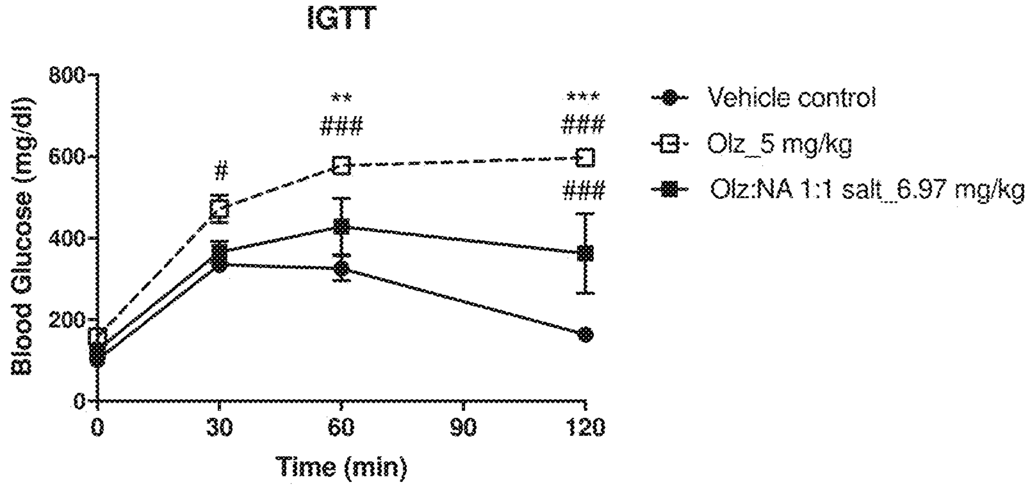

FIG. 87 is a diagram showing the effects of olanzapine (Olz, 5 mg/kg) and olanzapine:nicotinic acid 1:1 salt (Olz: NA 1:1 salt, 6.97 mg/kg) on glucose metabolism in mice by intraperitoneal (i.p.) injection. #P<0.05, ##P<0.01, ###P<0.001 compared to vehicle control group; P<0.01, *P<0.001 compared to olanzapine:nicotinic acid 1:1_6.97 mg/kg.

Figure 88:
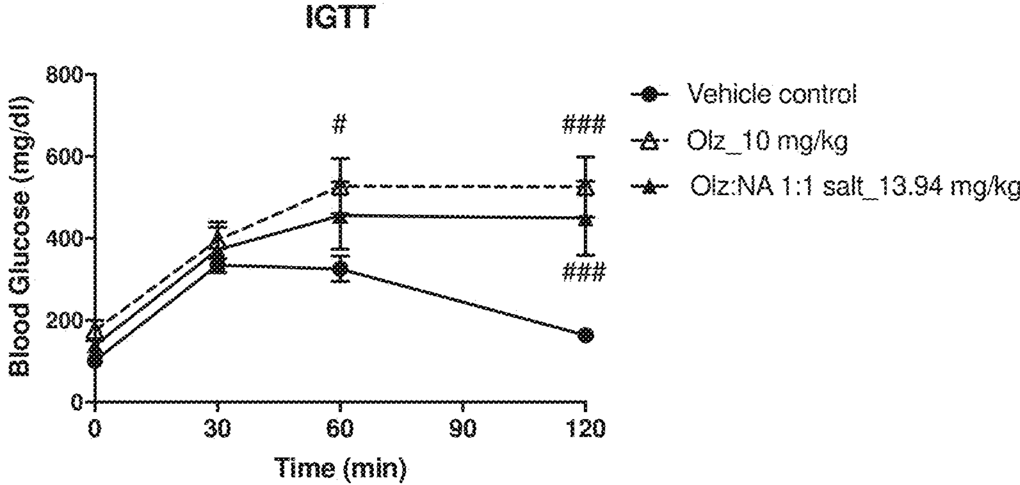

FIG. 88 is a diagram showing the effects of olanzapine (10 mg/kg) and olanzapine:nicotinic acid 1:1 salt (13.94 mg/kg) on glucose metabolism in mice by intraperitoneal (i.p.) injection. #P<0.05, ###P<0.001 compared to vehicle control group.

Figure 89:
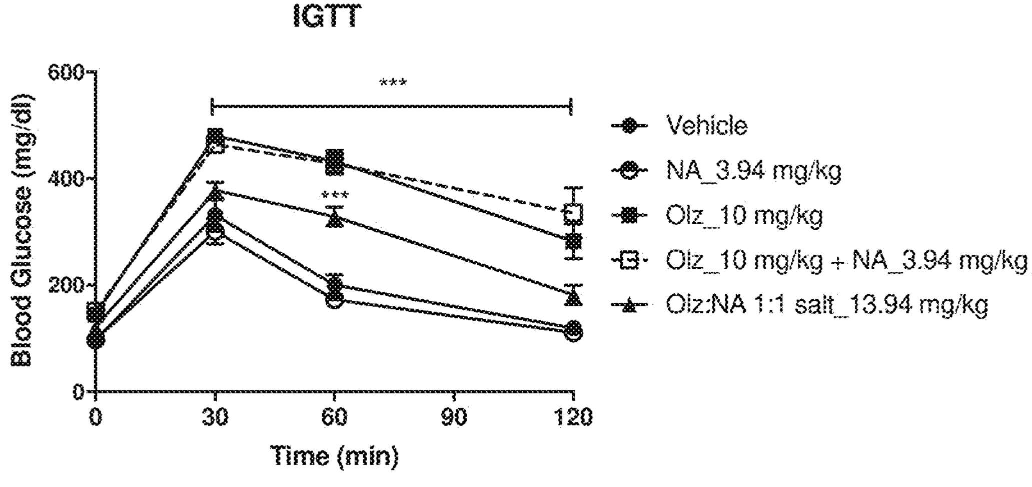

FIG. 89 is a diagram showing the effects of nicotinic acid (NA, 3.94 mg/kg), olanzapine (Olz, 10 mg/kg), olanzapine (Olz, 10 mg/kg)+nicotinic acid (NA, 3.94 mg/kg), and olanzapine:nicotinic acid 1:1 salt (Olz:NA 1:1 salt, 13.94 mg/kg) on glucose metabolism in mice by oral gavage.

Figure 90:
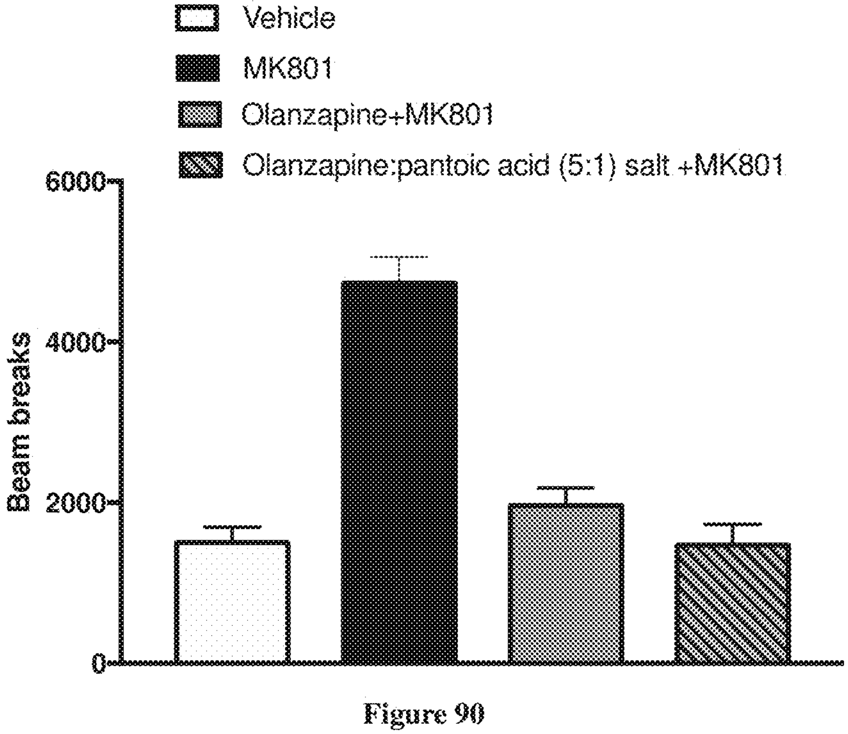

FIG. 90 is a diagram showing the effects of olanzapine (0.5 mg/kg) and olanzpine:pantoic acid 5:1 salt (0.547 mg/kg) on locomotor activity in MK-801 (0.2 mg/kg; intraperitoneal injection) treated mice.

Figure 91:
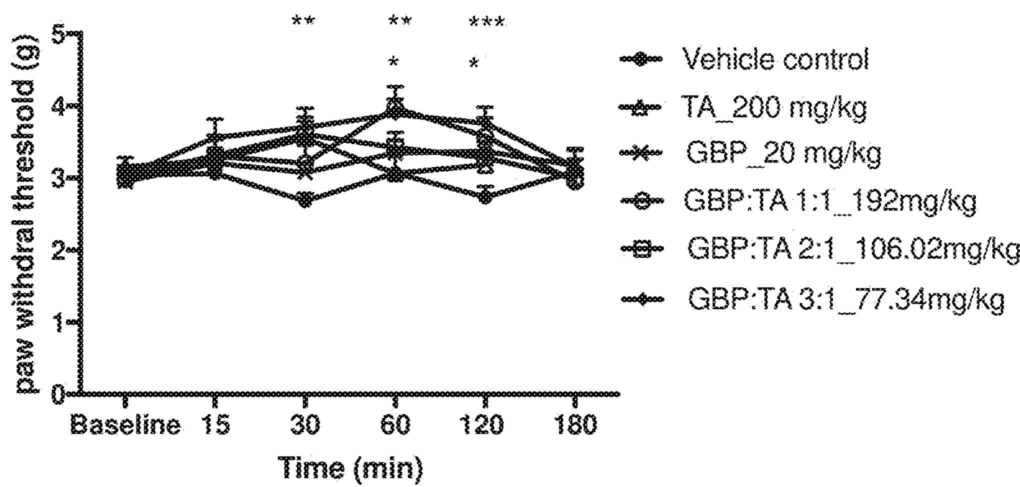

FIG. 91 is a diagram showing the paw withdrawal pain threshold over time in mice orally administrated with vehicle, enriched tannic acid (TA, 200 mg/kg), gabapentin (GBP, 20 mg/kg), gabapentin:enriched tannic acid 1:1 salt (GBP:TA 1:1 salt, 192 mg/kg), gabapentin:enriched tannic acid 2:1 salt (GBP:TA 2:1 salt, 106.02 mg/kg) or gabapentin: enriched tannic acid 3:1 salt (GBP:TA 3:1 salt, 77.34 mg/kg). Data were presented as mean±SEM and analyzed with two-way ANOVA Dunnet's test. Statistical significance was marked as follows: $^*p<0.05$, $^{}p<0.01$ and $^{*}p<0.001$ compared to vehicle control group.

Figure 92:
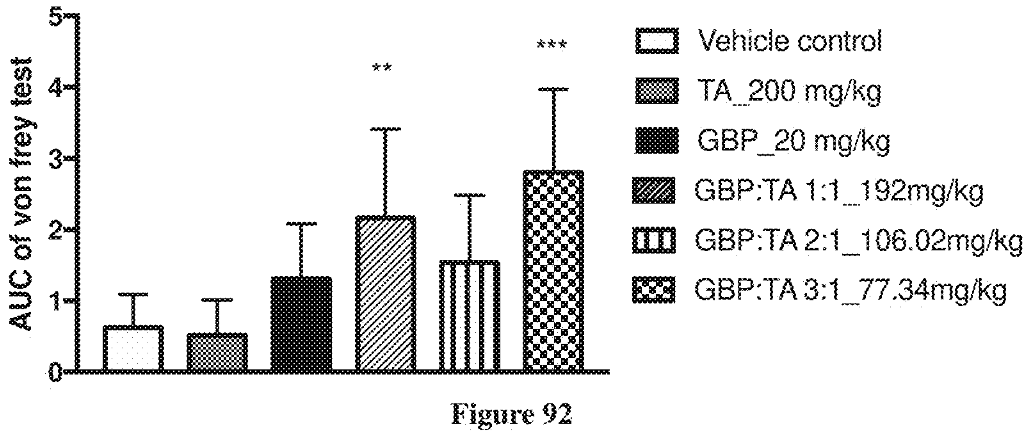

FIG. 92 is a diagram illustrating the area under the curve (AUC) of vehicle control, enriched tannic acid (TA, 200 mg/kg), gabapentin (GBP, 20 mg/kg), gabapentin:enriched tannic acid 1:1 salt (GBP:TA 1:1 salt, 192 mg/kg), gabapentin:enriched tannic acid 2:1 salt (GBP:TA 2:1 salt, 106.02 mg/kg) or gabapentin:enriched tannic acid 3:1 salt (GBP:TA 3:1 salt, 77.34 mg/kg) from the von Frey test. Data were presented as mean±SD and analyzed by one-way ANOVA Dunnett's test. Statistical significance was marked as follows: $^{}P<0.01$ and $^{*}P<0.001$ compared to vehicle control group.

Figure 93:
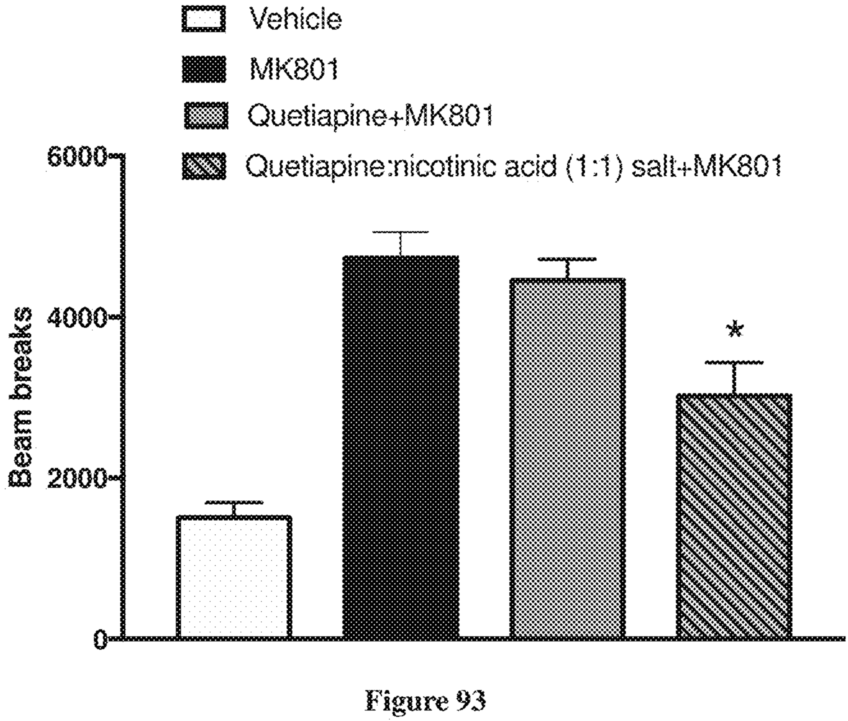

FIG. 93 is a diagram showing the effects of quetiapine (0.06 mg/kg) and quetiapine:nicotinic acid 1:1 salt (0.076 mg/kg) on locomotor activity in MK-801 (0.2 mg/kg; intraperitoneal injection) treated mice. $^*P<0.05$ compared with quetiapine group by Student's T-test.

Figure 94:
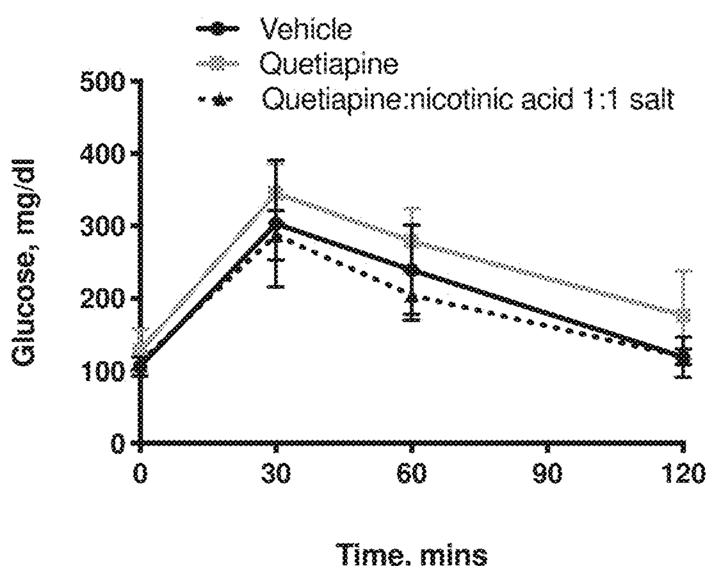
Figure 94:
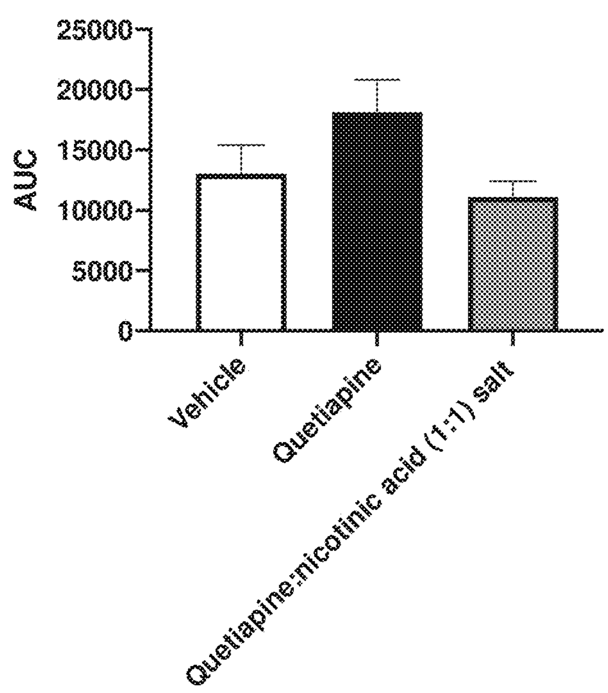

FIG. 94 is a diagram showing the blood-glucose curve (A) and area under curve (B) of vehicle, quetiapine (20 mg/kg), and quetiapine:nicotinic acid 1:1 salt (25.64 mg/kg) after glucose challenge (2 g/kg; intraperitoneal injection).

Figure 95:
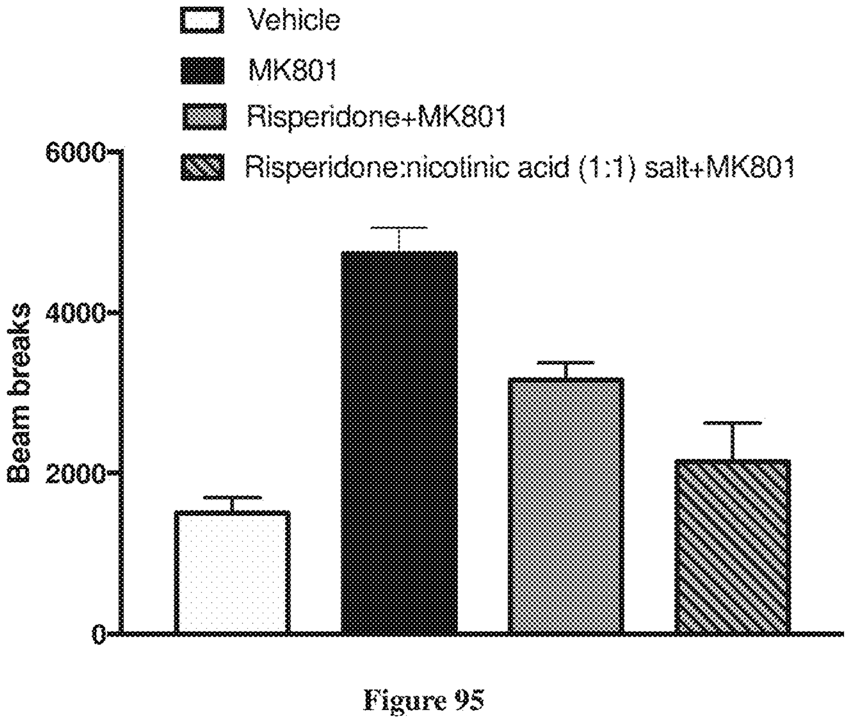

FIG. 95 is a diagram showing the effects of risperidone (0.06 mg/kg) and risperidone:nicotinic acid 1:1 salt (0.078 mg/kg) on locomotor activity in MK-801 (0.2 mg/kg; intraperitoneal injection) treated mice.

Figure 96:
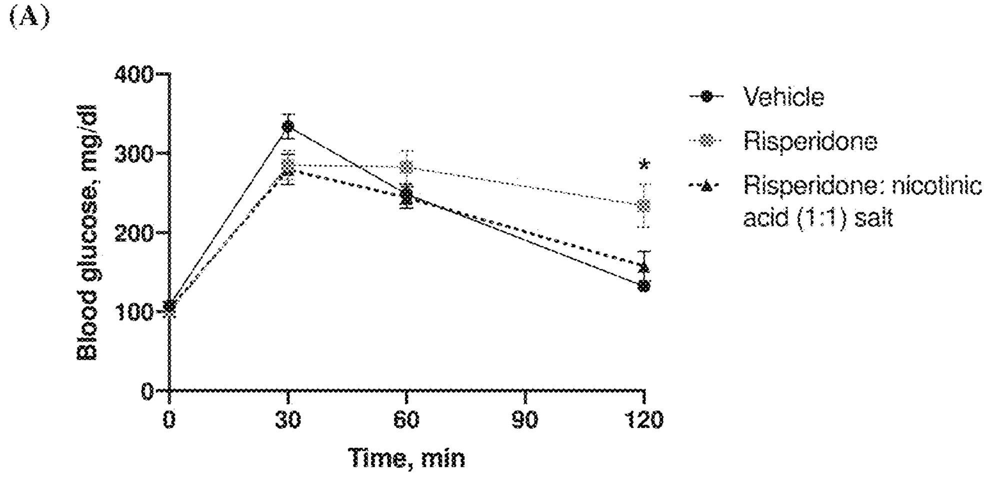
Figure 96:
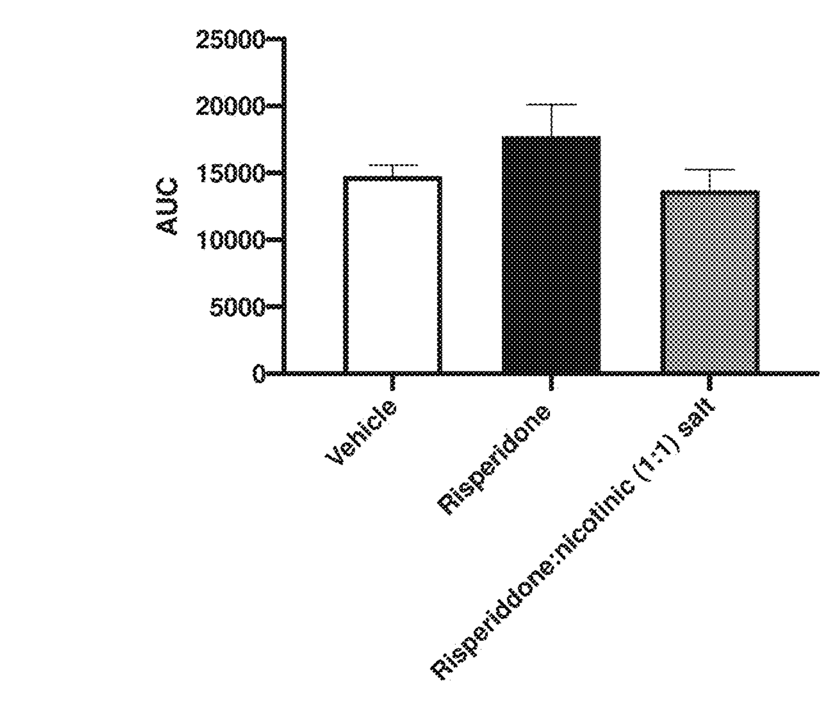

FIG. 96 is a diagram showing the blood-glucose curve (A) and area under curve (B) of vehicle, risperidone (12 mg/kg), and risperidone:nicotinic acid 1:1 salt (15.6 mg/kg) after glucose challenge (2 g/kg; intraperitoneal injection). $^*P<0.05$ compared with risperidone:nicotinic acid 1:1 salt group by Student's T-test.

Figure 97:
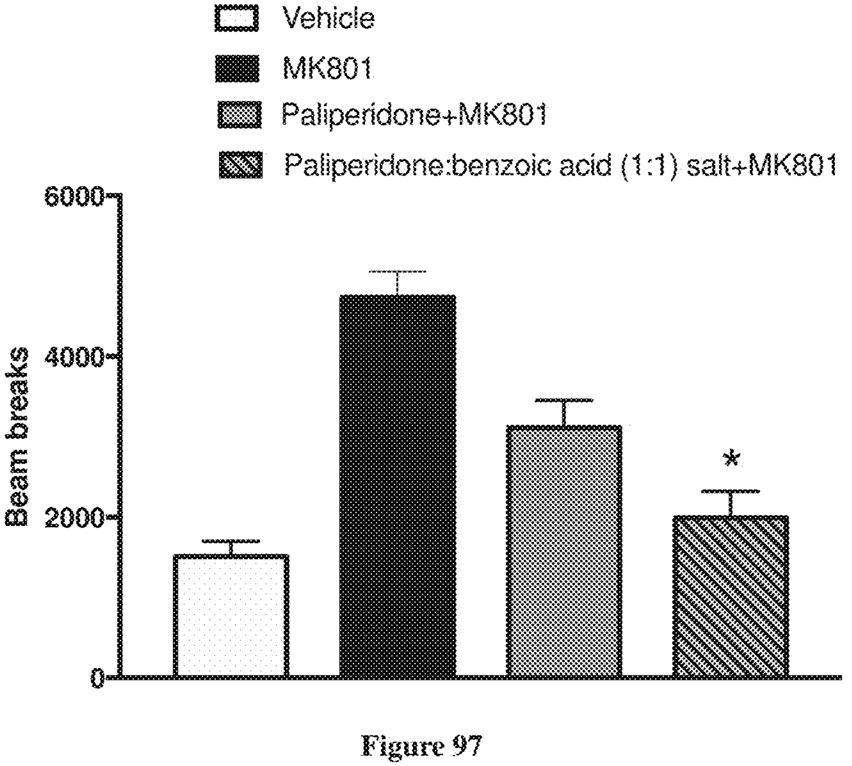

FIG. 97 is a diagram showing the effects of paliperidone (0.06 mg/kg) and olanzpine:benzoic acid 1:1 salt (0.076 mg/kg) on locomotor activity in MK-801 (0.2 mg/kg; intraperitoneal injection) treated mice. $^*P<0.05$ compared with paliperidone group by Student's T-test.

Figure 98:
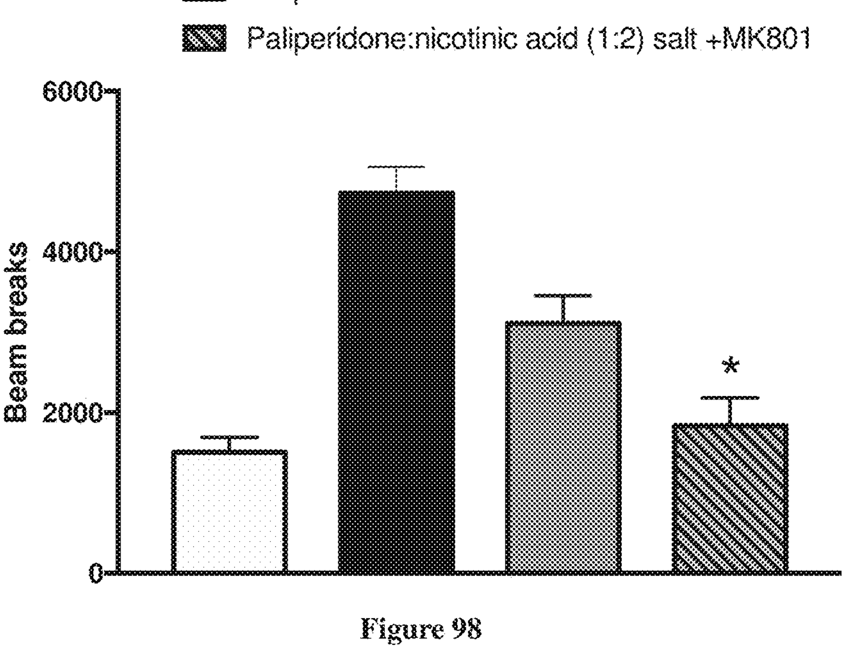

FIG. 98 is a diagram showing the effects of paliperidone (0.06 mg/kg) and paliperidone:nicotinic acid 1:2 salt (0.094 mg/kg) on locomotor activity in MK-801 (0.2 mg/kg; intraperitoneal injection) treated mice. $^*P<0.05$ compared with paliperidone group by Student's T-test.

Figure 99:
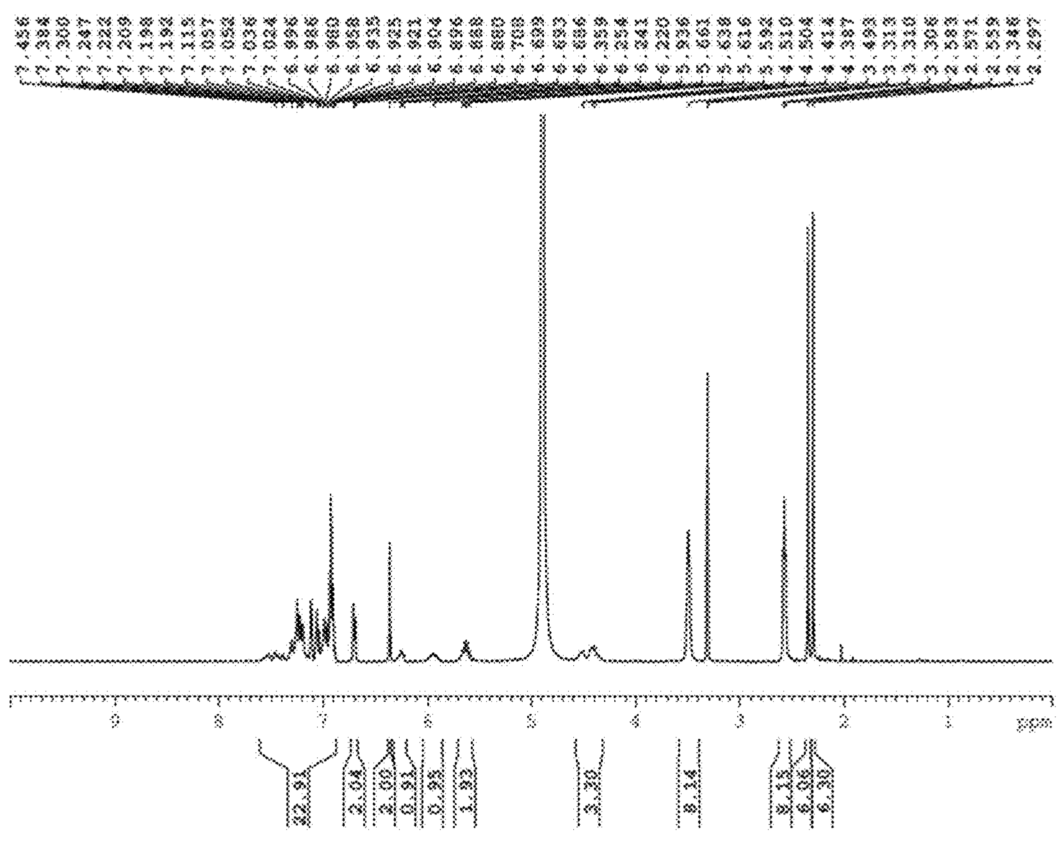

FIG. 99 shows a 1H-NMR spectrum of olanzapine:enriched tannic acid 2:1 salt.

Figure 100:
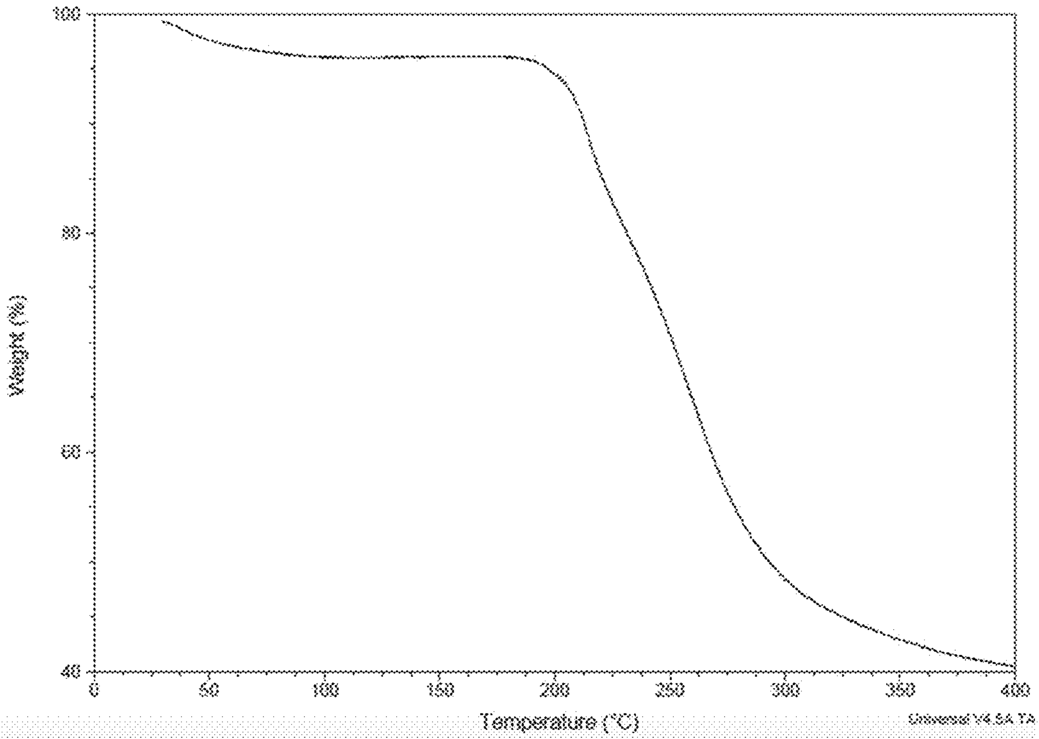

FIG. 100 shows a TGA spectrum of olanzapine:enriched tannic acid 2:1 salt.

Figure 101:
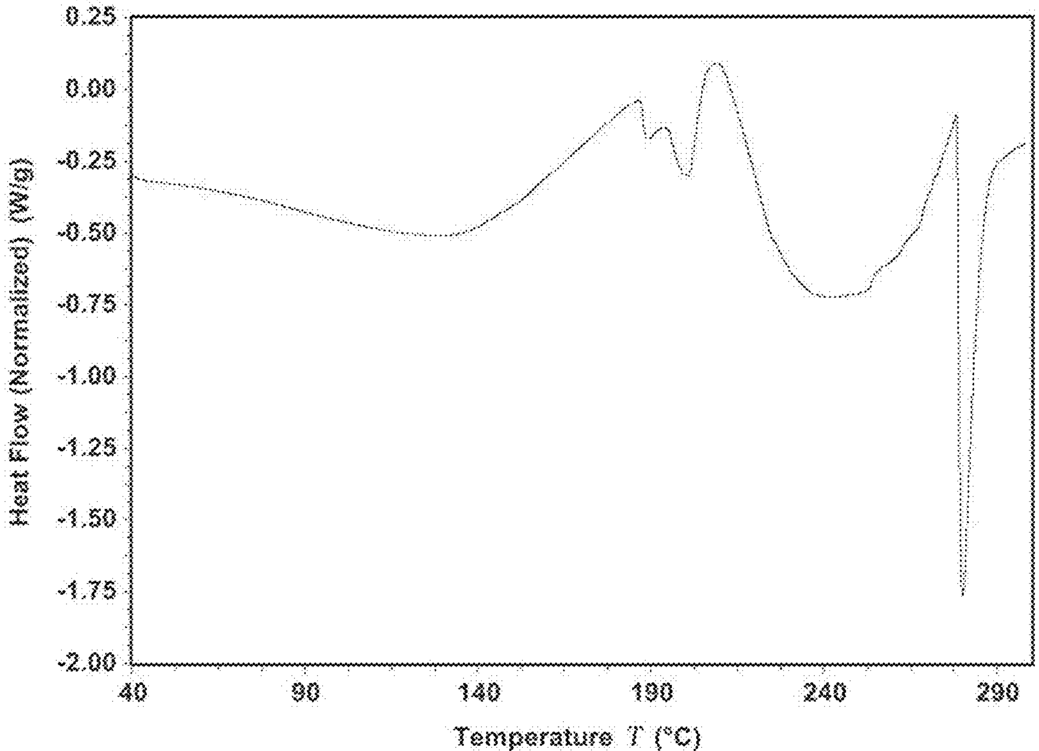

FIG. 101 shows a DSC spectrum of olanzapine:enriched tannic acid 2:1 salt.

DETAILED DESCRIPTION

The present disclosure is based on the development of salts of neuroceuticals having specific structures and specific acids, for example, benzoic acid, nicotinic acid, pantothenic acid and tannic acid. Examples of such salts reported herein showed one or more unexpected superior features, including, for example, improved water solubility, improved physical features such as flowability, increased bioavailability, improved pharmacodynamic effects, and/or enhanced therapeutic effects (e.g., for treating neuropsychiatric disorders and/or metabolism disorders). Further, exemplary salts disclosed herein mitigated side effects (such as abnormal glucose metabolism) induced by treatment with the corresponding neuroceuticals in non-salt form or different salt form. See Examples below.

Some neuroceuticals, such as atypical antipsychotics, are known to cause or contribute to causing metabolic disorders or metabolic diseases. Surprisingly, it was found that certain salt of neuroceuticals disclosed herein mitigate and/or prevent such metabolic diseases and disorders associated administration of the non-salt forms of the neuroceuticals.

Accordingly, one aspect of the present disclosure features a salt of a neuroceutical and of an acid. Also provided herein are compositions comprising any of the salts of neuroceuticals disclosed herein and therapeutic uses thereof.

I. Salt of Neuroceuticals

The salts disclosed herein can be composed of a neuroceutical and an acid. In some embodiments, the neuroceutical may be a substituted benzodiazepine, a substituted benzothiazepine, a substituted pyridopyrimidines or a substituted amino-cyclohexaneacetic acid. In some embodiments, the acid may be benzoic acid, nicotinic acid, pantothenic acid or tannic acid. Any combination of the listed neuroceuticals and the acids is within the scope of the present disclosure. In some embodiments, the molar ratio of the neuroceutical and the acid in the salt ranges from about 6:1 to about 1:5.

(i) Neuroceuticals

Neuroceuticals as disclosed herein refer to drugs or drug candidates (small molecules) that are therapeutically effective in treating or alleviating a symptom of a CNS disorder such as a neurological disorder or a psychiatric disorder. Exemplary neuroceuticals include, but are not limited to, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, LY2140023, droperidol, pimozide, butaperazine, carphenazine, remoxipride, piperacetazine, sulpiride, acamprosate, tetrabenazine, chlorpromazine, blonanserine, bromperidol, carpipramine, clocapramine, clotiapine, cyamemazine, fluspirilene, haloperidol, iloperidone, loxapine, lurasidone, melperone, molindone, mosapramine, nemonapride, oxypertine, penfluridol, pyrazine, pericyazine, perospirone, pipamperone, pipotiazine, prothipendyl, sertindole, spiperone, sultopride, tiapride, timiperone, zotepine, donepezil, galantamine, memantine, riluzole, rivastigmine, tacrine, bupropion, citalopram, lithium, mirtazapine, nortriptyline, sertraline, triiodothyronine, tranylcypromine, venlafaxine, diazepam, bromazepam, prazepam, chlordiazepoxide, clobazam, estazolam, flurazepam, clonazepam, temazepam, triazolam, alprazolam, midazolam, brotizolam, nitrazepam, flunitrazepam, oxazepam, quazepam, lorazepam, temazepam, triazolam, zolpidem, zopiclone, zaleplon, chlorpromazine, thioridazine, mesoridazine, fluphenazine, perphenazine, trifluoperazine, thiothixene, haloperidol, loxapine, molindone, haloperidol decanoate, fluphenazine decanoate, fluphenazine enanthate, risperdal consta, acetophenazine, chlorprothixene, amitriptyline, imipramine, nortriptiline, protriptyline, desipramine, trimipramine, amoxapine, bupropion sr, citalopram, s-citalopram, clomipramine, desipramine, doxepin, duloxetine, milnacipran, fluoxetine, fluvoxamine, imipramine, isocarboxazid, isoniazid, iproniazid, fluoxetine, paroxetine, sarcosine sertraline fluvoxamine, venlafaxine, velafaxine xr, milnacipram and duloxetine, mirtazapine, mianserin, reboxetine, selegiline, tranylcypromine, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, physostigmine, nicotine, huperzine alpha, vitamin c, vitamin, carotenoids, *Ginkgo biloba*, statinsamphetamine, modafinil, desoxyn, methamphetamine, cocaine, arecoline, dexmethylphenidate, dextroamphetamine, methylphenidate, lisdexamfetamine dimesylate (vyvanse), mixed salts amphetamine, atomoxetine, clonidine hydrochloride, guanfacine hydrochloride, arecoline, pemoline, lamotrigine, acamprosate, tetrabenazine, riluzole, acetaminophen, aspirin, bromfenac, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, nepafenac, oxaprozin, phenylbutazone, piroxicam, sulindac, tolmetin, celecoxib, lidocaine, nefopam, orphenadrine, cyclobenzaprine, hyoscine, fentanyl, hydrocodone, hydromorphone, levorphanol, meperidine, methadone, oxycodone, oxymorphone, propoxyphene, tapentadol, tramadol, buprenorphine, butorphanol, nalbuphine, pentazocine, acetazolamide, carbamazepine, clobazam, clonazepam, diazepam, divalproex sodium, eslicarbazepine, ethosuximide, ethotoin, felbamate, fosphenytoin, lamotrigine, lacosamide, levetiracetam, mephenytoin, metharbital, methsuximide, methazolamide, oxcarbazepine, phenobarbital, phenytoin, phensuximide, pregabalin, primidone, sodium valproate, stiripentol, tiagabine, rimethadione, valproic acid, vigabatrin, zonisamide, xenazine, tereabenazine, baclofen, austedo, lioresal, kemstro, deutetrabenazine, edaravone, acetylcholinesterase (AChE) inhibitors, levodopa, monoamine oxidase-B inhibitors.

In some embodiments, the neuroceutical may be a substituted benzodiazepine. In some examples, the substituted compound may have 1-6 substituents. In some examples, each of the substituents can independently be one of the groups of substituents listed below.

In some embodiments, the neuroceutical may be a substituted benzothiazepine. In some examples, the substituted compound may have 1-6 substituents. In some examples, each of the substituents can independently be one of the substituents listed below.

In some embodiments, the neuroceutical may be a substituted pyridopyrimidines. In some examples, the substituted compound may have 1-6 substituents. In some examples, each of the substituents can independently be one of the substituents listed below.

In some embodiments, the neuroceutical may be a substituted amino-cyclohexaneacetic acid. In some examples, the substituted compound may have 1-6 substituents. In some examples, where each of the substituents can independently be one of the substituents listed below.

In general, the term "substituted", as used herein, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary substituents include, but are not limited to, halogen, —CN, —NO2, —N3, —SO2H, —SO3H, —OH, —ORaa, —ON(Rbb)2, —N(Rbb)2, —N(Rbb)3+X—, —N(ORcc)Rbb, —SH, —SRaa, —SSRcc, —C(═O)Raa, —CO2H, —CHO, —C(ORcc)2, —CO2Raa, —OC(═O)Raa, —OCO2Raa, —C(═O)N(Rbb)2, —OC(═O)N(Rbb)2, —NRbbC(═O)Raa, —NRbbCO2Raa, —NRbbC(═O)N(Rbb)2, —C(═NRbb)Raa, —C(═NRbb)ORaa, —OC(═NRbb)Raa, —OC(═NRbb)ORaa, —C(═NRbb)N(Rbb)2, —OC(═NRbb)N(Rbb)2, —NRbbC(═NRbb)N(Rbb)2, —C(═O)NRbbSO2Raa, —NRbbSO2Raa, —SO2N(Rbb)2, —SO2Raa, —SO2ORaa, —OSO2Raa, —S(═O)Raa, —OS(═O)Raa, —Si(Raa)3, —OSi(Raa)3 —C(═S)N(Rbb)2, —C(═O)SRaa, —C(═S)SRaa, —SC(═S)SRaa, —SC(═O)SRaa, —OC(═O)SRaa, —SC(═O)ORaa, —SC(═O)Raa, —P(═O)(Raa)2, —P(═O)(ORcc)2, —OP(═O)(Raa)2, —OP(═O)(ORcc)2, —P(═O)(N(Rbb)¬2)2, —OP(═O)(N(Rbb¬¬2)2, —NRbbP(═O)(Raa)2, —NRbbP(═O)(ORcc)2, —NRbbP(═O)(N(Rbb)2)2, —P(Rcc)2, —P(ORcc)2, —P(Rcc)3+X—, —P(ORcc)3+X—, —P(Rcc)4, —P(ORcc)4, —OP(Rcc)2, —OP(Rcc)3+X—, —OP(ORcc)2, —OP(ORcc)3+X—, —OP(Rcc)4, —OP(ORcc)4, —B(Raa)2, —B(ORcc)2, —BRaa(ORcc), C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 Rdd groups; wherein X— is a counterion;

or two geminal hydrogens on a carbon atom are replaced with the group ═O, ═S, ═NN(Rbb)2, =NNRbbC(═O)Raa, =NNRbbC(═O)ORaa, =NNRbbS(═O)2Raa, ═NRbb, or ═NORcc;

each instance of Raa is, independently, selected from C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Raa groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rbb is, independently, selected from hydrogen, —OH, —ORaa, —N(Rcc)2, —CN, —C(═O)Raa, —C(═O)N(Rcc)2, —CO2Raa, —SO2Raa, —C(═NRcc)ORaa, —C(═NRcc)N(Rcc)2, —SO2N(Rcc)2, —SO2Rcc, —SO2ORcc, —SORaa, —C(═S)N(Rcc)2, —C(═O)SRcc, —C(═S)SRcc, —P(═O)(Raa)2, —P(═O)(ORcc)2, —P(═O)(N(Rcc-')2)2, C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rbb groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups; wherein X— is a counterion;

each instance of Rcc is, independently, selected from hydrogen, C1-10 alkyl, C1-10 perhaloalkyl, C2-10 alkenyl, C2-10 alkynyl, C3-10 carbocyclyl, 3-14 membered heterocyclyl, C6-14 aryl, and 5-14 membered heteroaryl, or two Rcc groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups;

each instance of Rdd is, independently, selected from halogen, —CN, —NO2, —N3, —SO2H, —SO3H, —OH, —ORee, —ON(Rff)2, —N(Rff)2, —N(Rff)3+X—, —N(ORee)Rff, —SH, —SRee, —SSRee, —C(═O)Ree, —CO2H, —CO2Ree, —OC(═O)Ree, —OCO2Ree, —C(═O)N(Rff)2, —OC(═O)N(Rff)2, —NRffC(═O)Ree, —NRffCO2Ree, —NRffC(═O)N(Rff)2, —C(═NRff)ORee, —OC(═NRff)Ree, —OC(═NRff)ORee, —C(═NRff)N(Rff)2, —OC(═NRff)N(Rff)2, —NRffC(═NRff)N(Rff)2, —NRffSO2Ree, —SO2N(Rff)2, —SO2Ree, —SO2ORee, —OSO2Ree, —S(═O)Ree, —Si(Ree)3, —OSi(Ree)3, —C(═S)N(Rff)2, —C(═O)SRee, —C(═S)SRee, —SC(═S)SRee, —P(═O)(ORee)2, —P(═O)(Ree)2, —OP(═O)(Ree)2, —OP(═O)(ORee)2, C1-6 alkyl, C1-6 perhaloalkyl, C2-6 alkenyl, C2-6 alkynyl, C3-10 carbocyclyl, 3-10 membered heterocyclyl, C6-10 aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups, or two geminal Rdd substituents can be joined to form ═O or ═S; wherein X— is a counterion;

each instance of Ree is, independently, selected from C1-6 alkyl, C1-6 perhaloalkyl, C2-6 alkenyl, C2-6 alkynyl, C3-10 carbocyclyl, C6-10 aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 Rgg groups;

each instance of Rff is, independently, selected from hydrogen, C1-6 alkyl, C1-6 perhaloalkyl, C2-6 alkenyl, C2-6 alkynyl, C3-10 carbocyclyl, 3-10 membered heterocyclyl, C6-10 aryl and 5-10 membered heteroaryl, or two Rff groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rgg groups; and each instance of Rgg is, independently, halogen, —CN, —NO2, —N3, —SO2H, —SO3H, —OH, —OC1-6 alkyl, —ON(C1-6 alkyl)2, —N(C1-6 alkyl)2, —N(C1-6 alkyl)3+X—, —NH(C1-6 alkyl)2+X—, —NH2(C1-6 alkyl)+X—, —NH3+X—, —N(OC1-6 alkyl)(C1-6 alkyl), —N(OH)(C1-6 alkyl), —NH(OH), —SH, —SC1-6 alkyl, —SS(C1-6 alkyl), —C(═O)(C1-6 alkyl), —CO2H, —CO2(C1-6 alkyl), —OC(═O)(C1-6 alkyl), —OCO2(C1-6 alkyl), —C(═O)NH2, —C(═O)N(C1-6 alkyl)2, —OC(═O)NH(C1-6 alkyl), —NHC(═O)(C1-6 alkyl), —N(C1-6 alkyl)C(═O)(C1-6 alkyl), —NHCO2(C1-6 alkyl), —NHC(═O)N(C1-6 alkyl)2, —NHC(═O)NH(C1-6 alkyl), —NHC(═O)NH2, —C(═NH)O(C1-6 alkyl), —OC(═NH)(C1-6 alkyl), —OC(═NH)OC1-6 alkyl, —C(qNH)N(C1-6 alkyl)2, —C(═NH)NH(C1-6 alkyl), —C(═NH)NH2, —OC(═NH)N(C1-6 alkyl)2, —OC(NH)NH(C1-6 alkyl), —OC(NH)NH2, —NHC(NH)N(C1-6 alkyl)2, —NHC(═NH)NH2, —NHSO2(C1-6 alkyl), —SO2N(C1-6 alkyl)2, —SO2NH(C1-6 alkyl), —SO2NH2, —SO2C1-6 alkyl, —SO2OC1-6 alkyl, —OSO2C1-6 alkyl, —SOC1-6 alkyl, —Si(C1-6 alkyl)3, —OSi(C1-6 alkyl)3 —C(═S)N(C1-6 alkyl)2, C(═S)NH(C1-6 alkyl), C(═S)NH2, —C(═O)S(C1-6 alkyl), —C(═S)SC1-6 alkyl, —SC(═S)SC1-6 alkyl, —P(═O)(OC1-6 alkyl)2, —P(═O)(C1-6 alkyl)2, —OP(═O)(C1-6 alkyl)2, —OP(═O)(OC1-6 alkyl)2, C1-6 alkyl, C1-6 perhaloalkyl, C2-6 alkenyl, C2-6 alkynyl, C3-10 carbocyclyl, C6-10 aryl, 3-10 membered heterocyclyl, 5-10 membered heteroaryl; or two geminal Rgg substituents can be joined to form ═O or ═S; wherein X— is a counterion.

each instance of Rgg is, independently, halogen, —CN, —NO2, —N3, —SO2H, —SO3H, —OH, —OC1-6 alkyl, —ON(C1-6 alkyl)2, —N(C1-6 alkyl)2, —N(C1-6 alkyl)3+X—, —NH(C1-6 alkyl)2+X—, —NH2(C1-6 alkyl)+X—, —NH3+X—, —N(OC1-6 alkyl)(C1-6 alkyl), —N(OH)(C1-6 alkyl), —NH(OH), —SH, —SC1-6 alkyl, —SS(C1-6 alkyl), —C(═O)(C1-6 alkyl), —CO2H, —CO2(C1-6 alkyl), —OC(═O)(C1-6 alkyl), —OCO2(C1-6 alkyl), —C(═O)NH2, —C(═O)N(C1-6 alkyl)2, —OC(═O)NH(C1-6 alkyl), —NHC(═O)(C1-6 alkyl), —N(C1-6 alkyl)C(═O)(C1-6 alkyl), —NHCO2(C1-6 alkyl), —NHC(═O)N(C1-6 alkyl)2, —NHC(═O)NH(C1-6 alkyl), —NHC(═O)NH2, —C(═NH)O(C1-6 alkyl), —OC(═NH)(C1-6 alkyl), —OC(═NH)OC1-6 alkyl, —C(═NH)N(C1-6 alkyl)2, —C(═NH)NH(C1-6 alkyl), —C(═NH)NH2, —OC(═NH)N(C1-6 alkyl)2, —OC(NH)NH(C1-6 alkyl), —OC(NH)NH2, —NHC(NH)N(C1-6 alkyl)2, —NHC(═NH)NH2, —NHSO2(C1-6 alkyl), —SO2N(C1-6 alkyl)2, —SO2NH(C1-6 alkyl), —SO2NH2, —SO2C1-6 alkyl, —SO2OC1-6 alkyl, —OSO2C1-6 alkyl, —SOC1-6 alkyl, —Si(C1-6 alkyl)3, —OSi(C1-6 alkyl)3 —C(═S)N(C1-6 alkyl)2, C(═S)NH(C1-6 alkyl), C(═S)NH2, —C(═O)S(C1-6 alkyl), —C(═S)SC1-6 alkyl, —SC(═S)SC1-6 alkyl, —P(═O)(OC1-6 alkyl)2, —P(═O)(C1-6 alkyl)2, —OP(═O)(C1-6 alkyl)2, —OP(═O)(OC1-6 alkyl)2, C1-6 alkyl, C1-6 perhaloalkyl, C2-6 alkenyl, C2-6 alkynyl, C3-10 carbocyclyl, C6-10 aryl, 3-10 membered heterocyclyl, 5-10 membered heteroaryl; or two geminal Rgg substituents can be joined to form ═O or ═S; wherein X— is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F—, Cl—, Br—, I—), NO3-, ClO4-, OH—, H2PO4-, HSO4-, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF4-, PF4-, PF6-, AsF6-, SbF6-, B[3,5-(CF3)2C6H3]4]—, BPh4-, Al(OC(CF3)3)4-, and a carborane anion (e.g., CB11H12- or (HCB11Me5Br6)-). Exemplary counterions which may be multivalent include CO32-, HPO42-, PO43-, B4O72-, SO42-, S2O32-, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

In specific examples, the neuroceutical in the salts disclosed herein can be clozapine, olanzapine, quetiapine, risperidone, paliperidone, lurasidone or gabapentin. In another embodiment, the neuroceutical comprises only one of clozapine, olanzapine, quetiapine, risperidone, paliperidone, lurasidone or gabapentin.

(ii) Acids

The acids for use in making the salts of neuroceuticals disclosed herein can be benzoic acid, nicotinic acid, pantothenic acid, or tannic acid.

Structures (provided in the table below) of benzoic acid, nicotinic acid, and pantothenic acid are well known in the art.

| Acid | Structure |
| --- | --- |
| Benzoic acid | 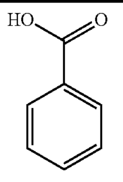 |
| Nicotinic acid | 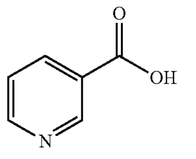 |
| Pantothenic acid | 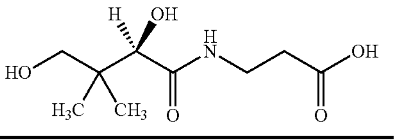 |

The benzoic acid, nicotinic acid, or pantothenic acid for use in making the salt of neuroceuticals disclosed herein may be unsubstituted. Alternatively, it may be substituted by one or more permissible substituents such as those described herein.

Tannic acid refers to a type of polyphenol including a glucose in the central surrounded by poly-galloyl (gallic acid) moieties. Naturally-occurring tannic acids are a mixture of poly-galloyl glucoses, including, e.g., 2-12 2 gallic acid units. Tannic acids having a defined number of gallic acid moieties can be purified from a natural source or prepared by chemical synthesis.

The structure of an exemplary tannic acid (having 10 galloyl moieties) is provided below:

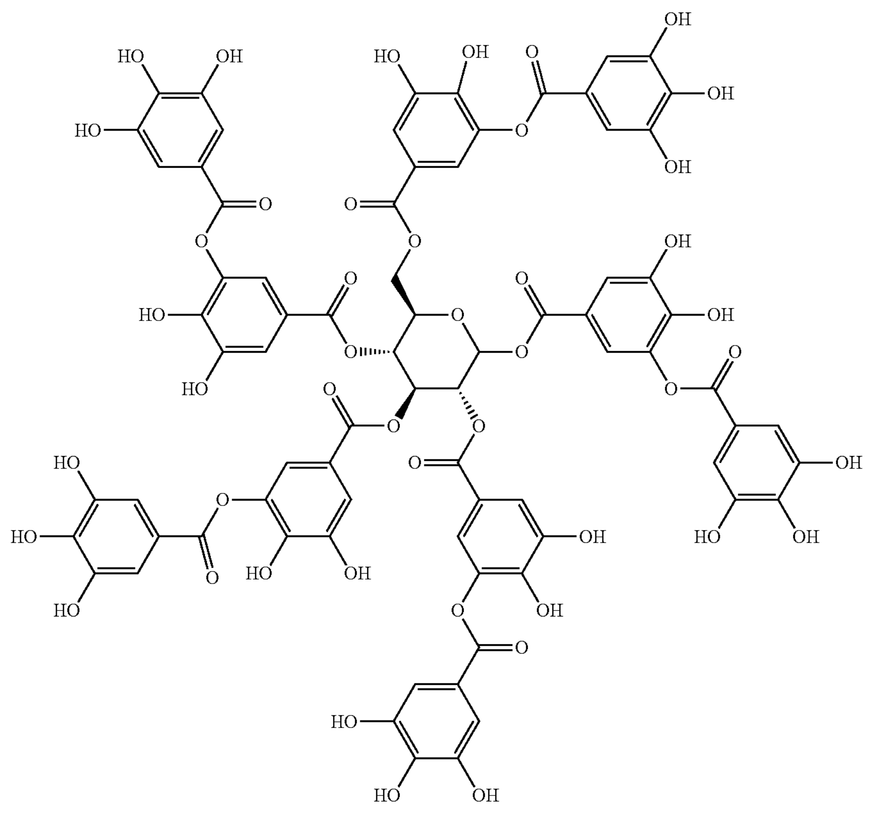 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]

Tannins are a group of naturally occurring compounds that exist in various plants, for example, *Rhus chinensis, Rhus javanica, Rhus semialata, Rhus coriaria, Rhus potaninii, Rhus punjabensis* var. *sinica* (Diels) Rehder & E. H. Wilson, *Camellia sinensis*, Berry, *Bixa orellana, Vitis vinifera, Punica granatum, Quercus infectoria, Quercus cerris, Acacia mearnsii, Pseudotsuga menziesii, Caesalpinia spinosa, Fagus hayata Palib.* ex *Hayata*, or *Machilus thunbergii* Sieb. & Zucc. etc. There are three major classes of tannins, including hydrolysable tannins (also known as tannic acids), condensed tannins, and phlorotannins, which contain gallic acid, flavone, and phloroglucinol, respectively, as the base unit. Tannins are widely used as a type of industrial particleboard adhesive and for production of anti-corrosive primer or resins. It was also suggested that tannins may have various effects on human health.

In some examples, the mixture of tannic acids in the composition comprises tannic acids having 4-12 galloyl moieties (e.g., 5-10 galloyl moieties, 5-12 galloyl moieties, or 8-12 galloyl moieties). In some examples, the mixture of tannic acids constitutes at least 95% by weight of the total tannic acid content in the composition. In some examples, the tannic acids described herein are the only tannic acid content in the composition.

In some embodiments, the tannic acid composition described herein may comprise no more than 20% (e.g., <15%, <10% or <5%) of tannic acids having 1-5 galloyl moieties. Alternatively or in addition, the tannic acid composition may comprise at least 50% (e.g., >60%, >70%, or >80%) tannic acids having 6-12 galloyl moieties (e.g., 8-12 galloyl moieties).

In some embodiments, the tannic acid composition described herein comprises (i) a mixture of tannic acids or an acceptable salt thereof, and (ii) a carrier, wherein the composition is substantially free of tannic acids having less than four galloyl moieties. In some examples, ≥98% of the tannic acids in the composition have 4-12 galloyl moieties. In some examples, ≥95% (e.g., ≥97%) of the tannic acids in the composition have 5-12 galloyl moieties. In some examples, ≥90% of the tannic acids in the composition have 6-12 galloyl moieties. In some examples, ≥60% of the tannic acids in the composition have 8-12 galloyl moieties. In one particular example, the composition comprises about 4-20% of the tannic acids having 5 galloyl moieties, about 10-35% of the tannic acids having 6-7 galloyl moieties, and about 55-85% of the tannic acids having 8-12 galloyl moieties.

In some examples, the tannic acid disclosed herein contains a center glucose moiety in β form. In other examples, the tannic acid disclosed herein contains a center glucose moiety in β form. In some examples, the tannic acid contains 4 gallic acid units surrounding the center glucose moiety. In some examples, the tannic acid contains 5 gallic acid units surrounding the center glucose moiety. In some examples, the tannic acid contains 6 gallic acid units surrounding the center glucose moiety. In some examples, the tannic acid contains 7 gallic acid units surrounding the center glucose moiety. In some examples, the tannic acid contains 8 gallic acid units surrounding the center glucose moiety. In some examples, the tannic acid contains 9 gallic acid units surrounding the center glucose moiety. In some examples, the tannic acid contains 10 gallic acid units surrounding the center glucose moiety. In some examples, the tannic acid contains 11 gallic acid units surrounding the center glucose moiety. In some examples, the tannic acid contains 12 gallic acid units or more surrounding the center glucose moiety.

In another aspect, the tannic acid composition disclosed comprises (i) a tannic acid or an acceptable salt thereof, and (ii) a carrier, wherein the tannic acid contains 4, 5, 6, 7, 8, 9, 10, 11, or 12 galloyl moieties. The tannic acid may constitute at least 90% (w/w) of the total tannic acid content in the composition. In some examples, the tannic acid constitutes at least 95% by weight of the total tannic acid content in the composition.

(iii) Salts of a Neuroceutical and an Acid

The salts of neuroceuticals disclosed herein may comprise any of the neuroceuticals disclosed herein and an acid, which can be benzoic acid, nicotinic acid, pantothenic acid, or tannic acid. In some embodiments, the neuroceutical is a substituted benzodiazepine, a substituted benzothiazepine, a substituted pyridopyrimidines or a substituted amino-cyclohexaneacetic acid, e.g., any of the exemplary compounds disclosed herein. The molar ratio of the neuroceutical and the acid can range from about 6:1 to about 1:5.

Exemplary salts of neuroceuticals disclosed herein include clozapine benzoic acid, clozapine nicotinic acid, clozapine tannic acid, olanzapine nicotinic acid, olanzapine pantothenic acid, olanzapine tannic acid, quetiapine nicotinic acid, risperidone nicotinic acid, paliperidone benzoic acid, paliperidone nicotinic acid, gabapentin tannic acid, and sarcosine tannic acid.

In some embodiments, the salt disclosed herein contains a neuroceutical and an acid at a molar ratio of 1:1. In some examples, the acid can be benzoic acid and the neuroceutical can be clozapine. In some examples, the acid can be benzoic acid and the neuroceutical can be paliperidone. In some examples, the acid can be benzoic acid and the neuroceutical can be lurasidone. In other examples, the acid can be nicotinic acid and the neuroceutical can be clozapine. Alternatively, the acid can be nicotinic acid and the neuroceutical can be olanzapine. In yet other examples, the acid can be nicotinic acid and the neuroceutical can be quetiapine. In still other examples, the acid can be nicotinic acid and the neuroceutical can be risperidone. In yet other examples, the acid can be a tannic acid and the neuroceutical can be gabapentin.

In specific example, the salt disclosed herein is a salt of clozapine and of benzoic acid (e.g., at a molar ratio of 1:1). Such a salt may be in a solid form. In some instances, the solid form can be characterized by a powder X-ray diffraction pattern comprising peaks at approximately 7.6, 12.4, 13.6, 15.3, 15.7, 16.0, 19.5, 19.9, 23.1, 24.9, 25.1, 28.4 degrees 2-theta.

In another specific example, the salt disclosed herein is a salt of clozapine and nicotinic acid (e.g., at a molar ratio of 1:1). Such a salt may be in a solid form. In some instances, the solid form can be characterized by a powder X-ray diffraction pattern comprising peaks at approximately 7.7, 8.2, 10.9, 12.6, 13.8, 16.0, 17.9, 18.2, 18.8, 19.5, 21.9, 22.2, 22.4, 23.3, 24.1, 25.2, 31.2, 31.5, 35.0, 44.2 degrees 2-theta.

In yet another specific example, the salt disclosed herein is a salt of olanzapine and nicotinic acid (e.g., at a molar ratio of 1:1). Such a salt may be in a solid form. In some instances, the solid form can be characterized by a powder X-ray diffraction pattern comprising peaks at approximately 7.9, 8.1, 9.6, 13.7, 15.8, 16.4, 17.2, 17.9, 19.3, 24.3, 29.4, 33.1, 34.6, 39.4, 42.7 degrees 2-theta.

In still another specific example, the salt disclosed herein is a salt of quetiapine and nicotinic acid (e.g., at a molar ratio of 1:1). Such a salt may be in a solid form. In some instances, the solid form may be characterized by a powder X-ray diffraction pattern comprising peaks at approximately 6.2, 9.2, 10.3, 11.4, 12.4, 12.9, 16.2, 16.5, 17.0, 17.2, 17.3, 17.5, 19.4, 19.9, 21.1, 21.3, 22.1, 27.1, 32.9, 35.6 degrees 2-theta.

In addition, the salt disclosed herein may be a salt of risperidone and nicotinic acid (e.g., at a molar ratio of 1:1). Such a salt may be in a solid form. In some instances, the solid form may be characterized by a powder X-ray diffraction pattern comprising peaks at approximately 9.7, 10.9, 12.0, 12.4, 14.4, 17.1, 17.4, 24.4, 36.8, 42.8, 44.1 degrees 2-theta.

Further, the salt disclosed herein is a salt of paliperidone and benzoic acid (e.g., at a molar ratio of 1:1). Such a salt may be in a solid form. In some instances, the solid form can be characterized by a powder X-ray diffraction pattern comprising peaks at approximately 6.8, 9.0, 10.9, 11.4, 11.8, 16.6, 18.3, 18.6, 20.8, 22.2, 22.8, 27.5, 29.0, 30.3, 32.3 degrees 2-theta.

In some embodiments, the salts disclosed herein contains a neuroceutical and an acid at a molar ratio of 1:2 (neuroceutical:acid). In some examples, the neuroceutical can be clozapine and the acid can be tannic acid. In other examples, the neuroceutical can be olanzapine and the acid can be tannic acid. Alternatively, the neuroceutical can be gabapentin and the acid can be tannic acid. In other examples, or the neuroceutical can be sarcosine and the acid can be tannic acid. In some examples, the neuroceutical can be paliperidone and the acid can be nicotinic acid.

In one specific example, the salt disclosed herein contains paliperidone and nicotinic acid (e.g., at a moral ratio of 1:2). Such a salt may be in a solid form. In some instances, the solid form can be characterized by a powder X-ray diffraction pattern comprising peaks at approximately 6.7, 8.9, 11.0, 11.2, 11.7, 16.1, 16.4, 17.6, 18.4, 22.8, 27.2, 29.9 degrees 2-theta.

In some embodiments, the salts disclosed herein contains a neuroceutical and an acid at a molar ratio of 1:3 (neuroceutical:acid). In some examples, the acid can be a tannic acid and the neuroceutical can be gabapentin.

In some embodiments, the salts disclosed herein contains a neuroceutical and an acid at a molar ratio of 2:1 (neuroceutical:acid). In some examples, the acid can be a tannic acid and the neuroceutical can be clozapine. In other examples, the acid can be a tannic acid and the neuroceutical can be olanzapine. In yet other examples, the acid can be a tannic acid and the neuronceutical can be gabapentin.

In some embodiments, the salts disclosed herein contains a neuroceutical and an acid at a molar ratio of 3:1 (neuroceutical:acid). In some examples, the acid can be a tannic acid and the neuroceutical can be gabapentin.

In some embodiments, the salts disclosed herein contains a neuroceutical and an acid at a molar ratio of 4:1 (neuroceutical:acid). In some examples, the acid can be a tannic acid and the neuroceutical can be clozapine.

In an embodiment, the salts disclosed herein contains a neuroceutical and an acid at a molar ratio of 5:1 (neuroceutical:acid). In some examples, the acid can be pantothenic acid and the neuroceutical can be olanzapine. In specific examples, the salt contains olanzapine and pantothenic acid at the molar ratio of 5:1, wherein such a salt may be in a solid form. In some instances, the solid form may have a powder X-ray diffraction pattern, which comprises characteristic peaks at a reflection angel 2 theta of approximately 7.7, 8.1, 8.7, 11.2, 11.7, 13.5, 15.4, 16.0, 16.2, 16.4, 19.0, 20.3, 22.2, 22.4, 23.1, 24.4, 25.7, 25.8, 26.7, 27.7, 29.4, 33.6, 34.3, 34.6, 37.7 degrees 2-theta.

II. Compositions Comprising Salts of Neuroceuticals

The salts of neuroceuticals as described herein may be formulated into a composition, which may be in a variety of different forms, including nutraceutical compositions, pharmaceutical compositions, health foods, health food products, medical foods, and/or medical food products.

The compositions, foods and food products described herein also facilitate the treatment of any of the target diseases noted herein (e.g., neuropsychiatric disorders and/or a bacterial infections (e.g., tuberculosis) including those described herein).

In one embodiment, the neuroceutical salt is in the form of a health food product, which may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

In some embodiments, the health food product is a nutraceutical composition. A nutraceutical composition comprises any of the neuroceutical salts, described herein, in combination with any additional ingredients and supplements that promote good health and/or enhance the stability and/or bioactivity of the neuroceutical salt.

The biological activity of the compositions, foods and products may be fast and/or short-term, i.e., begin to improve the health of the human or animal within minutes of ingesting the compositions, food and products or may help achieve long-term health objectives as those described herein, e.g., improving basic behavioral functioning, hyperactivity, anxiety, depression, sensorimotor gating, pain threshold, memory and/or cognitive functioning in, e.g., subjects that are at risk for developing a neuropsychiatric disorder. The compositions, foods and products may be contained in an edible material, for example, as a dietary supplement or a pharmaceutical formulation. As a dietary supplement, additional nutrients, such as vitamins, minerals or amino acids may also be included. The composition can also be in the form of a drink. Examples of food products and drinks include tea, soft drink, juice, milk, coffee, cookie, cereal, chocolate, and snack bar. If desired, the compositions, foods and products can be sweetened by adding a sweetener. Non-limiting examples of sweeteners include such as sorbitol, maltitol, hydrogenated glucose syrup and hydrogenated starch hydrolyzate, high fructose corn syrup, cane sugar, beet sugar, pectin, or sucralose.

In an embodiment, liquid preparations of the compositions, foods and products for oral administration can take the form of, for example, solutions, syrups or suspensions, or they can be presented as a dry product for constitution with water or other suitable vehicles, before use. In one embodiment, the liquid preparations can be formulated for administration with fruit juice.

In certain embodiments, the composition is a medical food or medical food product. In some embodiments, a medical food is not a food that would be simply recommended by a physician as part of an overall diet, to manage the symptoms or reduce the risk of a disease or condition.

In certain embodiments, a therapeutically effective amount of a neuroceutical salt is in the form of a pharmaceutical composition. In certain embodiments, the effective amount is a therapeutically effective amount (e.g., amount effective for treating and/or reducing the risk for a CNS disorder, e.g., those disclosed herein.

Pharmaceutical compositions described herein can be prepared by any method known in the art of pharmacology. In general, such preparatory methods include bringing the salt described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Pharmaceutical compositions may be formulated as an injectable preparation. Examples include sterile injectable aqueous or oleaginous suspensions, which are known in the art. The sterile injectable preparation can be a sterile injectable solution, suspension, or emulsion in a nontoxic parenterally acceptable diluent or solvent, for example, in 1,3-butanediol. In one embodiment, the pharmaceutical compositions form solutions in 1,3-butanediol. Other acceptable vehicles and solvents include water, Ringer's solution, U.S.P., and isotonic sodium chloride solution. Additionally, sterile, fixed oils may be used as a solvent or suspending medium. Examples of fixed oils include synthetic mono- or di-glycerides. Fatty acids, such as oleic acid, may also be used in the preparation of the injectable formulations.

The injectable formulations can be sterilized, for example, by filtering the formulation through a bacterial-retaining filter, or by incorporating solid sterilizing agents, which can be dissolved or dispersed in sterile water or other sterile injectable medium, prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient (any of the salts disclosed herein) can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

III. Method of Treatment

In some aspect, the present disclosure features a method for treating a CNS disorder using any of the compositions disclosed herein, which comprise any of the salts of neuroceuticals as also disclosed herein. To perform such a method, an effective amount of can be administered to a subject in need of the treatment via a suitable route. In some embodiments, the subject can be a human patient having or at risk for the CNS disorder.

The neuroceutical compositions, foods and products disclosed herein can be administered by any route, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of the neuroceutical salt to be administered to a human or animal in need of such treatment will vary from subject to subject, depending, for example, on species, age, general condition of a subject, the severity of the side effects or disorder, the identity of the particular the neuroceutical salt, the mode of administration, and the like. An effective amount may be included in a single dose (e.g., single oral dose) or multiple doses (e.g., multiple oral doses). In certain embodiments, when multiple doses are administered to a subject or applied to a biological sample, such as a tissue or cell, any two doses of the multiple doses may include different or substantially the same amounts of the neuroceutical salt. In certain embodiments, when multiple doses are administered to a subject or applied to a biological sample, the frequency of administering the multiple doses is typically three doses a day, two doses a day, one dose a day, one dose every other day, one dose every third day, one dose every week, one dose every other week, one dose monthly or one dose every other month. In certain embodiments, the frequency of administering the multiple doses is one dose per day. In certain other embodiments, the frequency of administering the multiple doses is two doses per day. In yet other embodiments, when multiple doses are administered, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject or biological sample. In certain embodiments, the duration between the first dose and last dose of the multiple doses is three months, six months, or one year. In certain embodiments, the duration between the first dose and last dose of the multiple doses is the lifetime of the subject or biological sample.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In some embodiments, the effective dose of the composition, food, food product or the neuroceutical salt is between about 0.1 and about 1500 mg/kg (body weight), or between 0.5 and 1 mg/kg, or between 1 and 3 mg/kg, or between 3 and 5 mg/kg, or between 5 and 8 mg/kg, or between 8 and 12 mg/kg, or between 12 and 17 mg/kg, or between 17 and 22 mg/kg, or between 22 and 30 mg/kg, or between 30 and 40 mg/kg, or between 40 and 50 mg/kg, or between 50 and 100 mg/kg, or between 100 and 200 mg/kg, or between 200 and 400 mg/kg, or between 400 and 700 mg/kg, or between 700 and 1000 mg/kg, or between 1000 and 1500 mg/kg, or between 1500 mg/kg and 3 g/kg, or between 3 g/kg and 10 g/kg, or between 10 g/kg and 30 g/kg, or between 30 g/kg and 100 g/kg.

In some embodiments, the effective dose of clozapine benzoic acid salt is between about 10 and about 1500 mg, or between 10 and 30 mg, or between 30 and 50 mg, or between 50 and 100 mg, or between 100 and 200 mg, or between 200 and 400 mg, or between 400 and 700 mg, or between 700 and 1000 mg, or between 1000 and 1500 mg.

In some embodiments, the effective dose of clozapine nicotinic acid salt is between about 10 and about 1500 mg, or between 10 and 30 mg, or between 30 and 50 mg, or between 50 and 100 mg, or between 100 and 200 mg, or between 200 and 400 mg, or between 400 and 700 mg, or between 700 and 1000 mg, or between 1000 and 1500 mg.

In some embodiments, the effective dose of clozapine tannic acid salt is between about 10 mg and about 10 g, or between 10 mg and 300 mg, or between 300 mg and 1 g, or between 1 g and 3 g, or between 3 g 10 g.

In some embodiments, the effective dose of olanzapine nicotinic acid salt is between about 5 and about 50 mg, or between 5 and 10 mg, or between 10 and 20 mg, or between 20 and 30 mg, or between 30 and 50 mg.

In some embodiments, the effective dose of olanzapine pantothenic acid salt is between about 10 and about 150 mg, or between 10 and 20 mg, or between 20 and 30 mg/kg, or between 30 and 50 mg, or between 50 and 70 mg, or between 70 and 100 mg/kg, or between 100 and 150 mg.

In some embodiments, the effective dose of olanzapine tannic acid salt is between about 5 and about 500 mg, or between 5 and 30 mg, or between 30 and 100 mg, or between 100 and 300 mg, or between 300 and 500 mg.

In some embodiments, the effective dose of quetiapine nicotinic acid salt is between about 50 and about 1500 mg, or between 50 and 100 mg, or between 100 and 200 mg, or between 200 and 400 mg, or between 400 and 700 mg, or between 700 and 1000 mg, or between 1000 and 1500 g.

In some embodiments, the effective dose of risperidone nicotinic acid salt is between about 0.5 and about 50 mg, or between 0.5 and 1 mg, or between 1 and 3 mg, or between 3 and 5 mg, or between 5 and 8 mg, or between 8 and 12 mg, or between 12 and 17 mg, or between 17 and 22 mg, or between 22 and 30 mg, or between 30 and 40 mg, or between 40 and 50 mg.

In some embodiments, the effective dose of paliperidone benzoic acid salt is between about 2 and about 30 mg, or between 2 and 3 mg, or between 3 and 5 mg, or between 5 and 10 mg, or between 10 and 20 mg, or between 20 and 30 mg.

In some embodiments, the effective dose of paliperidone nicotinic acid salt is between about 2 and about 30 mg, or between 2 and 3 mg, or between 3 and 5 mg, or between 5 and 10 mg, or between 10 and 20 mg, or between 20 and 30 mg.

In some embodiments, the effective dose of gabapentin tannic acid salt is between about 100 mg and about 100 g, or between 100 mg and 300 mg, or between 300 mg and 1 g, or between 1 g and 5 g, or between 5 g 10 g, or between 10 g 30 g, or between 30 g 100 g.

In some embodiments, the effective dose of sarcosine tannic acid salt is between about 1 g and about 200 g, or between 1 g and 10 mg, or between 10 g and 30 g, or between 30 g and 50 g, or between 50 g 100 g, or between 100 g and 200 g.

In some embodiments, the subject receiving treatment has, is suspected of having or is at risk for developing a neuropsychiatric disorder.

The neuroceutical salts disclosed herein, or the compositions, foods and products described herein are useful in treating and/or preventing a human or animal from developing a neuropsychiatric disorder.

In some embodiments, the neuropsychiatric disorder can be schizophrenia, psychotic disorder, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorder, attention deficit disorder, obsessive compulsive disorder, tic disorder, childhood learning disorder, premenstrual syndrome, depression, major depressive disorder, anhedonia, suicidal ideation and/or behavior, bipolar disorder, anxiety disorder, panic disorder, post-traumatic stress disorder, chronic mild and unpredictable stress, eating disorder, addiction disorder, personality disorder, Parkinson's disorder, Huntington's disorder, multiple sclerosis, amyotrophic lateral sclerosis, ataxia, Friedreich's ataxia, Tourette's syndrome, nocturnal enuresis, non-epileptic seizure, blepharospasm, Duchenne muscular dystrophy, stroke, chronic pain, neuropathic pain, hyperalgesia, allodynia, diabetic polyneuropathy, chronic pain syndrome, seizures and epilepsy.

In certain embodiments, the neuropsychiatric disorder is schizophrenia. In certain embodiments, the neuropsychiatric disorder is a psychotic disorder. In certain embodiments, the neuropsychiatric disorder is Alzheimer's disease. In certain embodiments, the neuropsychiatric disorder is frontotemporal dementia. In certain embodiments, the neuropsychiatric disorder is vascular dementia. In certain embodiments, the neuropsychiatric disorder is dementia with Lewy bodies. In certain embodiments, the neuropsychiatric disorder is senile dementia. In certain embodiments, the neuropsychiatric disorder is mild cognitive impairment. In certain embodiments, the neuropsychiatric disorder is benign forgetfulness. In certain embodiments, the neuropsychiatric disorder is closed head injury. In certain embodiments, the neuropsychiatric disorder is autistic spectrum disorder including Asperger's disorder. In certain embodiments, the neuropsychiatric disorder is fragile X syndrome. In certain embodiments, the neuropsychiatric disorder is an attention deficit hyperactivity disorder. In certain embodiments, the neuropsychiatric disorder is attention deficit disorder. In certain embodiments, the neuropsychiatric disorder is an obsessive compulsive disorder. In certain embodiments, the neuropsychiatric disorder is a tic disorder. In certain embodiments, the neuropsychiatric disorder is a childhood learning disorder. In certain embodiments, the neuropsychiatric disorder is premenstrual syndrome. In certain embodiments, the neuropsychiatric disorder is depression, including dysthymia and bereavement. In certain embodiments, the neuropsychiatric disorder is major depressive disorder. In certain embodiments, the neuropsychiatric disorder is anhedonia. In certain embodiments, the neuropsychiatric disorder is suicidal ideation and/or behavior. In certain embodiments, the neuropsychiatric disorder is bipolar disorder including bipolar I and II disorders. In certain embodiments, the neuropsychiatric disorder is an anxiety disorder including panic and phobic disorders. In certain embodiments, the neuropsychiatric disorder is panic disorder. In some embodiments, the neuropsychiatric disorder is post-traumatic stress disorder. In certain embodiments, the neuropsychiatric disorder is chronic mild and unpredictable stress. In certain embodiments, the neuropsychiatric disorder is an eating disorder including bulimia and anorexia. In certain embodiments, the neuropsychiatric disorder is an addiction disorder including substance dependence or abuse. In certain embodiments, the neuropsychiatric disorder is a personality disorder. In certain embodiments, the neuropsychiatric disorder is Parkinson's disorder. In certain embodiments, the neuropsychiatric disorder is Huntington's disorder. In certain embodiments, the neuropsychiatric disorder is multiple sclerosis. In certain embodiments, the neuropsychiatric disorder is amyotrophic lateral sclerosis. In certain embodiments, the neuropsychiatric disorder is Tourette's syndrome. In certain embodiments, the neuropsychiatric disorder is nocturnal enuresis. In certain embodiments, the neuropsychiatric disorder is non-epileptic seizures. In certain embodiments, the neuropsychiatric disorder is blepharospasm. In certain embodiments, the neuropsychiatric disorder is Duchenne muscular dystrophy. In certain embodiments, the neuropsychiatric disorder is stroke. In certain embodiments, the neuropsychiatric disorder is chronic pain. In certain embodiments, the neuropsychiatric disorder is neuropathic pain, including hyperalgesia and allodynia. In certain embodiments, the neuropsychiatric disorder is diabetic polyneuropathy. In certain embodiments, the neuropsychiatric disorder is chronic pain syndromes. In certain embodiments, the neuropsychiatric disorder is seizures. In certain embodiments, the neuropsychiatric disorder is epilepsy.

In some preferred embodiments, the subject is a human. In other, preferred embodiments, the neuroceutical salt is administered to a human at a frequency of four times a day to one time every three months.

In some embodiments, the invention discloses a composition comprising the neuroceutical salt in combination with at least one additional therapeutic agent that is different from the neuroceutical in the salt. In one embodiment, a human subject has undergone or is treated concurrently with one or more additional therapeutic agents for the CNS disorder, and wherein the one or more therapeutic agents are different from the neuroceutical in the salt. The additional therapeutic agent may be an antipsychotic drug, an antidepressant drug, an analgesic drug, an anticonvulsant drug, or a neurodegeneration drug. In some embodiments, the CNS disorder is a neurodegenerative disease, which is selected from the group consisting of amyotrophic lateral sclerosis, dementia, Alzheimer's disease, Parkinson's disease, and Huntington's disease.

Examples of additional therapeutic agents include, but are not limited to, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, LY2140023, droperidol, pimozide, butaperazine, carphenazine, remoxipride, piperacetazine, sulpiride, acamprosate, tetrabenazine, chlorpromazine, blonanserine, bromperidol, carpipramine, clocapramine, clotiapine, cyamemazine, fluspirilene, haloperidol, iloperidone, loxapine, lurasidone, melperone, molindone, mosapramine, nemonapride, oxypertine, penfluridol, pyrazine, pericyazine, perospirone, pipamperone, pipotiazine, prothipendyl, sertindole, spiperone, sultopride, tiapride, timiperone, zotepine, donepezil, galantamine, memantine, riluzole, rivastigmine, tacrine, bupropion, citalopram, lithium, mirtazapine, nortriptyline, sertraline, triiodothyronine, tranylcypromine, venlafaxine, diazepam, bromazepam, prazepam, chlordiazepoxide, clobazam, estazolam, flurazepam, clonazepam, temazepam, triazolam, alprazolam, midazolam, brotizolam, nitrazepam, flunitrazepam, oxazepam, quazepam, lorazepam, temazepam, triazolam, zolpidem, zopiclone, zaleplon, chlorpromazine, thioridazine, mesoridazine, fluphenazine, perphenazine, trifluoperazine, thiothixene, haloperidol, loxapine, molindone, haloperidol decanoate, fluphenazine decanoate, fluphenazine enanthate, risperdal consta, acetophenazine, chlorprothixene, amitriptyline, imipramine, nortriptiline, protriptyline, desipramine, trimipramine, amoxapine, bupropion sr, citalopram, s-citalopram, clomipramine, desipramine, doxepin, duloxetine, milnacipran, fluoxetine, fluvoxamine, imipramine, isocarboxazid, isoniazid, iproniazid, fluoxetine, paroxetine, sarcosine, sertraline fluvoxamine, venlafaxine, velafaxine xr, milnacipram and duloxetine, mirtazapine, mianserin, reboxetine, selegiline, tranylcypromine, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, physostigmine, nicotine, huperzine alpha, vitamin c, vitamin, carotenoids, *Ginkgo biloba*, statinsamphetamine, modafinil, desoxyn, methamphetamine, cocaine, arecoline, dexmethylphenidate, dextroamphetamine, methylphenidate, lisdexamfetamine dimesylate (vyvanse), mixed salts amphetamine, atomoxetine, clonidine hydrochloride, guanfacine hydrochloride, arecoline, pemoline, lamotrigine, acamprosate, tetrabenazine, riluzole, acetaminophen, aspirin, bromfenac, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, nepafenac, oxaprozin, phenylbutazone, piroxicam, sulindac, tolmetin, celecoxib, lidocaine, nefopam, orphenadrine, cyclobenzaprine, hyoscine, fentanyl, hydrocodone, hydromorphone, levorphanol, meperidine, methadone, oxycodone, oxymorphone, propoxyphene, tapentadol, tramadol, buprenorphine, butorphanol, nalbuphine, pentazocine, acetazolamide, carbamazepine, clobazam, clonazepam, diazepam, divalproex sodium, eslicarbazepine, ethosuximide, ethotoin, felbamate, fosphenytoin, lamotrigine, lacosamide, levetiracetam, mephenytoin, metharbital, methsuximide, methazolamide, oxcarbazepine, phenobarbital, phenytoin, phensuximide, pregabalin, primidone, sodium valproate, stiripentol, tiagabine, topiramate, trimethadione, valproic acid, vigabatrin, zonisamide, xenazine, tereabenazine, baclofen, austedo, lioresal, kemstro, deutetrabenazine, edaravone, acetylcholinesterase (AChE) inhibitors, levodopa, and a monoamine oxidase-B inhibitor.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1. Preparation of Salts of Neuroceuticals

Materials and Methods (i) 1H-NMR

1H Nuclear magnetic resonance (NMR) analysis was performed on Bruker Fourier 400 (Bruker) in deuterated solvents such as d-methanol at 25° C.

(ii) Thermogravimetric Analysis (TGA)

TGA data were measured by TGA Q50 (TA Instruments-Waters LLC) with platinum crucibles with the heating rate of 10° C./min, between 50° C.-700° C.

(iii) Differential Scanning Calorimetry

The melting point of the salt was determined using the differential scanning calorimeter (DSC) method. The DSC data were measured by DSC 25 (TA Instruments-Waters LLC) with T-zero aluminum low-mass pan at the heating rate of 10° C./min and the heating range of 50° C.-450° C.

(iv) X-ray Powder Diffractometry

X-ray diffraction patterns were obtained on D8 ADVANCE (Bruker AXS Gmbh, Germany) Samples were scanned in continuous mode from 0-45° (2θ) with step size of 0.02° on a spinning stage at 40 kV and 40 mA with Cu Kα radiation. The incident beam path was equipped with a 0.2 mm divergence slit and 0.02 mm air scattering screen. The diffracted beam was equipped with Ni-filter. Detection was accomplished with a Lynxeye detector (Bruker AXS).

Salt Preparation (a) Preparation of Clozapine:Benzoic Acid 1:1 Salt

A mixture of clozapine (2.5 g, 7.6 mmol), benzoic acid (0.9 g, 7.6 mmol) and 10.0 mL of EtOH was stirred at 50° C. until all solids dissolved. The mixture was then stirred at 50° C. for 0.5 hr, cooled to RT, and 10.0 mL of hexanes was added. The resulting mixture was stirred at RT overnight, during which a precipitate formed. The precipitate was collected and dried under vacuum at RT for 24 hr to give 2.5 g of clozapine:benzoic acid 1:1 salt. The 1H-NMR, powder X-ray diffraction, and thermoanalysis results of the salt appear in FIGS. 1-4, respectively.

(b) Preparation of Clozapine:Nicotinic Acid 1:1 Salt

A mixture of clozapine (2.0 g, 6.1 mmol), nicotinic acid (3.8 g, 7.6 mmol) and 10.0 mL of acetonitrile and water (94/6) was stirred at 65° C. until all solids dissolved. The mixture was then stirred at 65° C. for 1 hr, cooled to RT and stirred at RT overnight, during which a precipitate formed. The precipitate was collected and dried under vacuum at RT for 6 hr to give 0.8 g of clozapine:nicotinic acid 1:1 salt. The 1H-NMR, powder X-ray diffraction, and thermoanalysis results of the salt appear in FIGS. 5-8, respectively. This salt was used to seed the salt that was made immediately below. A mixture of clozapine (10.0 g, 30.6 mmol), nicotinic acid (3.8 g, 30.6 mmol) and 25.0 mL of acetonitrile and water (94/6) was stirred at 65° C. until all solids dissolved. The mixture was then stirred at 65° C. for 1 h, cooled to RT (room temperature), and seeded with the clozapine:nicotinic acid 1:1 salt from above. After stirring overnight at RT, and a precipitate formed. The precipitate was collected and dried under vacuum at RT for 24 hr to give 9.6 g of clozapine: nicotinic acid 1:1 salt. The 1H-NMR, powder X-ray diffraction, and thermoanalysis results of the salt appear in FIGS. 9-12, respectively.

(c) Preparation of Olanzapine:Nicotinic Acid 1:1 Salt

A mixture of olanzapine (20.0 g, 64.0 mmol), nicotinic acid (7.9 g, 64.0 mmol) and 390.0 mL of acetone and water (87/13) was stirred at 65° C. until all solids dissolved. The mixture was then stirred at 65° C. for 2 hr, cooled to RT and stirred overnight, during which a precipitate formed. The precipitate was collected and dried under vacuum at RT for 24 hr to give 17.8 g of olanzapine:nicotinic acid 1:1 salt. The 1H-NMR, powder X-ray diffraction, and thermoanalysis results of the salt appear in FIGS. 13-16, respectively.

(d) Preparation of Quetiapine:Nicotinic Acid 1:1 Salt

A mixture of quetiapine hydrochloride (2.0 g, 4.8 mmol), sodium nicotinate (0.7 g, 4.8 mmol) and 4.0 mL of water was stirred at 65° C. until all solids dissolved. The mixture was then stirred at 65° C. for 16 hr, cooled to RT, and extracted with ethyl acetate (20.0 mL). The organic layer was separated and concentrated by vacuum. The residue was combined with 10.0 mL of dichloromethane, and the resulting solution was added to 150.0 mL of hexanes. Upon stirring at RT overnight, a precipitate formed. The precipitate was collected, dried under vacuum at RT for 24 hr to give 0.5 g of quetiapine:nicotinic acid 1:1 salt. The 1H-NMR, powder X-ray diffraction, and thermoanalysis results of the salt appearing FIGS. 17-20, respectively.

(e) Preparation of Resperidone:Nicotinic Acid 1:1 Salt

Resperidone (10.0 g, 24.4 mmol), nicotinic acid (3.0 g, 24.4 mmol) and 45.0 mL of acetonitrile and water (49/1) were stirred at 65° C. until all solids dissolved. The mixture was then stirred at 65° C. for 2 hr and cooled to RT. After one day, a precipitate formed. The precipitate was collected and dried under vacuum at RT for 24 hr to afford 9.8 g of resperidone:nicotinic acid 1:1 salt. The 1H-NMR, powder X-ray diffraction, and thermoanalysis results of the salt appear in FIGS. 21-24, respectively.

(f) Preparation of Paliperidone:Benzoic Acid 1:1 Salt

A mixture of paliperidone (2.0 g, 4.7 mmol), benzoic acid (1.1 g, 9.4 mmol) and 10.0 mL of dichloromethane was stirred at 40° C. until all solids dissolved. The mixture was then stirred at 40° C. for 1 hr, cooled to RT, poured into 50.0 mL of hexanes and stirred at RT overnight, during which a precipitate formed. The precipitate was collected, filtered and dried under vacuum at RT for 24 hr to afford 1.9 g of paliperidone:nicotinic acid 1:1 salt. The 1H-NMR, powder X-ray diffraction, and thermoanalysis results of the salt appear in FIGS. 25-28, respectively.

(g) Preparation of Paliperidone:Nicotinic Acid 1:2 Salt

A mixture of paliperidone (2.0 g, 4.7 mmol), nicotinic acid (1.1 g, 9.4 mmol) and 8.4 mL of acetonitrile and water (94/6) was stirred at 65° C. until all solids dissolved. The mixture was then stirred at 65° C. for 2 hr, cooled to RT, and stirred at RT overnight, during which a precipitate formed. The precipitate was collected, and dried under vacuum at RT for 24 hr to afford 2.6 g of paliperidone:nicotinic acid 1:2 salt. The 1H-NMR, powder X-ray diffraction, and thermoanalysis results of the salt appear in FIGS. 29-32, respectively.

(h) Preparation of Olanzapine:Pantothenic Acid 5:1 Salt

A mixture of olanzapine HCl salt (2.0 g, 5.7 mmol), calcium pantothenate (1.4 g, 2.9 mmol) and 10.0 mL of water was stirred at 50° C. until all solids dissolved. The mixture was then stirred at 50° C. for an additional 19 hr. The mixture was added to 50.0 mL of acetone at 50° C. and stirred for 0.5 hr. The mixture was then cooled to RT and stirred for 5 hr, during which a precipitate formed. The precipitate was collected and dried under vacuum at RT for 24 hr to afford 1.0 g of olanzapine:pantothenic acid 5:1 salt. The 1H-NMR, powder X-ray diffraction, and thermoanalysis results of the salt appear in FIGS. 33-36, respectively.

Tannic Acid Salt Preparation

TABLE 1

The Tannic Acid Content in the Enriched Tannic Acid Mixture Used in Salt Preparation

| Tannic acids Content (Number of gallic acids/galloyl) | Proportion (%) |
|---|---|
| 1-4 G | 0-5 |
| 5-12 G | 95-100 |
| 6-12 G | 85-100 |

Methods for preparing tannic acids (e.g., the enriched tannic acid mixture) can be found, e.g., in U.S. Pat. No. 10,105,378, the relevant disclosures of which are incorporated by reference for the purpose and subject matter referenced herein.

(i) Preparation of Clozapine:Enriched Tannic Acid 2:1 Salt

A solution of enriched tannic acid (5.0 g, 3.39 mmol) in acetonitrile (20.0 mL) was added to a solution of clozapine (1.1 g, 3.39 mmol) in acetonitrile (75.0 mL). The resulting mixture was stirred at RT for 2 h, during which a precipitate formed. The precipitate was collected and dried under vacuum at RT for 4 h to afford 4.2 g of clozapine:enriched tannic acid 2:1 salt. The 1H-NMR and thermoanalysis results of the salt appear in FIGS. 37-39, respectively.

(j) Preparation of Clozapine:Enriched Tannic Acid 4:1 Salt

A solution of enriched tannic acid (5.0 g, 3.39 mmol) in acetonitrile (20.0 mL) was added to a solution of clozapine (5.5 g, 16.97 mmol) in acetonitrile (375.0 mL). The resulting mixture was stirred at RT for 2 h, and a precipitate formed. The precipitate was collected and dried under vacuum at RT for 4 h to afford 4.5 g of clozapine:enriched tannic acid 4:1 salt. The 1H-NMR and thermoanalysis results of the salt collected appear in FIGS. 40-42, respectively.

(k) Preparation of Gabapentin:Enriched Tannic Acid 1:1 Salt

A solution of enriched tannic acid (3.0 g, 2.04 mmol) in absolute ethanol (12.0 mL) was added to a 50° C. solution of gabapentin (349 mg, 2.04 mmol) in 95% ethanol solution (30.0 mL). The resulting mixture was cooled to RT and stirred for 2 h, before being slowly added to dichloromethane (840.0 mL). After stirring for 2 h at RT a precipitate formed. The precipitate was collected and dried under vacuum at RT for 4 h to afford 2.4 g of gabapentin:enriched tannic acid 1:1 salt. The 1H-NMR and thermoanalysis results of the salt appear in FIGS. 43-45, respectively.

(l) Preparation of Gabapentin:Enriched Tannic Acid 1:2 Salt

A solution of enriched tannic acid (5.0 g, 3.39 mmol) in absolute ethanol (20.0 mL) was added to a 50° C. solution of gabapentin (291 mg, 1.70 mmol) in 95% ethanol (25.0 mL). The mixture was cooled to RT and stirred for 2 h. The mixture was slowly added to dichloromethane (900.0 mL) and stirred for 2 h at RT, during which a precipitate formed. The precipitate was collected and dried under vacuum at RT for 4 h to afford 4.5 g of gabapentin:enriched tannic acid 1:2 salt. The 1H-NMR and thermoanalysis results of the salt appear in FIGS. 46-48, respectively.

(m) Preparation of Gabapentin:Enriched Tannic Acid 1:3 Salt

A solution of enriched tannic acid (1.0 g, 0.68 mmol) in absolute ethanol (4.0 mL) was added to a 50° C. solution of gabapentin (39 mg, 0.23 mmol) in 95% ethanol (4.0 mL). The mixture was cooled to RT, stirred for 2 h, and then slowly added to dichloromethane (160.0 mL). The resulting mixture was stirred 2 h at RT, during which a precipitate formed. The precipitate was collected and dried under vacuum at RT for 4 h to afford 776 mg of gabapentin: enriched tannic acid 1:3 salt. The 1H-NMR and thermoanalysis results of the salt appear in FIGS. 49-51, respectively.

(n) Preparation of Gabapentin:Enriched Tannic Acid 2:1 Salt

A solution of enriched tannic acid (3.0 g, 2.04 mmol) in absolute ethanol (12.0 mL) was added to a 50° C. solution of gabapentin (697 mg, 4.08 mmol) in 95% ethanol (70.0 mL). The mixture was cooled to RT and stirred for 2 h. The mixture was then slowly added to dichloromethane (1.6 L) and stirred for 2 h at RT, during which a precipitate formed. The precipitate was collected and dried under vacuum at RT for 4 h to afford 2.5 g of gabapentin:enriched tannic acid 2:1 salt. The 1H-NMR and thermoanalysis results of the co-crystal salt appear in FIGS. 52-54, respectively.

(o) Preparation of Gabapentin:Enriched Tannic Acid 3:1 Salt

A solution of enriched tannic acid (3.0 g, 2.04 mmol) in absolute ethanol (12.0 mL) was added to a 50° C. solution of gabapentin (1.05 g, 6.11 mmol) in 95% ethanol (90.0 mL). The mixture was stirred for 2 h as it cooled to RT. The mixture was slowly added to dichloromethane (2.0 L) and stirred for 2 h at RT. The resulting precipitate was collected and dried under vacuum at RT for 4 h to afford 2.6 g of gabapentin:enriched tannic acid 3:1 salt. The 1H-NMR and thermoanalysis results of the salt appearing FIGS. 55-57, respectively.

(p) Preparation of Sarcosine:Enriched Tannic Acid 1:1 Salt

A solution of sarcosine (181 mg, 2.04 mmol) in water (0.6 mL) was added to a RT solution of enriched tannic acid (3.0 g, 2.04 mmol) in absolute ethanol (12.0 mL). The mixture was slowly added to dichloromethane (250.0 mL) and stirred for 2 h at RT, during which a precipitate formed. The precipitate was collected and dried under vacuum at RT for 4 h to afford 2.8 g of sarcosine:enriched tannic acid 1:1 salt. The 1H-NMR and thermoanalysis results of the salt appear in FIGS. 58-60, respectively.

(q) Preparation of Sarcosine:Enriched Tannic Acid 1:2 Salt

A solution of sarcosine (91 mg, 1.02 mmol) in water (0.3 mL) was added to a RT solution of enriched tannic acid (3.0 g, 2.04 mmol) in absolute ethanol (12.0 mL). The mixture was slowly added to dichloromethane (250.0 mL) and stirred for 2 h at RT, during which a precipitate formed. The precipitate was collected and dried under vacuum at RT for 4 h to afford 2.8 g of sarcosine: enriched tannic acid 1:2 salt. The 1H-NMR and thermoanalysis results of the salt appear in FIGS. 61-63, respectively.

(r) Preparation of Clozapine:Tannic Acid 6:1 Salt

A solution of tannic acid (1.0 g, 0.89 mmol) (Merck Millipore, Germany) in absolute ethanol solution (4.0 mL) was added to a RT solution of clozapine (581 mg, 1.78 mmol) in acetonitrile (50.0 mL). The mixture was stirred at RT for 2 h, during which a precipitate formed. The precipitate was collected and dried under vacuum at RT for 4 h to afford 0.4 g of clozapine:tannic acid 6:1 salt. The 1H-NMR and thermoanalysis results of the salt appear in FIGS. 64-66, respectively.

(s) Preparation of Olanzapine:Enriched Tannic Acid 2:1 Salt

A solution of enriched tannic acid (10.0 g, 6.78 mmol) in acetonitrile (40.0 mL) was added to a solution of olanzapine (4.24 g, 13.58 mmol) in acetonitrile (260.0 mL). The resulting mixture was stirred at RT for 2 h, and a precipitate formed. The precipitate was collected and dried under vacuum at RT for 4 h to afford 10.5 g of olanzapine:enriched tannic acid 2:1 salt. The 1H-NMR and thermoanalysis results of the salt collected appear in FIGS. 99-101, respectively

Example 2. Stress Study of Clozapine, Benzoic Acid and Clozapine Benzoic Acid 1:1 Salt at 40° C./75% Relative Humidity in a Closed System 200 mg of clozapine, 200 mg of clozapine mixed with 250 mg of benzoic acid and 274.7 mg of clozapine benzoic acid 1:1 salt form mixed with 175.3 mg benzoic acid were independently put into a colorless glass bottle and kept at 40° C./75% relative humidity (RH) in a closed system (i.e. with the cap of the bottle closed) for the stress study. Before the stress study, clozapine, clozapine mixed with benzoic acid (a mechanical mixture) and clozapine benzoic acid 1:1 salt form mixed with benzoic acid (a mechanical mixture containing the 1:1 salt and benzoic acid) were analyzed by high performance liquid chromatography (HPLC), as shown in FIGS. 67 to 69. The retention times and areas are shown in Tables 2 to 4. After 30 days, the three samples were analyzed by HPLC, as shown in FIGS. 70 to 72. The retention times and areas are shown in Tables 5 to 7. The HPLC analysis of clozapine mixed with benzoic acid has two new peaks, which means the clozapine mixed with benzoic acid degraded during the stress study. In contrast, the HPLC analysis of clozapine benzoic acid 1:1 salt mixed with benzoic acid is identical between before and after stress study, which means the clozapine benzoic acid 1:1 salt did not degrade and it is more stable than the non-salt form of clozapine.

Group I: Clozapine 200 mg

Group II: Clozapine 200 mg+Benzoic Acid 250 mg

Group III: Clozapine Benzoic Acid Salt 1:1 (274.7 mg, including Clozapine 200 mg+Benzoic Acid 74.7 mg)+Benzoic Acid 175.3 mg

TABLE 2

Pre-stress test HPLC data for clozapine

| Compound | Retention Time | Area | Area % |
|---|---|---|---|
| Clozapine | 17.279 | 16010866 | 100 |

TABLE 3

Pre-stress test HPLC data for clozapine mixed with benzoic acid

| Compound | Retention Time | Area | Area % |
|---|---|---|---|
| Benzoic acid | 15.652 | 1644233 | 18.7307 |
| Clozapine | 17.463 | 7134063 | 81.2693 |

TABLE 4

Pre-stress test HPLC data for clozapine benzoic acid 1:1 salt form mixed with benzoic acid.

| Compound | Retention Time | Area | Area % |
|---|---|---|---|
| Benzoic acid | 15.612 | 1631571 | 17.0414 |
| Clozapine | 17.539 | 7942597 | 82.9586 |

TABLE 5

HPLC data for clozapine kept at 40° C./75% RH for 30 days

| Compound | Retention Time | Area | Area % |
|---|---|---|---|
| Clozapine | 17.279 | 16010866 | 100 |

TABLE 6

HPLC data for clozapine mixed with benzoic acid, after being stored at 40° C./75% RH for 30 days

| Compound | Retention Time | Area | Area % |
|---|---|---|---|
| Benzoic acid | 15.744 | 1423125 | 14.729 |
| Clozapine | 17.485 | 8042634 | 83.2393 |
| New Peak 1 | 18.367 | 45337 | 0.4692 |
| New Peak 2 | 19.218 | 150967 | 1.5625 |

TABLE 7

HPLC data for clozapine benzoic acid 1:1 salt mixed with benzoic acid, after being stored at 40° C./75% RH for 30 days

| Compound | Retention Time | Area | Area % |
|---|---|---|---|
| Benzoic acid | 15.602 | 1631201 | 17.0419 |
| Clozapine | 17.528 | 7940524 | 82.9581 |

Example 2 demonstrates the clozapine benzoic acid 1:1 salt is more stable than clozapine, in the presence of free benzoic acid.

Example 3. The Pharmacokinetic Study of Clozapine and Clozapine:Nicotinic Acid (1:1) Salt in Rats The objective of this study was to investigate the effect of clozapine and its salt on the pharmacokinetic profile.

Materials and Methods

Animal Housing and Drug Administration:

Male Sprague-Dawley rats were housed (1-2 rats per cage) with food and water available ad libitum in polysulfone ventilated cages (Alternative Design, AR, USA) in the animal room of SyneuRx. The colony was maintained on a 12/12-h light/dark cycle at the temperature of 22±2° C. All animals used in this study were adult rats (at least 2.5 months of age). All animal procedures were performed according to the protocols approved by Institutional Animal Care and Use Committee (IACUC).

Male Sprague-Dawley rats having a bodyweight between 250-300 g were randomly assigned to two groups. Group 1: clozapine at 60 mg/kg, Group 2: clozapine:nicotinic acid (1:1) salt at 83 mg/kg, which contains of the same amount of clozapine as in Group 1. The chemicals were suspended in sesame oil and administrated by single oral gavage at 2 ml/kg. All rats were fasted overnight with free access to water before oral administration of the testing compositions. On the day of dosing, the blood samples were collected at 0 min (prior to dosing), and 0.25, 0.5, 1, 2, 4, 6, 8, and 24 hr post-dosing.

Plasma Samples Preparation

Blood samples were collected from rat jugular veins and transferred into tubes coated with sodium heparin. To obtain plasma, the blood samples were centrifuged at 2,500×g for 15 min at 4° C. and the supernatants were collected and kept frozen in a freezer at −80° C., until they were analyzed.

Clozapine Quantification:

The plasma concentration of donepezil was determined by LC/MS. The chromatographic separation was carried out on a 5 μm EVO C8 100 Å LC column (100×4.6 mm, Kinetex®). The mobile phase was 0.1% formic acid in water and acetonitrile:methanol=8:2 set as gradient. Flow rate used was 0.3 mL/min. Column temperature was maintained at 40° C. and the injection volume was 30 μL.

The pharmacokinetic parameters were calculated using non-compartmental analysis (NCA) with WinNonlin to assess the systemic exposure of donepezil in rats.

Results

The plasma concentration-time curves of clozapine from the two groups were constructed and are shown in FIG. 73. The pharmacokinetic parameters including the peak plasma concentration ($C_{max}$), time to $C_{max}$ ($T_{max}$) of clozapine, the terminal half-life ($T_{1/2}$) and area under the blood concentration-time curve (AUC) were calculated and are shown in Table 8. The mean $C_{max}$ of clozapine following a single oral administration of clozapine (Group 1) and clozapine:nicotinic acid (1:1) salt (Group 2) were 191 ng/ml at 1.0 hours and 316 ng/kg at 0.8 hours, respectively. For the AUC (area under the plasma concentration-time curve) values, 1318 ng·hr/ml was calculated for Group 1 and 2132 ng·hr/ml was calculated for Group 2. The results show clozapine:nicotinic acid (1:1) salt significantly increased the plasma concentration of clozapine with 1.62 to 1.65-fold higher $C_{max}$ and AUC, when compared to free amine form of clozapine (Group 1).

TABLE 8

Parameters of Clozapine Pharmacokinetics

| Parameter | Clozapine(60 mg/kg) | Clozapine:nicotinic acid (1:1) salt (83 mg/kg) |
|---|---|---|
| $T_{max}$ (hr) | 1 ± 0.2 | 0.8 ± 0.6 |
| $T_{1/2}$ (hr) | 5.6 ± 1.7 | 3.2 ± 1.4 |
| $C_{max}$ (ng/mL) | 191 ± 91 | 316 ± 159 |
| AUC (ng · h/mL) | 1318 ± 520 | 2132 ± 1559 |
| AUC Increased (%) | 100 | 161.8 |

Example 4. The Therapeutic Effectiveness of Clozapine and Clozapine:Nicotinic Acid (1:1) Salt The objective of this experiment was to compare the therapeutic effectiveness of clozapine and clozapine:nicotinic acid (1:1) salt in alleviating psychotic symptoms of schizophrenia, using a mouse model having such symptoms induced by MK-801.

The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 2.5 months of age). All animal procedures were performed according to the protocols approved by Institutional Animal Care and Use Committee (IACUC).

The mice were randomly assigned into six groups listed below:

Group 1: vehicle control

Group 2: MK-801

Group 3: Clz (1 mg/kg)+MK-801

Group 4: Clz:NA 1:1 salt (1.38 mg/kg)+MK-801

Group 5: Clz (2 mg/kg)+MK-801

Group 6: Clz:NA 1:1 salt (2.75 mg/kg)+MK-801

Clz refers to clozapine and NA refers to nicotinic acid.

Mice in Groups 2-6 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-6 orally received an acute dose of clozapine or clozapine: nicotinic acid (1:1) salt (dissolved in $ddH_2O$ with 35% PEG400) 15 minutes prior to the MK-801 administration. The amount of clozapine administered to Groups 4 and 6 was equal to the amount of clozapine administered to Groups 3 and 5. All mice were tested with open field task.

The open field task is a common measurement of novelty induced exploratory behavior and general activity in both mice and rats. The objective of this experiment was to compare the efficacy of clozapine and its nicotinic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 74 shows the effect of clozapine and clozapine: nicotinic acid (1:1) salt on locomotion in MK-801 treated mice. Compared to the vehicle control group, the MK-801 treated group displayed hyper-locomotion in open field test. In comparison to the MK-801 group, the mice in treatment groups 3-6 exhibited significantly lower levels of locomotor activity. Moreover, with the same content of clozapine being administered, clozapine:nicotinic acid (1:1) salt (Groups 4 and 6) exhibited much lower levels of locomotor activity, when compared to clozapine groups (Groups 3 and 5). This result indicates clozapine:nicotinic acid (1:1) salt is more potent than clozapine in reversing MK-801-induced hyper-locomotion.

Example 5. Protective Effect of Clozapine:Nicotinic Acid (1:1) Salt on Metabolic Abnormalities The objective of this experiment was to evaluate the effect of clozapine and clozapine:nicotinic acid 1:1 salt induced metabolic symptoms such as hyperglycemia and glucose intolerance. The testing compounds were administered to mice either through intraperitoneal (i.p.) injection or oral gavage before analyzing blood glucose levels. C57BL/6J male mice were group housed under the same condition as described in Example 4.

Post-Drug Fasting Blood Glucose Level Analysis:

For the acute study, two cohorts of mice were used. In cohort one, mice were randomly assigned into three groups, Group 1: vehicle control, Group 2: Clz (10 mg/kg), and Group 3: Clz:NA 1:1 salt (13.77 mg/kg), which were intraperitoneal (i.p.) injected, respectively, with 35% PEG400 in $ddH_2O$, clozapine at 10 mg/kg, and clozapine:nicotinic acid 1:1 salt at 13.77 mg/kg. In cohort two, mice were randomly assigned into five groups, Group 1: vehicle control, Group 2: NA (3.77 mg/kg), Group 3: Clz (10 mg/kg), Group 4: Clz (10 mg/kg)+NA (3.77 mg/kg), and Group 5: Clz:NA 1:1 salt (13.77 mg/kg), which were orally administrated, respectively with 35% PEG400 in $ddH_2O$, nicotinic acid at 3.77 mg/kg, clozapine at 10 mg/kg, clozapine (10 mg/kg) and nicotinic acid (3.77 mg/kg) mixture, and clozapine:nicotinic acid 1:1 salt at 13.77 mg/kg.

For repeated-dose study, mice were randomly assigned into five groups as listed below.

Group 1: Vehicle control

Group 2: Clz (3 mg/kg)

Group 3: Clz:NA 1:1 salt (4.13 mg/kg)

Group 4: Clz (10 mg/kg)

Group 5: Clz:NA 1:1 salt (13.77 mg/kg)

Each mouse in Groups 2-5 was orally administered with clozapine (Clz) or clozapine:nicotinic acid 1:1 salt (Clz:NA 1:1 salt, dissolved in $ddH_2O$ with 35% PEG400) once daily for 3 days. The contents of clozapine in Groups 3 and 5 was the same as in Groups 2 and 4.

The night before blood glucose levels were measured, the mice were fasted. Blood glucose levels were measured with a portable glucose meter (Contour® Plus, Bayer AG, Leverkusen, Germany) After waiting for 60 min, the treatments indicated above were administered. FIG. 75 illustrates the experimental design of this study.

FIG. 76, panel (A) shows the effect of clozapine (Clz) and its nicotinic acid salt (Clz:NA 1:1 salt) on fasting blood glucose levels after acute i.p. injection. Compared to the vehicle control group, the glucose levels were higher in both clozapine and clozapine:nicotinic acid 1:1 salt groups (Group 2 and 3); however, administration of clozapine: nicotinic acid 1:1 salt exhibited a significant lower blood glucose level, when compared to clozapine. Similar result was observed in mice receiving treatments by oral gavage, as illustrated in FIG. 76, panel (B). When compared to the vehicle control group, both clozapine and a clozapine-nicotinic acid mixture significantly elevated fasting blood glucose, while nicotinic acid and clozapine:nicotinic acid 1:1 salt exhibited no to moderate effects. When compared to clozapine and clozapine-nicotinic acid mixture groups, clozapine:nicotinic acid 1:1 salt displayed a significantly lower blood glucose level. These results indicated that clozapine: nicotinic acid 1:1 salt is unexpectedly able to mitigate clozapine-induced hyperglycemia in mice.

FIG. 77 shows the effect of clozapine (Clz) and its nicotinic acid salt (Clz:NA 1:1 salt) on fasting blood glucose levels, after repeated oral administration for 3 days. Administration of clozapine at 3 mg/kg and 10 mg/kg displayed high fasting blood glucose levels, when compared to the vehicle control group. In contrast, a low dose of clozapine: nicotinic acid 1:1 salt (4.13 mg/kg) did not impact blood glucose levels. Although a high dose of clozapine:nicotinic acid 1:1 salt (13.77 mg/kg) also displayed higher blood glucose levels, when compared to the vehicle control group, the blood glucose level was comparable to the level of low dose clozapine (3 mg/kg) (133.5±9.0 v.s. 125.3±4.6 mg/dl). But a high dose of clozapine (10 mg/kg) exhibited a significantly higher level of blood glucose, when compared to the low dose of clozapine (3 mg/kg). This result indicates that oral administration of clozapine:nicotinic acid 1:1 salt is able to mitigate clozapine-induced hyperglycemia in mice.

Intraperitoneal Glucose Tolerance Test:

For the acute study, mice were randomly assigned into one of the five groups listed below.

Group 1: Vehicle control

Group 2: NA (3.77 mg/kg)

Group 3: Clz (10 mg/kg)

Group 4: Clz (10 mg/kg)+NA (3.77 mg/kg)

Group 5: Clz:NA 1:1 salt (13.77 mg/kg)

Each mice in Group 1-5 was orally administrated with 35% PEG400 in $ddH_2O$, nicotinic acid at 3.77 mg/kg, clozapine at 10 mg/kg, clozapine (10 mg/kg) and nicotinic acid (3.77 mg/kg) mixture, and clozapine:nicotinic acid 1:1 salt (13.77 mg/kg), respectively.

For the repeated dose study, two cohorts of mice were used. In cohort 1, mice were randomly assigned into one of the three groups listed below.

Group 1: Vehicle control

Group 2: Clz (10 mg/kg)

Group 3: Clz:NA 1:1 salt (13.77 mg/kg)

Each mouse in Groups 1-3 was orally administered with vehicle (35% PEG400 in $ddH_2O$), clozapine at 10 mg/kg and clozapine:nicotinic acid 1:1 salt at 13.77 mg/kg, respectively, once daily for 19 days. The same amount of clozapine was administered to the mice in Groups 2 and 3.

In cohort 2, the mice were randomly assigned into one of the three groups listed below.

Group 1: Vehicle control

Group 2: Clz (3 mg/kg)

Group 3: Clz:NA 1:1 salt (4.13 mg/kg)

Each mouse in Groups 1-3 was orally administered with vehicle (35% PEG400 in $ddH_2O$), clozapine at 3 mg/kg and clozapine:nicotinic acid 1:1 salt at 4.13 mg/kg, respectively, once daily for 36 days. The same amount of clozapine was administered to the mice in Groups 2 and 3.

To assess glucose tolerance, mice were fasted overnight on day 18 (for cohort 1) and on day 35 (for cohort 2), and their blood glucose response to i.p. administration of glucose (2 g/kg) was determined. Blood glucose levels were assessed in the whole blood collected from the tail vein, 60 min after drug administration Immediately following this glucose measurement, all mice were subjected to a glucose tolerance test by receiving an intraperitoneal challenge injection of 2 g/kg of glucose, and blood glucose levels were measured at 0, 30, 60 and 120 minutes. FIG. 78 illustrates the experimental design of this study.

FIG. 79 shows the effects of nicotinic acid (NA), clozapine (Clz) and clozapine:nicotinic acid 1:1 salt (Clz:NA 1:1 salt) on the blood glucose metabolism of mice after a single, orally administered does. When compared to the vehicle control, the metabolic profile of glucose was unchanged by nicotinic acid treatment. The blood glucose levels in mice treated with clozapine and clozapine-nicotinic acid mixture remained significantly higher than vehicle control group at virtually all time points during the IGTT (Impaired Glucose-Tolerance Test) study, while clozapine:nicotinic acid 1:1 salt exhibited a high glucose level only at 60 min, which returned to normal glucose levels at 120 min post glucose challenge. This result indicates clozapine:nicotinic acid 1:1 salt possesses the ability to restore glucose levels to the normal range, after a glucose challenge.

FIG. 80 shows the changes in blood glucose levels in mice that were orally administered with vehicle, clozapine (Clz, 10 mg/kg) and clozapine:nicotinic acid 1:1 salt (13.77 mg/kg) for 19 days. The results reveal that blood glucose levels were significantly higher for the clozapine (10 mg/kg) group, when compared to both vehicle control and clozapine:nicotinic acid 1:1 salt (13.77 mg/kg) groups at 60 and 120 min post glucose challenge. Mice that received clozapine: nicotinic acid 1:1 salt (13.77 mg/kg) displayed a similar profile of glucose metabolism to vehicle control group, which indicates the mice preserved the ability to restore glucose levels to the normal range, after a glucose challenge.

A similar result was observed in cohort 2 (FIG. 81). Blood glucose levels were significantly higher for the clozapine (3 mg/kg) group, when compared to both the vehicle control and clozapine:nicotinic acid 1:1 salt (4.13 mg/kg) groups. At 120 min post glucose challenge, the clozapine:nicotinic acid 1:1 salt (4.13 mg/kg) group displayed similar glucose levels to the vehicle control group, which indicates the mice preserved the ability to restore glucose levels to the normal range, after a glucose challenge.

Post-Drug Fasting Serum Insulin Level and Homeostatic Model Assessment-Insulin Resistance (Homa-Ir) Analysis:

Mice were randomly assigned to one of the three groups listed below.

Group 1: Vehicle control

Group 2: Clz (10 mg/kg)

Group 3: Clz:NA 1:1 salt (13.77 mg/kg)

Each mouse in Groups 1-3 was orally administered with vehicle (35% PEG400 in $ddH_2O$), clozapine at 10 mg/kg or clozapine:nicotinic acid 1:1 salt at 13.77 mg/kg, respectively, once daily for 8 days. The same amount of clozapine was administered to Groups 2 and 3.

For serum insulin level and HOMA-IR detection, the mice were fasted overnight one day before the study. The blood glucose levels were measured with a portable glucose meter (Contour® Plus, Bayer AG, Leverkusen, Germany) Approximately 100 μl of blood samples was collected from the facial vein of the mice 90 min after drug administration. Whole blood samples were incubated at room temperature for 30 min and subsequently centrifuged at 3500 rpm at 4° C. for 15 min to obtain sera. Serum insulin levels were determined using commercially available immunoassay kits (Mouse Insulin Eliza kit, ALPCO, NH, USA). The index of homeostatic model assessment-insulin resistance (HOMA-IR) was also used for assessing the function of insulin-glucose regulatory system, which was calculated based on the following equation: [fasting glucose (mmole/L)×fasting insulin (mIU/L)]/22.5.

FIG. 82, panel (A) shows the changes in fasting insulin levels in vehicle, clozapine (Clz) and its nicotinic acid salt (Clz:NA 1:1 salt) groups. After 8 days of repeated treatment, the fasting insulin level was elevated in clozapine group, when compared to both vehicle and clozapine:nicotinic acid 1:1 salt groups. The mean insulin level of the clozapine group is 10.52±3.56, which is a 1.57 fold and 1.96 fold increase, relative to the vehicle and clozapine:nicotinic acid 1:1 salt groups, respectively. A consistent result was also observed in the HOMA-IR index (FIG. 82 B). The clozapine-treated group displayed the highest HOMA-IR index among the three groups (2.97±0.62), while clozapine:nicotinic acid 1:1 salt exhibited a similar HOMA-IR index to the vehicle control group (1.61±0.54 v.s. 1.93±0.29). These results indicate reduced insulin sensitivity after 8-days of clozapine treatment, while the clozapine:nicotinic acid 1:1 salt is able to restore this effect.

Example 6. Characterization of Clozapine:Nicotinic Acid 1:1 Salt

The water solubility of the clozapine:nicotinic acid 1:1 salt at 25° C. was determined to be 1639.68 mg/mL, while the water solubility of the non-salt form of clozapine under the same temperature was determined to be 0.18 mg/mL.

USP 1174 was used to determine the Carr Index of the 1:1 salt and clozapine. The 1:1 salt had a Carr Index of 18%, while clozapine's was 25%. Thus, the 1:1 salt had better flowability.

The pharmacokinetics (PK) of the salt was greater than that of clozapine: the AUC was 1.6:1.

Conducting an MK801 model study on the salt and clozapine demonstrated the salt has a higher recovery rate than clozapine:

TABLE 9

Recovery Rates by Clozapine and NA Salt of Clozapine

| Dosage of clozapine (mg/kg) | Recovery rate (%) NA salt | Clozapine |
|---|---|---|
| 1 | 86 | 57 |
| 2 | 100 | 79 |

(a) Fast Glucose Assay

The effects of clozapine and NA salt of clozapine on hyperglycemia were investigated via acute i.p. of clozapine or NA salt of clozapine at 10 mg/kg (of clozapine) or by 3 day oral administration. The results show that clozapine induced hyperglycemia and the NA salt of clozapine (acute i.p. injection) reduced Clozapine-induced Hyperglycemia by 46.8% Similar results were observed in 3 day oral administration and acute oral administration. See Tables 10 and 11 below.

TABLE 10

Reduction of Hyperglycemia by 3-day Oral Administration

| Dosage of clozapine (mg/kg) | Rate of reduce clozapine-induced hyperglycemia (%) |
|---|---|
| 3 | 100 |
| 10 | 41.7 |

TABLE 11

Reduction of Hyperglycemia by Acute Oral Administration

| Dosage of clozapine (mg/kg) | Rate of reduce clozapine-induced hyperglycemia (%) Clozapine NA salt | Clozapine + NA |
|---|---|---|
| 10 | 56 | 0 |

The 1:1 salt reduced clozapine-induced hyperglycemia, when compared to a 1:1 physical mixture of clozapine and nicotinic acid.

(b) Glucose Tolerance Test

A glucose tolerance test after repeated doses of the 1:1 salt and clozapine showed the salt afforded lower blood glucose levels, when compared to vehicle after 120 minutes. The result is provided in Table 12.

TABLE 12

GTT test: Glucose metabolism (Test after Repeated dose of drug)

| Dosage of Clozapine (mg/kg) | Blood glucose level compared to vehicle after 120 min Days of repeated dose | NA Salt | Clozapine |
|---|---|---|---|
| 3 | 36 | 1.0 | 1.15 |
| 10 | 19 | 1.1 | 1.5 |

A glucose tolerance test after an acute, oral dosing of the 1:1 salt, the non-salt form of clozapine and a physical 1:1 mixture of clozapine and nicotinic acid showed the salt resulted in the lowest blood glucose levels. See Table 13.

TABLE 13

GTT test: (Acute oral Clozapine: 10 mg/kg)

| Dosage of clozapine (mg/kg) | Blood glucose level compared to vehicle after 120 min Clozapine NA salt | Clozapine | Clozapine + NA |
|---|---|---|---|
| 10 | 1.7 | 3.3 | 3.4 |

Administering the 1:1 salt and clozapine to fasting rats demonstrated the salt afforded lower serum insulin levels, when compared to vehicle, than clozapine did. A Homeostatic Model Assessment of Insulin Resistance test in rats also demonstrated the salt afforded lower insulin resistance, when compared to vehicle, than clozapine did. See Table 14.

TABLE 14

Fasting serum insulin (Clozapine: 10 mg/kg)

| Index | Salt | Clozapine |
|---|---|---|
| Serum insulin level compared to vehicle | 0.81 | 1.57 |
| HOMA-IR compared to vehicle | 0.83 | 1.54 |

Example 7. Characterization of Clozapine:Enriched Tannic Acid 2:1 Salt and 4:1 Salt The Carr Index of the 2:1 salt, 4:1 salt and clozapine was measured and the results are shown in Table 15 below.

TABLE 15

Carr Index

| Compound | Carr Index (%) |
|---|---|
| 2:1 salt | 33 |
| 4:1 salt | 19 |
| Clozapine | 25 |

This data demonstrates the 4:1 salt has greater flowability than clozapine, which has greater flowability than the 2:1 salt.

Acute oral dosing of the clozapine:enriched tannic acid salt, clozapine, and a physical mixture of clozapine and enriched tannic acid in rats demonstrates the salt's ability to lower the glucose AUC, when compared to vehicle, after 120 minutes. As shown in Table 16 below, administering the physical mixture of enriched tannic acid and clozapine resulting in AUCs that were higher than vehicle, after 120 minutes.

TABLE 16

| GTT test: (Acute oral Clozapine: 10 mg/kg) | | | |
|---|---|---|---|
| | Blood glucose curve AUC compared to vehicle after 120 min(ratio) | | |
| Dosage of clozapine (mg/kg) | Clozapine TA salt | Clozapine | Clozapine + TA |
| 10 | 0.96 | 2.48 | 1.49 |

The therapeutic effect (anti-hyperactivity) of the salt, clozapine and a physical mixture of clozapine and enriched tannic acid on mice was measured in an open field test, after an acute, 1 mg/kg dose. The data in Table 17 shows the salt had superior affect, when compared to clozapine and the physical mixture.

TABLE 17

| Open-field test: (Acute oral Clozapine: 1 mg/kg) | | | |
|---|---|---|---|
| | Anti−hyperactivity ratio after MK801−injection $\left(\left(1-\frac{(\text{Treatment}-\text{Vehicle})}{(\text{MK801}-\text{Vehicle})}\right)\times 100\%\right)$ | | |
| Dosage of clozapine (mg/kg) | Clozapine TA salt | Clozapine | Clozapine + TA |
| 1 | 46.16% | 18.77% | 21.98% |

Example 8. Protective Effect of Clozapine:Enriched Tannic Acid Salts on Metabolic Abnormalities The objective of this experiment was to evaluate the effects of clozapine (Clz) and clozapine:enriched tannic acid (TA) salts (2:1 and 4:1) on induced metabolic symptoms, such as hyperglycemia and glucose intolerance. The test compounds were administered to the mice by oral gavage, before analyzing the blood glucose levels. C57BL/6J male mice were group housed under the same condition as described in Example 4.

Mice used in this study were randomly assigned into one of the six following groups:

Group 1: Vehicle control
Group 2: Clz (10 mg/kg)
Group 3: Clz (10 mg/kg)+enriched TA (22.5 mg/kg)
Group 4: Clz (10 mg/kg)+enriched TA (11.3 mg/kg)
Group 5: Clz:enriched TA 2:1 salt (32.5 mg/kg)
Group 6: Clz:enriched TA 4:1 salt (21.3 mg/kg)

Each mouse in Groups 1-6 was orally administered, respectively, with a single dose of 35% PEG400 in $ddH_2O$, clozapine at 10 mg/kg, the mixture of clozapine (10 mg/kg) and enriched tannic acid (22.5 mg/kg), the mixture of clozapine (10 mg/kg) and enriched tannic acid (11.3 mg/kg), clozapine:enriched tannic acid 2:1 salt at 32.5 mg/kg, or clozapine:enriched tannic acid 4:1 salt at 13.94 mg/kg, 60 min prior to blood glucose detection. The same amount of clozapine was administered to the mice in Groups 2, 3, 4, 5 and 6, and the amount of enriched tannic acid administered to the mice in Groups 3 and 4 was equal to the amount administered to the mice in Groups 5 and 6.

One day before the glucose tolerance test, the mice fasted overnight and the blood glucose levels were measured in whole blood collected from the tail vein. Glucose levels were measured using a portable glucose meter (Contour® Plus, Bayer AG, Leverkusen, Germany) 60 min after they were acutely administered with the treatments indicated above Immediately following this glucose measurement, all mice were subjected to a glucose tolerance test by receiving an intraperitoneal challenge injection of 2 g/kg of glucose. Blood glucose levels were measured at 30, 60 and 120 minutes.

FIG. 83 shows the changes in blood glucose levels upon the administration of vehicle, clozapine, a mixture of clozapine and enriched tannic acid, and clozapine:enriched tannic acid salt. When compared to vehicle control, the blood glucose levels in the clozapine group were significantly higher 30, 60 and 120 mins after glucose challenge. When compared to the clozapine group (Group 2), the mixture of clozapine and enriched tannic (Group 3 and 4) moderately decreased blood glucose levels, while the clozapine:enriched tannic acid salts (2:1 and 4:1) significantly reversed the clozapine-induced impairment in glucose metabolism.

Example 9. Stability and Solubility of the Clozapine:Benzoic Acid 1:1 Salt

Clozapine:benzoic acid 1:1 salt and a physical mixture of clozapine and benzoic acid 1:1, made by mixing equimolar amounts of solid clozapine and solid benzoic acid were subjected to an accelerated stability test at 40° C. and 75% RH (relative humidity) for 30 days. The salt was stable (no impurity* occurs), while the physical mixture 2% impurities. Thus, the salt was more stable than the physical mixture.

The water solubility of the salt under 25° C. was determined to be 1.58 mg/mL, while the water solubility of clozapine under the same temperature was determined to be 0.18 mg/mL. This demonstrates the 1:1 salt is more soluble than the non-salt form of clozapine.

Example 10. The Therapeutic Effectiveness of Clozapine and Clozapine:Benzoic Acid (1:1) Salt The objective of this experiment was to compare the therapeutic effectiveness of clozapine and clozapine:benzoic acid (1:1) salt in alleviating psychotic symptoms of schizophrenia, using a mouse model having such symptoms induced by MK-801. The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age). All animal procedures were performed according to the protocols approved by Institutional Animal Care and Use Committee (IACUC).

The mice were randomly assigned into four groups listed below:

Group 1: vehicle control n=7
Group 2: MK-801 n=7
Group 3: Clozapine (1 mg/kg)+MK-801 n=8
Group 4: Clz:BA salt (1.37 mg/kg)+MK-801 n=8

Clz refers to Olanzapine and Clz:BA refers to Clozapine: benzoic acid (1:1) salt.

Mice in Groups 2-4 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-4 orally received an acute dose of clozapine or clozapine: benzoic acid (1:1) salt (dissolved in $ddH_2O$ with 35% PEG400) 15 minutes prior to the MK-801 administration. The amount of clozapine administered to Groups 3 and 4 was equal. The schizophrenia-like behavior, MK801-induced hyperactivity, were tested by open field task.

The open field task is a common measurement of novelty induced exploratory behavior and general activity in both mice and rats. The objective of this experiment was to compare the efficacy of clozapine and its benzoic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 84 displays the effect of clozapine and clozapine: benzoic acid (1:1) salt on locomotion in MK-801 treated mice. The MK801 insult (0.2 mg/kg) induces hyper-locomotion in the open-field test. Both clozapine and clozapine: benzoic acid (1:1) salt (group 3 and 4) could alleviates MK-801 induced hyperactivity. However, the clozapine: benzoic acid (1:1) salt shows higher potency to MK-801-induced hyperactivity in which clozapine:benzoic acid (1:1) salt treated mice (group 3) exhibited decreased locomotion activity, compared with the clozapine group. This result indicates that clozapine:benzoic acid (1:1) salt is more potent than clozapine and has great potential as an novel antipsychotic medication.

TABLE 18

Recovery Rates by Clozapine:Benzoic Acid Salt in MK801-Treated Mice

| Dosage of Clozapine | Recovery rate (%) | |
|---|---|---|
| (mg/kg) | BA salt | Clozapine |
| 1 | 85.8 | 65.1 |

Example 11. The Therapeutic Effectiveness of Olanzapine and Olanzapine:Nicotinic Acid (1:1) Salt The objective of this experiment was to compare the therapeutic effectiveness of olanzapine (Olz) and olanzapine:nicotinic acid (Olz:NA) (1:1) salt, in alleviating psychotic symptoms of schizophrenia, using a mouse model having such symptoms induced by MK-801.

The test compounds were administered to the mice by oral gavage, while the MK-801 was administrated by intraperitoneal (i.p.) injections, before the open field test.

C57BL/6J male mice were group housed under the same condition as described in Example 4. The mice were randomly assigned into 4 groups listed below.

Group 1: Vehicle control
Group 2: MK-801
Group 3: Olz (0.1 mg/kg)+MK-801
Group 4: Olz:NA 1:1 salt (0.14 mg/kg)+MK-801

Mice in Groups 2-4 received an acute administration of MK-801 (Sigma-Aldrich USA), a NMDA receptor antagonist, dissolved in normal saline, at 0.2 mg/kg by i.p. injection, 30 minutes prior to the start of the open field test. Each mouse in Groups 3 and 4 orally received an acute administration of olanzapine at 0.1 mg/kg (Group 3) or olanzapine: nicotinic acid (1:1) salt at 0.14 mg/kg (dissolved in $ddH_2O$ with 65% PEG400) (Group 4), 15 minutes prior to the MK-801 administration. The amount of olanzapine administered to Groups 3 and 4 was the same. All mice were tested in an open field task.

The open field task was used to compare the effectiveness of olanzapine and its nicotinic acid salt on attenuating MK-801-induced hyper-locomotion. The apparatus and recording method of open field were as described above in Example 3.

FIG. 85 shows the effect of olanzapine (Olz) and olanzapine:nicotinic acid 1:1 salt (Olz:NA 1:1 salt) on locomotion in MK-801 treated mice. When compared to the vehicle control group, the MK-801 treated group displayed hyper-locomotion in the open field test. When compared to the MK-801 group the olanzapine dosed group (Group 3) exhibited attenuated hyper-locomotion, while the olanzapine: nicotinic acid 1:1 salt dosed group (Group 4) exhibited a significant decrease in MK-801-induced hyper-locomotion. These results demonstrate olanzapine:nicotinic acid 1:1 salt is more potent than olanzapine in reversing MK-801-induced hyper-locomotion.

Example 12. Protective Effect of Olanzapine:Nicotinic Acid 1:1 Salt on Metabolic Abnormalities The objective of this experiment was to compare the impact of olanzapine and olanzapine:nicotinic acid 1:1 salt on induced metabolic symptoms, such as hyperglycemia and glucose intolerance. The testing compounds were administered to mice through intraperitoneal (i.p.) injection, before analyzing blood glucose levels. C57BL/6J male mice were group housed under the same condition as described in Example 4.

Intraperitoneal Glucose Tolerance Test:

Two cohorts of mice were used in this study. In cohort 1, mice were randomly assigned into the five groups listed below:

Group 1: Vehicle control
Group 2: NA (3.94 mg/kg)
Group 3: Olz (10 mg/kg)
Group 4: Olz (10 mg/kg)+NA (3.94 mg/kg)
Group 5: Olz:NA 1:1 salt (13.94 mg/kg)

Each mouse in Groups 1-5 was orally administered with a single dose of 35% PEG400 in $ddH_2O$, nicotinic acid at 3.94 mg/kg, olanzapine at 10 mg/kg, olanzapine (10 mg/kg) and nicotinic acid (3.94 mg/kg) mixture, and olanzapine: nicotinic acid 1:1 salt at 13.94 mg/kg, respectively. Dosing occurred 60 min prior to measuring blood glucose levels.

In cohort 2, mice were randomly assigned into the five groups listed below:

Group 1: Vehicle control
Group 2: Olz (5 mg/kg)
Group 3: Olz:NA 1:1 salt (6.97 mg/kg)
Group 4: Olz (10 mg/kg)
Group 5: Olz:NA 1:1 salt (13.94 mg/kg)

Each mouse at Group 2-5 was i.p. injected with a single dose of olanzapine or olanzapine:nicotinic acid 1:1 salt (dissolved in $ddH_2O$ with 35% PEG400), 60 min prior to measuring blood glucose levels. The amount of olanzapine in Group 3 and 5 were equal to Group 2 and 4, respectively.

The night before the glucose tolerance test, the mice fasted. Blood glucose levels were measured in whole blood that was collected from the mouse's tail vein. Glucose levels were measured with a portable glucose meter (Contour® Plus, Bayer AG, Leverkusen, Germany), with the measurement occurring 60 min after the mice were dosed with the treatments indicated above Immediately following the glucose measurement, all mice were subjected to a glucose tolerance test, which involved an intraperitoneal challenge injection of 1 g/kg of glucose, followed by measuring blood glucose levels at 0, 30, 60 and 120 minutes.

FIG. 86, panel (A) shows the effects of olanzapine (Olz) and its nicotinic acid salt (Olz:NA 1:1 salt) in fasting blood glucose levels after acute i.p. injection. Compared to vehicle control group, both olanzapine groups (Groups 2 and 4) exhibited significantly elevated fasting blood glucose; however, administration of olanzapine:nicotinic acid 1:1 salt (Groups 3 and 5) exhibited blood glucose levels comparable to those of the vehicle control group. A similar result was observed in mice orally administered with different treatments, as illustrated in FIG. 85, panel (B). Compared to vehicle control group, both olanzapine and a mixture of olanzapine and nicotinic acid significantly elevated fasting blood glucose, while nicotinic acid and olanzapine:nicotinic acid 1:1 salt exhibited no to moderate impacton elevated fasting blood glucose levels. These results indicate olanzapine:nicotinic acid 1:1 salt is able to mitigate olanzapine-induced hyperglycemia in mice, when administered by i.p. injection or by oral delivery.

FIG. 87 shows the changes in blood glucose levels, when vehicle, olanzapine (Olz, 5 mg/kg) and olanzapine:nicotinic acid 1:1 salt (Olz:NA 1:1 salt, 6.97 mg/kg) are administered. The results revealed blood glucose levels in the olanzapine (5 mg/kg) group remained significantly higher than the vehicle control group at virtually all time points during the IGTT study. Conversely, glucose levels in the olanzapine:nicotinic acid 1:1 salt (6.97 mg/kg) group were significantly higher than vehicle control group at 120 min after glucose challenge. A similar result was observed when higher doses of olanzapine (10 mg/kg) and olanzapine:nicotinic acid 1:1 salt (13.94 mg/kg) were administered, as shown in FIG. 88. When compared to the vehicle control group, olanzapine (10 mg/kg) induced significantly higher blood glucose levels at 60 and 120 min after glucose challenge. Blood glucose levels from the olanzapine:nicotinic acid 1:1 salt (13.94 mg/kg) groups were significantly higher than vehicle control group at 120 min after glucose challenge and remained lower than the olanzapine (10 mg/kg) group at all time points during IGTT study. These results indicate olanzapine:nicotinic acid 1:1 salt preserved the ability of the mice to attenuate their glucose levels to the normal range, after a glucose challenge.

FIG. 89 shows the effects of nicotinic acid (NA), olanzapine (Olz) and olanzapine:nicotinic acid 1:1 salt (Olz:NA 1:1 salt) on blood glucose metabolism in mice, after oral administration. The blood glucose metabolism levels in the vehicle and nicotinic acid groups were virtually identical. The blood glucose levels in mice treated with olanzapine and olanzapine-nicotinic acid mixture were significantly higher than the vehicle control group at virtually all time points during IGTT study. In contrast, the olanzapine:nicotinic acid 1:1 salt group exhibited high glucose levels only after 60 mins, before returning to normal glucose levels 120 min post glucose challenge. These results indicate that olanzapine:nicotinic acid 1:1 salt possessed the ability to restore glucose levels to the normal range, after a glucose challenge.

Example 13. Characterization of Olanzapine:Nicotinic Acid Salt 1:1

The solubility of the olanzapine:nicotinic acid salt 1:1 salt in water, was determined to be 2.3 mg/mL under 25° C., while the non-salt form of olanzapine had a water solubility of <0.033 mg/mL under the same temperature.

Conducting an MK801 model study on the salt and olanzapine demonstrated the salt has a higher recovery rate than clozapine as shown in Table 19 below.

TABLE 19

Recovery Rates by Olanzapine:Nicotine Acid Salt in MK801-Treated Mice

| Dosage of olanzapine | Recovery rate (%) | |
|---|---|---|
| (mg/kg) | NA salt | Olanzapine |
| 0.1 | 47.9 | 36.8 |

Acute, intra peritoneal administration of olanzapine induced hyperglycemia as observed in a mouse model. As shown in Table 20 below, the NA salt of olanzapine (1:1) reduced olanzapine-induced hyperglycemia.

TABLE 20

Fasting Glucose (Acute i.p.)

| Dosage of olanzapine (mg/kg) | Rate of reduce olanzapine-induced hyperglycemia (%) |
|---|---|
| 5 | 57.6 |
| 10 | 38.4 |

Acute, oral administration of 1:1 nicotinic acid salt reduced olanzapine induced hyperglycemia, when compared to a 1:1 physical mixture of olanzapine and nicotinic acid. See Table 21 below.

TABLE 21

Fasting Glucose (Acute oral)

| Dosage of Olanzapine | Rate of reduce olanzapine-induced hyperglycemia (%) | |
|---|---|---|
| (mg/kg) | Olanzapine NA salt | Olanzapine + NA |
| 10 | 50.5 | 0 |

A glucose tolerance test after an acute, oral dosing of the 1:1 salt, olanzapine and a 1:1 physical mixture of olanzapine and nicotinic acid (NA) showed the salt afforded lowest blood glucose levels, when compared to vehicle after 120 minutes. See Table 22 below.

TABLE 22

| GTT test: (Acute oral Olanzapine) | | | |
|---|---|---|---|
| | Blood glucose level compared to vehicle after 120 min | | |
| Dosage of Olanzapine (mg/kg) | Olanzapine NA salt | Olanzapine | Olanzapine + NA |
| 10 | 1.5 | 2.37 | 2.81 |

A glucose tolerance test after administering 10 mg/kg and 5 mg/kg of the 1:1 salt and olanzapine showed the salt afforded lower blood glucose levels than olanzapine, when compared to vehicle after 120 minutes. See Table 23 below.

TABLE 23

| GTT test: Glucose metabolism | | |
|---|---|---|
| Dosage of Olanzapine | Blood glucose level compared to vehicle after 120 min | |
| (mg/kg) | NA Salt | Olanzapine |
| 10 | 2.75 | 3.21 |
| 5 | 2.21 | 3.64 |

Example 14. Characterization of Olanzapine:Enriched Tannic Acid 2:1 Salt

The therapeutic effect (anti-hyperactivity) of the salt, olanzapine and a physical mixture of olanzapine and enriched tannic acid on mice was measured in an open field test, after an acute, 1 mg/kg dose. The data (in Table 24) shows the salt had superior affect, when compared to clozapine and the physical mixture.

TABLE 24

| Open-field test: (Acute oral Olanzapine: 0.5 mg/kg) | | | |
|---|---|---|---|
| | Anti-hyperactivity effect (%) after MK801-injection $\left(\left(1-\frac{(\text{Treatment}-\text{Vehicle})}{(\text{MK801}-\text{Vehicle})}\right)\times 100\%\right)$ | | |
| Dosage of Olanzapine (mg/kg) | Olanzapine TA salt | Olanzapine | Olanzapine + TA |
| 0.5 | 112.82% | 30.53% | 83.20% |

Example 15. Characterization Olanzapine:Pantothenic Acid 5:1 Salt

The solubility of the olanzapine:pantothenic acid salt in water at 25° C. was determined to be 128 mg/mL. The water solubility of olanzapine under the same temperature was <0.033 mg/mL.

Example 16. The Therapeutic Effectiveness of Olanzapine and Olanzapine: Pantoic Acid (5:1) Salt The objective of this experiment was to compare the therapeutic effectiveness of Olanzapine and olanzapine: pantoic acid (5:1) salt in alleviating psychotic symptoms of schizophrenia, using a mouse model having such symptoms induced by MK-801. The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age). All animal procedures were performed according to the protocols approved by Institutional Animal Care and Use Committee (IACUC).

The mice were randomly assigned into four groups listed below:

Group 1: vehicle control
Group 2: MK-801
Group 3: Olz (0.5 mg/kg)+MK-801
Group 4: Olz:PA salt (0.547 mg/kg)+MK-801
Olz refers to Olanzapine and Olz:PA refers to Olanzapine: pantoic acid (5:1) salt.

Mice in Groups 2-6 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-4 orally received an acute dose of Olanzapine or Olanzapine: pantoic acid (5:1) salt (dissolved in $ddH_2O$ with 35% PEG400) 15 minutes prior to the MK-801 administration. The amount of Olanzapine administered to Groups 3 and 4 was equal. The schizophrenia-like behavior, MK801-induced hyperactivity, were tested by open field task.

The open field task is a common measurement of novelty induced exploratory behavior and general activity in both mice and rats. The objective of this experiment was to compare the efficacy of Olanzapine and its pantoic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 90 displays the effect of Olanzapine and Olanzapine: pantoic acid (5:1) salt on locomotion in MK-801 treated mice. The MK801 insult (0.2 mg/kg) induced hyper-locomotion in the open-field test. Both Olanzapine and Olanzapine:pantoic acid (5:1) salt (group 3 and 4) could alleviates MK-801 induced hyperactivity. However, the Olanzapine:pantoic acid (5:1) salt shows higher potency to MK-801-induced hyperactivity in which Olanzapine:pantoic acid (5:1) salt treated mice (group 3) exhibited decreased locomotion activity, compared with Olanzapine group. This result indicates that Olanzapine:pantoic acid (5:1) salt is more potent than Olanzapine (See Table 25) and has great potential as an novel antipsychotic medication.

TABLE 25

| Open-field test: (Acute oral Olanzapine: 0.5 mg/kg) | | |
|---|---|---|
| | Anti−hyperactivity ratio after MK801−injection $\left(\left(1-\frac{(\text{Treatment}-\text{Vehicle})}{(\text{MK801}-\text{Vehicle})}\right)\times 100\%\right)$ | |
| Dosage of Olanzapine (mg/kg) | Olanzapine PA salt | Olanzapine |
| 0.5 | 101.0% | 85.8% |

Example 17. Analgesic Effects of Gabapentin:Enriched Tannic Acid Salts in Mice

The objective of this experiment was to assess the analgesic effects of gabapentin:enriched tannic acid salts in mice. The testing compounds were administrated to mice by oral gavage before von Frey test (a typical assay for pain sensation). C57BL/6J male mice were group housed under the same condition as described in Example 4.

Mice used in this study were randomly assigned into six groups:

Group 1: Vehicle control
Group 2: Enriched TA (200 mg/kg)
Group 3: GBP (20 mg/kg)
Group 4: GBP:enriched TA 1:1 salt (192 mg/kg)
Group 5: GBP:enriched TA 2:1 salt (106.02 mg/kg)
Group 6: GBP:enriched TA 3:1 salt (77.34 mg/kg)

Each mouse in Groups 1-6 received a single, oral dose of 65% PEG400 in $ddH_2O$, enriched tannic acid at 200 mg/kg, gabapentin at 20 mg/kg, gabapentin:enriched tannic acid 1:1 salt (192 mg/kg), gabapentin:enriched tannic acid 2:1 salt (106.02 mg/kg) and gabapentin:enriched tannic acid 3:1 salt (77.34 mg/kg). The amount of gabapentin administered to the mice in Groups 3 to 6 was the same.

Mice were habituated in individual transparent acrylic box on a wire-mesh floor for 30 min before testing. An electronic von Frey apparatus (Bioseb-EVF4S) was used to measure the paw withdrawal thresholds (g) of each mouse before drug administration (baseline) and at 15, 30, 60, 120 and 180 mins after drug administration.

FIG. 91 shows the analgesic effects of enriched tannic acid (TA), gabapentin (GBP), gabapentin:enriched tannic acid 1:1 salt (GBP:TA 1:1 salt), gabapentin:enriched tannic acid 2:1 salt (GBP:TA 2:1 salt) and gabapentin:enriched tannic acid 3:1 salt (GBP:TA 3:1 salt) in mice. At baseline, no difference was found between the groups. Upon comparing the results, the following can be seen. When compared to vehicle control group, the threshold of GBP:TA 1:1 salt group (Group 4) was significantly higher at 60 and 120 min, GBP:TA 2:1 salt group (Group 5) was significantly higher at 30 min, and GBP:TA 3:1 salt group (Group 6) was significantly higher at 30, 60 and 120 min after administration. Enriched tannic acid at 200 mg/kg (Group 2) and gabapentin at 20 mg/kg (Group 3) showed no difference from control group at any time point examined.

FIG. 92 shows the area under the curve (AUC) values of von Frey pain threshold. The AUC values for analgesia effects were significantly higher in GBP:TA 1:1 and 3:1 salt groups, when compared to vehicle control group. Enriched tannic acid or gabapentin alone induced little to no effect. The AUC values of the GBP:TA 1:1 and 3:1 salts groups were about twice as high as in gabapentin group, and about 3- to 4-fold as high as in enriched tannic acid group. These results demonstrate a synergistic effect results when a GBP:TA (enriched) salt is used.

Example 18. Characterization of Gabapentin:Enriched Tannic Acid 3:1 Salt

Therapeutic effect (mechanical analgesic effect) of the salt was compared to the non-salt form of gabapentin in a mouse model. The pain threshold to time AUC after 120 minutes was higher for the salt than for the non-salt. See Table 26 below.

TABLE 26

| Von frey test: (Acute oral: 20 mg/kg) | | |
|---|---|---|
| Dosage of | Pain threshold to time AUC after 120 min | |
| (mg/kg) | TA salt | Gabapentin |
| 20 | 2.80 | 1.28 |

The data in the above examples demonstrates the surprising and unexpected results obtained when the claimed salts are used.

Example 19. Characterization of Quetiapine:Nicotinic Acid 1:1 Salt

The solubility of the Quetiapine:Nicotinic Acid 1:1 salt in water was determined to be 262 mg/mL under 25° C., while the water solubility of the commercially available, quetiapine:fumaric acid 1:1 salt was determined to be 0.62 mg/mL under the same temperature. Thus, the nicotinic acid salt is significantly more soluble than the commercially available fumaric acid salt.

The Carr Index of the quetiapine:nicotinic acid 1:1 salt was 20%, which is lower than the 33% value obtained when the commercially available, quetiapine:fumaric acid 1:1 salt was tested.

Example 20: The Therapeutic Effectiveness of Quetiapine and Quetiapine:Nicotinic Acid (1:1) Salt The objective of this experiment was to compare the therapeutic effectiveness of quetiapine and quetiapine:nicotinic acid (1:1) salt in alleviating psychotic symptoms of schizophrenia, using a mouse model having such symptoms induced by MK-801. The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age). All animal procedures were performed according to the protocols approved by Institutional Animal Care and Use Committee (IACUC).

The mice were randomly assigned into four groups listed below:

Group 1: Vehicle control

Group 2: MK-801

Group 3: Que (10 mg/kg)+MK-801

Group 4: Que:NA salt (12.8 mg/kg)+MK-801

Que refers to quetiapine and Que:NA refers to quetiapine: nicotinic acid (1:1) salt.

Mice in Groups 2-4 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-4 orally received an acute dose of quetiapine or quetiapine: nicotinic acid (1:1) salt (dissolved in $ddH_2O$ with 35% PEG400) 15 minutes prior to the MK-801 administration. The amount of quetiapine administered to Groups 3 and 4 was equal. The schizophrenia-like behavior, NMDA-hypofunction-induced hyperactivity, were tested by open field task.

The open field task is a common measurement of novelty induced exploratory behavior and general activity in both mice and rats. The objective of this experiment was to compare the efficacy of quetiapine and its nicotinic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 93 displays the effect of quetiapine and quetiapine: nicotinic acid (1:1) salt on locomotion in MK-801 treated mice. The MK801 insult (0.2 mg/kg) induced hyper-locomotion in the open-field test. Both quetiapine and quetiapine:nicotinic acid (1:1) salt (group 3 and 4) could alleviates MK-801 induced hyperactivity. However, the quetiapine: nicotinic acid (1:1) salt shows higher potency to MK-801-induced hyperactivity in which quetiapine:nicotinic acid (1:1) salt treated mice (group 3) exhibited significant decrease in locomotion activity, compared with quetiapine group. This result indicates that quetiapine:nicotinic acid (1:1) salt is more potent than quetiapine and has a great potential as a novel antipsychotic medication.

TABLE 27

| Open-field test: (Acute oral Quetiapine: 10 mg/kg) | | |
|---|---|---|
| | Anti-hyperactivity ratio after MK801-injection $\left(\left(1-\frac{(\text{Treatment}-\text{Vehicle})}{(\text{MK801}-\text{Vehicle})}\right)\times 100\%\right)$ | |
| Dosage of Quetiapine (mg/kg) | Quetiapine NA salt | Quetiapine |
| 10 | 53.1% | 8.7% |

Example 21: Protective Effect of Quetiapine:Nicotinic Acid (1:1) Salt on Metabolic Abnormalities The objective of this experiment was to evaluate the effects of quetiapine and quetiapine:nicotinic acid salts on quetiapine-induced metabolic symptoms, including hyperglycemia and glucose intolerance. The test compounds were administered to the mice by oral gavage, before analyzing the blood glucose levels. C57BL/6J male mice were group housed under the same condition as described in Example 4.

Mice used in this study were randomly assigned into one of the three following groups:

Group 1: Vehicle control n=6

Group 2: Quetiapine (20 mg/kg) n=3

Group 3: Quetiapine:nicotinic acid 1:1 salt (25.64 mg/kg) n=3

Each mouse in Groups 1-3 was orally administered, respectively, with a single dose of control vehicle (35% PEG with $ddH_2O$), quetiapine at 20 mg/kg, or quetiapine:nicotinic acid 1:1 salt at 25.64 mg/kg, 30 min prior to glucose tolerance test (GTT). The amount of quetiapine administered to Groups 2 and 3 was equal. One day before the glucose tolerance test, the mice were received overnight-fasting. The blood glucose levels of treated mice were measured form blood samples collected of the tail vein by portable glucose meter (Contour® Plus, Bayer AG, Leverkusen, Germany) Thirty minutes after test compound treatment, all mice were subjected to a GTT by receiving an intraperitoneal challenge injection of 2 g/kg of glucose. Blood glucose levels were measured at 30, 60 and 120 minutes. The area under curve (AUC) was derived from the blood glucose-time curve of GTT for comparing the quetiapine-induced hyperglycemia between quetiapine and quetiapine:nicotinic acid 1:1 salt groups.

FIG. 94 shows the changes in blood glucose levels upon the administration of vehicle, quetiapine, and quetiapine: nicotinic acid (1:1) salt during GTT test. The blood glucose levels of quetiapine-treated mice are elevated on the most measured time points, including 30, 60, and 120 min after glucose challenge, compared with vehicle and quetiapine: nicotinic acid (1:1) salt groups. The AUC of quetiapine group is notably higher than quetiapine:nicotinic acid (1:1) salt and vehicle groups and this finding indicates significant hyperglycemia in quetiapine-treated mice, which is not observed in quetiapine:nicotinic acid (1:1) salt and vehicle groups. These results suggest that quetiapine:nicotinic acid salt could reverse the quetiapine-induced metabolic effect with similar blood glucose response as the vehicle control group. To sum up, quetiapine:nicotinic acid (1:1) salt shows significant protective effect of quetiapine-induced hyperglycemia and is a promising candidate of novel psychotic medications with very low metabolic adverse effect.

TABLE 28

| GTT test: Glucose metabolism | | |
|---|---|---|
| Dosage of Quetiapine | Blood glucose level compared to vehicle after 120 min | |
| (mg/kg) | NA Salt | Quetiapine |
| 20 | 1.00 | 1.48 |

Example 22. Characterization of Risperidone:Nicotinic Acid 1:1 Salt

The solubility of the salt in water was determined to be 2170.77 mg/mL at 25° C., while the solubility of the non-salt form of risperidone was determined to be <0.005 mg/mL under the same temperature.

Example 23. The Therapeutic Effectiveness of Risperidone and Risperidone:Nicotinic Acid (1:1) Salt The objective of this experiment was to compare the therapeutic effectiveness of risperidone and risperidone: nicotinic acid (1:1) salt in alleviating psychotic symptoms of schizophrenia, using a mouse model having such symptoms induced by MK-801. The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age). All animal procedures were performed according to the protocols approved by Institutional Animal Care and Use Committee (IACUC).

The mice were randomly assigned into four groups listed below:

Group 1: vehicle control

Group 2: MK-801

Group 3: Ris (0.06 mg/kg)+MK-801

Group 4: Ris:NA salt (0.078 mg/kg)+MK-801

Ris refers to Risperidone and Ris:NA refers to Risperidone:nicotinic acid (1:1) salt.

Mice in Groups 2-6 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-4 orally received an acute dose of risperidone or risperidone: nicotinic acid (1:1) salt (dissolved in $ddH_2O$ with 35% PEG400) 15 minutes prior to the MK-801 administration. The amount of risperidone administered to Groups 3 and 4 was equal. The schizophrenia-like behavior, MK801-induced hyperactivity, were tested by open field task.

The open field task is a common measurement of novelty induced exploratory behavior and general activity in both mice and rats. The objective of this experiment was to compare the efficacy of risperidone and its nicotinic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 95 displays the effect of risperidone and risperidone: nicotinic acid (1:1) salt on locomotion in MK-801 treated mice. The MK801 insult (0.2 mg/kg) induced hyper-locomotion in the open-field test. Both risperidone and risperidone:nicotinic acid (1:1) salt (group 3 and 4) could alleviates MK-801 induced hyperactivity. However, the risperidone: nicotinic acid (1:1) salt shows higher potency to MK-801-induced hyperactivity in which risperidone:nicotinic acid (1:1) salt treated mice (group 3) exhibited decreased locomotion activity, compared with risperidone group. This result indicates that risperidone:nicotinic acid (1:1) salt is more potent than risperidone and has great potential as an novel antipsychotic medication.

TABLE 29

Open-field test: (Acute oral Risperidone: 10 mg/kg)

| Dosage of Risperidone (mg/kg) | Anti-hyperactivity ratio after MK801-injection $\left(\left(1-\frac{(\text{Treatment}-\text{Vehicle})}{(\text{MK801}-\text{Vehicle})}\right)\times 100\%\right)$ Risperidone NA salt | Risperidone |
|---|---|---|
| 10 | 80.1% | 48.7% |

Example 24. Protective Effect of Risperidone:Nicotinic Acid (1:1) Salt on Metabolic Abnormalities The objective of this experiment was to evaluate the effects of risperidone and risperidone:nicotinic acid salts on induced metabolic symptoms, including hyperglycemia and glucose intolerance. The test compounds were administered to the mice by oral gavage, before analyzing the blood glucose levels. C57BL/6J male mice were group housed under the same condition as described in Example 4.

Mice used in this study were randomly assigned into one of the three following groups:

Group 1: Vehicle control n=6

Group 2: Risperidone (12 mg/kg) n=7

Group 3: Risperidone:nicotinic acid 1:1 salt (15.6 mg/kg) n=8

Each mouse in Groups 1-3 was orally administered, respectively, with a single dose of control vehicle (35% PEG with $ddH_2O$), risperidone at 12 mg/kg, or risperidone: nicotinic acid 1:1 salt at 15.6 mg/kg, 30 min prior to glucose tolerance test (GTT). The amount of risperidone administered to Groups 2 and 3 was equal. One day before the glucose tolerance test, the mice were received overnight-fasting. The blood glucose levels of treated mice were measured by blood samples collected from the tail vein by portable glucose meter (Contour® Plus, Bayer AG, Leverkusen, Germany) Thirty minutes after test compound treatment, all mice were subjected to a GTT by receiving an intraperitoneal challenge injection of 2 g/kg of glucose. Blood glucose levels were measured at 30, 60 and 120 minutes. The area under curve (AUC) was derived from the blood glucose-time curve of GTT for comparing the risperidone-induced hyperglycemia between risperidone and risperidone:nicotinic acid 1:1 salt groups.

FIG. 96 shows the changes in blood glucose levels upon the administration of vehicle, risperidone, and risperidone: nicotinic acid (1:1) salt over time. The blood glucose level of risperidone-treated mice is significantly elevated on 120 min after glucose challenge, unlike vehicle and risperidone: nicotinic acid (1:1) salt groups, which is all below 200 mg/dl. The AUC of risperidone group is notably higher than risperidone:nicotinic acid (1:1) salt and vehicle groups and this finding indicates significant hyperglycemia in risperidone-treated mice, which is not observed in vehicle and risperidone:nicotinic acid (1:1) salt groups. These results indicate that risperidone:nicotinic acid salt could reverse the risperidone-induced metabolic effect with similar blood glucose response as the vehicle control group. To sum up, risperidone:nicotinic acid (1:1) salt shows significant protective effect of risperidone-induced hyperglycemia and is a promising candidate of novel psychotic medications with very low metabolic adverse effect.

TABLE 30

| GTT test: (Acute oral Risperidone) | | |
|---|---|---|
| | Blood glucose level compared to vehicle after 120 min | |
| Dosage of Risperidone (mg/kg) | Risperidone NA salt | Risperidone |
| 12 | 1.19 | 1.62 |

Example 25. Characterization of Paliperidone:Benzoic Acid 1:1 Salt

The solubility of the salt in water was determined to be 10.4 mg/mL at 25° C., while the solubility of the non-salt form of paliperidone was determined to be 0.29 mg/mL under the same temperature. Thus, the benzoic acid salt is significantly more soluble than the non-salt form.

The Carr Index of the 1:1 salt was 13%, which is lower than the 29% value obtained when the non-salt form was tested.

Example 26. The Therapeutic Effectiveness of Paliperidone and Paliperidone:Benzoic Acid (1:1) Salt The objective of this experiment was to compare the therapeutic effectiveness of paliperidone and paliperidone: benzoic acid (1:1) salt in alleviating psychotic symptoms of schizophrenia, using a mouse model having such symptoms induced by MK-801. The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age). All animal procedures were performed according to the protocols approved by Institutional Animal Care and Use Committee (IACUC).

The mice were randomly assigned into four groups listed below:

Group 1: Vehicle control
Group 2: MK-801
Group 3: Pal (0.06 mg/kg)+MK-801
Group 4: Pal:BA salt (0.076 mg/kg)+MK-801

Pal refers to paliperidone and Pal:NA refers to paliperidone:benzoic acid (1:1) salt.

Mice in Groups 2-4 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-4 orally received an acute dose of paliperidone or paliperidone:benzoic acid (1:1) salt (dissolved in $ddH_2O$ with 35% PEG400) 15 minutes prior to the MK-801 administration. The amount of paliperidone administered to Groups 3 and 4 was equal. The schizophrenia-like behavior, MK801-induced hyperactivity, were tested by open field task.

The open field task is a common measurement of novelty induced exploratory behavior and general activity in both mice and rats. The objective of this experiment was to compare the efficacy of paliperidone and its benzoic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 97 displays the effect of paliperidone and paliperidone:benzoic acid (1:1) salt on locomotion in MK-801 treated mice. The MK801 insult (0.2 mg/kg) induced hyper-locomotion in the open-field test. Both paliperidone and paliperidone:benzoic acid (1:1) salt (group 3 and 4) could alleviates MK-801 induced hyperactivity. However, the paliperidone:benzoic acid (1:1) salt shows higher potency to MK-801-induced hyperactivity in which paliperidone:benzoic acid (1:1) salt treated mice (group 3) exhibited significant decrease in locomotion activity, compared with paliperidone group. This result indicates that paliperidone: benzoic acid (1:1) salt is more potent than paliperidone and has a great potential as a novel antipsychotic medication.

TABLE 31

| Open-field test: (Acute oral Paliperidone: 0.06 mg/kg) | | |
|---|---|---|
| | Anti-hyperactivity ratio after MK801-injection $\left(\left(1-\frac{(\text{Treatment}-\text{Vehicle})}{(\text{MK801}-\text{Vehicle})}\right)\times 100\%\right)$ | |
| Dosage of Paliperidone (mg/kg) | Paliperidone BA salt | Paliperidone |
| 0.06 | 85.0% | 50.3% |

Example 27. Characterization of Paliperidone:Nicotinic Acid 1:2 Salt

The solubility of the salt in water was determined to be 137.3 mg/mL at 25° C., while the solubility of the non-salt form of paliperidone was determined to be 0.29 mg/mL under the same temperature. Thus, the nicotinic acid salt is significantly more soluble than the non-salt form.

The Carr Index of the salt was 29%, which is the same as that of the non-salt form of paliperidone.

Example 28. The Therapeutic Effectiveness of Paliperidone and Paliperidone:Nicotinic Acid (1:2) Salt The objective of this experiment was to compare the therapeutic effectiveness of paliperidone and paliperidone: nicotinic acid (1:2) salt in alleviating psychotic symptoms of schizophrenia, using a mouse model having such symptoms induced by MK-801. The testing compounds and MK-801 were administrated in mice, respectively, by oral gavage and intraperitoneal (i.p.) injections before the behavioral tests (i.e., open field test).

Materials and Methods

Animal and Housing Conditions:

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age). All animal procedures were performed according to the protzocols approved by Institutional Animal Care and Use Committee (IACUC).

The mice were randomly assigned into four groups listed below:

Group 1: Vehicle control

Group 2: MK-801

Group 3: Pal (0.06 mg/kg)+MK-801

Group 4: Pal:NA salt (0.094 mg/kg)+MK-801

Pal refers to paliperidone and Pal:NA refers to paliperidone:nicotinic acid (1:2) salt.

Mice in Groups 2-4 received an acute dose of MK-801 (Sigma-Aldrich USA), a NMDA receptor antagonist, dissolved in normal saline, at 0.2 mg/kg by i.p. injection 20 minutes prior to open field test. Each mouse in Groups 3-4 orally received an acute dose of paliperidone or paliperidone:nicotinic acid (1:2) salt (dissolved in $ddH_2O$ with 35% PEG400) 15 minutes prior to the MK-801 administration. The amount of paliperidone administered to Groups 3 and 4 was equal. The schizophrenia-like behavior, NMDA-hypofunction-induced hyperactivity, were tested by open field task.

The open field task is a common measurement of novelty induced exploratory behavior and general activity in both mice and rats. The objective of this experiment was to compare the efficacy of paliperidone and its nicotinic acid salt on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photobeam Activity System (PAS)-open field (San Diego Instruments, San Diego, Calif., USA). The total number of photo beam breaks of each mouse was measured as an index of locomotor activity.

FIG. 98 displays the effect of paliperidone and paliperidone:nicotinic acid (1:2) salt on locomotion in MK-801 treated mice. The MK801 insult (0.2 mg/kg) induced hyperlocomotion in the open-field test. Both paliperidone and paliperidone:nicotinic acid (1:2) salt (group 3 and 4) could alleviates MK-801 induced hyperactivity. However, the paliperidone:nicotinic acid (1:2) salt shows higher potency to MK-801-induced hyperactivity in which paliperidone:nicotinic acid (1:2) salt treated mice (group 3) exhibited significant decreases in locomotion activity, compared with paliperidone group. This result indicates that paliperidone: nicotinic acid (1:2) salt is more potent than paliperidone and has a great potential as a novel antipsychotic medication.

TABLE 32

| Open-field test: (Acute oral Paliperidone: 0.06 mg/kg) | | |
|---|---|---|
| | Anti-hyperactivity ratio after MK801-injection $\left(\left(1-\frac{(\text{Treatment}-\text{Vehicle})}{(\text{MK801}-\text{Vehicle})}\right)\times 100\%\right)$ | |
| Dosage of Paliperidone (mg/kg) | Paliperidone NA salt | Paliperidone |
| 0.06 | 89.7% | 50.3% |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A salt of a neuroceutical and an acid, wherein:

(a) the neuroceutical is selected from the group consisting of clozapine, quetiapine, risperidone, paliperidone, or olanzapine; and (b) the acid is selected from the group consisting of benzoic acid, nicotinic acid, and pantothenic acid;

wherein (I) the molar ratio of the neuroceutical and the acid in the salt is 1:1 and the salt is selected from the group consisting of:

a) a benzoic acid salt of clozapine, and wherein the salt comprises a solid form having a powder X-ray diffraction pattern, which comprises characteristic peaks at a reflection angle 2θ of approximately 7.6, 12.4, 13.6, 15.3, 15.7, 16.0, 19.5, 19.9, 23.1, 24.9, 25.1, and 28.4 degrees;

b) a nicotinic acid salt of clozapine, and wherein the nicotinic acid salt of clozapine comprises a solid form having a powder X-ray diffraction pattern, which comprises characteristic peaks at a reflection angle 2θ of approximately 7.7, 8.2, 10.9, 12.6, 13.8, 16.0, 17.9, 18.2, 18.8, 19.5, 21.9, 22.2, 22.4, 23.3, 24.1, 25.2, 31.2, 31.5, 35.0, and 44.2 degrees;

c) a nicotinic acid salt of quetiapine, and wherein the nicotinic acid salt of quetiapine comprises a solid form having a powder X-ray diffraction pattern, which comprises characteristic peaks at a reflection angle 2θ of approximately 6.2, 9.2, 10.3, 11.4, 12.4, 12.9, 16.2, 16.5, 17.0, 17.2, 17.3, 17.5, 19.4, 19.9, 21.1, 21.3, 22.1, 27.1, 32.9, and 35.6 degrees;

d) a nicotinic acid salt of risperidone, and wherein the nicotinic acid salt of risperidone comprises a solid form having a powder X-ray diffraction pattern, which comprises characteristic peaks at a reflection angle 2θ of approximately 9.7, 10.9, 12.0, 12.4, 14.4, 17.1, 17.4, 24.4, 36.8, 42.8, and 44.1 degrees; and e) a benzoic acid salt of paliperidone, and wherein the benzoic acid salt of paliperidone comprises a solid form having a powder X-ray diffraction pattern, which comprises characteristic peaks at a reflection angle 2θ of approximately 6.8, 9.0, 10.9, 11.4, 11.8, 16.6, 18.3, 18.6, 20.8, 22.2, 22.8, 27.5, 29.0, 30.3, and 32.3 degrees; or (II) the molar ratio of the neuroceutical and the acid in the salt is 1:2 and the salt is a nicotinic acid salt of paliperidone, and wherein the nicotinic acid salt of paliperidone comprises a solid form having a powder X-ray diffraction pattern, which comprises peaks at a reflection angle 2θ of approximately 6.7, 8.9, 11.0, 11.2, 11.7, 16.1, 16.4, 17.6, 18.4, 22.8, 27.2, and 29.9 degrees; or (III) the molar ratio of the neuroceutical and the acid in the salt is 5:1 and the salt is a pantothenic acid salt of olanzapine, and wherein the pantothenic acid salt comprises a solid form having a powder X-ray diffraction pattern, which comprises characteristic peaks at a reflection angle 2θ of approximately 7.7, 8.1, 8.7, 11.2, 11.7, 13.5, 15.4, 16.0, 16.2, 16.4, 19.0, 20.3, 22.2, 22.4, 23.1, 24.4, 25.7, 25.8, 26.7, 27.7, 29.4, 33.6, 34.3, 34.6, and 37.7 degrees.

2. The salt of claim 1, wherein the molar ratio of the neuroceutical and the acid in the salt is 1:1 and the salt is selected from the group consisting of:

(a) a benzoic acid salt of clozapine, and wherein the salt comprises a solid form having a powder X-ray diffraction pattern, which comprises characteristic peaks at a reflection angle 2θ of approximately 7.6, 12.4, 13.6, 15.3, 15.7, 16.0, 19.5, 19.9, 23.1, 24.9, 25.1, and 28.4 degrees;

(b) a nicotinic acid salt of clozapine, and wherein the nicotinic acid salt of clozapine comprises a solid form having a powder X-ray diffraction pattern, which comprises characteristic peaks at a reflection angle 2θ of approximately 7.7, 8.2, 10.9, 12.6, 13.8, 16.0, 17.9, 18.2, 18.8, 19.5, 21.9, 22.2, 22.4, 23.3, 24.1, 25.2, 31.2, 31.5, 35.0, and 44.2 degrees;

(c) a nicotinic acid salt of quetiapine, and wherein the nicotinic acid salt of quetiapine comprises a solid form having a powder X-ray diffraction pattern, which comprises characteristic peaks at a reflection angle 2θ of approximately 6.2, 9.2, 10.3, 11.4, 12.4, 12.9, 16.2, 16.5, 17.0, 17.2, 17.3, 17.5, 19.4, 19.9, 21.1, 21.3, 22.1, 27.1, 32.9, and 35.6 degrees;

(d) a nicotinic acid salt of risperidone, and wherein the nicotinic acid salt of risperidone comprises a solid form having a powder X-ray diffraction pattern, which comprises characteristic peaks at a reflection angle 2θ of approximately 9.7, 10.9, 12.0, 12.4, 14.4, 17.1, 17.4, 24.4, 36.8, 42.8, and 44.1 degrees; and (e) a benzoic acid salt of paliperidone, and wherein the benzoic acid salt of paliperidone comprises a solid form having a powder X-ray diffraction pattern, which comprises characteristic peaks at a reflection angle 2θ of approximately 6.8, 9.0, 10.9, 11.4, 11.8, 16.6, 18.3, 18.6, 20.8, 22.2, 22.8, 27.5, 29.0, 30.3, and 32.3 degrees.

3. The salt of claim 1, wherein the molar ratio of the neuroceutical and the acid in the salt is 1:2, and the salt is a nicotinic acid salt of paliperidone, and wherein the nicotinic acid salt of paliperidone comprises a solid form having a powder X-ray diffraction pattern, which comprises peaks at a reflection angle 2θ of approximately 6.7, 8.9, 11.0, 11.2, 11.7, 16.1, 16.4, 17.6, 18.4, 22.8, 27.2, and 29.9 degrees.

4. The salt of claim 1, wherein the molar ratio and acid in the salt is 5:1, and the salt is a pantothenic acid salt of olanzapine, and wherein the pantothenic acid salt comprises a solid form having a powder X-ray diffraction pattern, which comprises characteristic peaks at a reflection angle 2θ of approximately 7.7, 8.1, 8.7, 11.2, 11.7, 13.5, 15.4, 16.0, 16.2, 16.4, 19.0, 20.3, 22.2, 22.4, 23.1, 24.4, 25.7, 25.8, 26.7, 27.7, 29.4, 33.6, 34.3, 34.6, and 37.7 degrees.

5. A composition comprising a salt of claim 1 and a pharmaceutically acceptable carrier.

6. A method of treating a central nervous system (CNS) disorder or a metabolic disorder associated with a central nervous system (CNS) disorder, the method comprising administering to a human subject in need thereof an effective amount of a salt of claim 1.

7. The composition of claim 5, wherein the composition further comprises an additional therapeutic agent, which is different from the neuroceutical in the salt.

8. The composition of claim 7, wherein the additional therapeutic agent is an antipsychotic drug, an antidepressant drug, an analgesic drug, an anticonvulsant drug, or a neurodegeneration drug.

9. The composition of claim 7, wherein the additional therapeutic agent is selected from the group consisting of butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, LY2140023, droperidol, pimozide, butaperazine, carphenazine, remoxipride, piperacetazine, sulpiride, acamprosate, chlorpromazine, blonanserine, bromperidol, carpipramine, clocapramine, clotiapine, cyamemazine, fluspirilene, haloperidol, iloperidone, loxapine, lurasidone, melperone, molindone, mosapramine, nemonapride, oxypertine, penfluridol, pyrazine, pericyazine, perospirone, pipamperone, pipotiazine, prothipendyl, sertindole, spiperone, sultopride, tiapride, timiperone, zotepine, haloperidol decanoate, fluphenazine decanoate, fluphenazine enanthate, risperdal consta, acetophenazine, donepezil, galantamine, memantine, riluzole, rivastigmine, tacrine, bupropion, lithium, mirtazapine, nortriptyline, sertraline, triiodothyronine, tranylcypromine, venlafaxine, amitriptyline, imipramine, nortriptiline, protriptyline, desipramine, trimipramine, amoxapine, bupropion, citalopram, escitalopram, clomipramine, desipramine, doxepin, duloxetine, milnacipran, fluoxetine, fluvoxamine, imipramine, isocarboxazid, isoniazid, iproniazid, fluoxetine, paroxetine, sarcosine, sertraline fluvoxamine, venlafaxine, velafaxine, milnacipram and duloxetine, mirtazapine, mianserin, reboxetine, selegiline, tranylcypromine, trazodone, nefazodone, phenelzine, diazepam, bromazepam, prazepam, chlordiazepoxide, clobazam, estazolam, flurazepam, clonazepam, temazepam, triazolam, alprazolam, midazolam, brotizolam, nitrazepam, flunitrazepam, oxazepam, quazepam, lorazepam, temazepam, triazolam, zolpidem, zopiclone, zaleplon, carphenazine, remoxipride, piperacetazine, lamatrogine, topiramate, gabapentin, carbamazepine, oxacarbazepine, valporate, maprotiline, brofaromine, gepirone, moclobemide, physostigmine, nicotine, huperzine alpha, vitamin c, vitamin, carotenoids, *Ginkgo biloba*, statinsamphetamine, modafinil, desoxyn, methamphetamine, cocaine, arecoline, dexmethylphenidate, dextroamphetamine, methylphenidate, lisdexamfetamine dimesylate (vyvanse), mixed salts amphetamine, atomoxetine, clonidine hydrochloride, guanfacine hydrochloride, arecoline, pemoline, acetaminophen, aspirin, bromfenac, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, nepafenac, oxaprozin, phenylbutazone, piroxicam, sulindac, tolmetin, celecoxib, lidocaine, nefopam, orphenadrine, cyclobenzaprine, hyoscine, fentanyl, hydrocodone, hydromorphone, levorphanol, meperidine, methadone, oxycodone, oxymorphone, propoxyphene, tapentadol, tramadol, buprenorphine, butorphanol, nalbuphine, pentazocine, acetazolamide, divalproex sodium, eslicarbazepine, ethosuximide, ethotoin, felbamate, fosphenytoin, lacosamide, levetiracetam, mephenytoin, metharbital, methsuximide, methazolamide, oxcarbazepine, phenobarbital, phenytoin, phensuximide, pregabalin, primidone, valproic acid, sodium valproate, stiripentol, tiagabine, topiramate, trimethadione, vigabatrin, zonisamide, xenazine, tereabenazine, baclofen, austedo, lioresal, kemstro, deutetrabenazine, edaravone, acetylcholinesterase (AChE) inhibitors, levodopa, and a monoamine oxidase-B inhibitor.

10. The method of claim 6, further comprising administering to the human subject an additional therapeutic agent, which is different from the neuroceutical in the salt.

11. The method of claim 6, wherein the salt is a nicotinic acid salt and wherein the amount of the salt is sufficient to mitigate one or more metabolic symptoms in the human subject.

12. The method of claim 6, wherein the human subject has or is suspected of having a neuropsychiatric disorder.

13. The method of claim 12, wherein the neuropsychiatric disorder is selected from the group consisting of schizophrenia, psychotic disorder, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorder, attention deficit disorder, obsessive compulsive disorder, tic disorder, childhood learning disorder, premenstrual syndrome, depression, major depressive disorder, anhedonia, suicidal ideation and/or behavior, bipolar disorder, anxiety disorder, panic disorder, post-traumatic stress disorder, chronic mild and unpredictable stress, eating disorder, addiction disorder, personality disorder, Parkinson's disorder, Huntington's disorder, multiple sclerosis, amyotrophic lateral sclerosis, ataxia, Friedreich's ataxia, Tourette's syndrome, nocturnal enuresis, non-epileptic seizure, blepharospasm, Duchenne muscular dystrophy, stroke, chronic pain, neuropathic pain, hyperalgesia, allodynia, diabetic polyneuropathy, seizures and epilepsy.

14. The method of claim 6, wherein the human subject is administered the salt or the composition comprising such at a frequency of four times a day to one time every three months.

15. The method of claim 6, wherein the human subject has undergone or is treated concurrently with one or more additional therapeutic agents for the CNS disorder, and wherein the one or more therapeutic agents are different from the neuroceutical in the salt.

16. The method of claim 15, wherein the additional therapeutic agent is an antipsychotic drug, an antidepressant drug, an analgesic drug, an anticonvulsant drug or a neurodegeneration drug.

17. The method of claim 6, wherein the CNS disorder is a neurodegenerative disease, which is selected from the group consisting of amyotrophic lateral sclerosis, dementia, Alzheimer's disease, Parkinson's disease, and Huntington's disease.

18. The method of claim 15, wherein the additional therapeutic agent is selected from the group consisting of butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, a dopamine partial agonist, lamotrigine, memantine, tetrabenazine, cannabidiol, LY2140023, droperidol, pimozide, butaperazine, carphenazine, remoxipride, piperacetazine, sulpiride, acamprosate, chlorpromazine, blonanserine, bromperidol, carpipramine, clocapramine, clotiapine, cyamemazine, fluspirilene, haloperidol, iloperidone, loxapine, lurasidone, melperone, molindone, mosapramine, nemonapride, oxypertine, penfluridol, pyrazine, pericyazine, perospirone, pipamperone, pipotiazine, prothipendyl, sertindole, spiperone, sultopride, tiapride, timiperone, zotepine, haloperidol decanoate, fluphenazine decanoate, fluphenazine enanthate, risperdal consta, acetophenazine, donepezil, galantamine, memantine, riluzole, rivastigmine, tacrine, bupropion, lithium, mirtazapine, nortriptyline, sertraline, triiodothyronine, tranylcypromine, venlafaxine, amitriptyline, imipramine, nortriptiline, protriptyline, desipramine, trimipramine, amoxapine, bupropion, citalopram, escitalopram, clomipramine, desipramine, doxepin, duloxetine, milnacipran, fluoxetine, fluvoxamine, imipramine, isocarboxazid, isoniazid, iproniazid, fluoxetine, paroxetine, sarcosine, sertraline fluvoxamine, venlafaxine, velafaxine, milnacipram and duloxetine, mirtazapine, mianserin, reboxetine, selegiline, tranylcypromine, trazodone, nefazodone, phenelzine, diazepam, bromazepam, prazepam, chlordiazepoxide, clobazam, estazolam, flurazepam, clonazepam, temazepam, triazolam, alprazolam, midazolam, brotizolam, nitrazepam, flunitrazepam, oxazepam, quazepam, lorazepam, temazepam, triazolam, zolpidem, zopiclone, zaleplon, carphenazine, remoxipride, piperacetazine, lamatrogine, topiramate, gabapentin, carbamazepine, oxacarbazepine, valporate, maprotiline, brofaromine, gepirone, moclobemide, physostigmine, nicotine, huperzine alpha, vitamin c, vitamin, carotenoids, *Ginkgo biloba*, statinsamphetamine, modafinil, desoxyn, methamphetamine, cocaine, arecoline, dexmethylphenidate, dextroamphetamine, methylphenidate, lisdexamfetamine dimesylate (vyvanse), mixed salts amphetamine, atomoxetine, clonidine hydrochloride, guanfacine hydrochloride, arecoline, pemoline, acetaminophen, aspirin, bromfenac, diclofenac, diflunisal, etodolac, fenoprofen, flurbiprofen, ibuprofen, indomethacin, ketoprofen, ketorolac, meclofenamate, mefenamic acid, meloxicam, nabumetone, naproxen, nepafenac, oxaprozin, phenylbutazone, piroxicam, sulindac, tolmetin, celecoxib, lidocaine, nefopam, orphenadrine, cyclobenzaprine, hyoscine, fentanyl, hydrocodone, hydromorphone, levorphanol, meperidine, methadone, oxycodone, oxymorphone, propoxyphene, tapentadol, tramadol, buprenorphine, butorphanol, nalbuphine, pentazocine, acetazolamide, divalproex sodium, eslicarbazepine, ethosuximide, ethotoin, felbamate, fosphenytoin, lacosamide, levetiracetam, mephenytoin, metharbital, methsuximide, methazolamide, oxcarbazepine, phenobarbital, phenytoin, phensuximide, pregabalin, primidone, valproic acid, sodium valproate, stiripentol, tiagabine, topiramate, trimethadione, vigabatrin, zonisamide, xenazine, tereabenazine, baclofen, austedo, lioresal, kemstro, deutetrabenazine, edaravone, acetylcholinesterase (AChE) inhibitors, levodopa, and a monoamine oxidase-B inhibitor.

* * * * *